US009938551B2

(12) United States Patent
Bott et al.

(10) Patent No.: US 9,938,551 B2
(45) Date of Patent: Apr. 10, 2018

(54) VARIANTS OF CELLOBIOHYDROLASES

(71) Applicant: Danisco US Inc., Palo Alto, CA (US)

(72) Inventors: Richard R. Bott, Burlingame, CA (US); Maria Foukaraki, Rotterdam (NL); Ronaldus Wilhelmus Hommes, Haarlem (NL); Thijs Kaper, Half Moon Bay, CA (US); Bradley R. Kelemen, Menlo Park, CA (US); Slavko Kralj, Oegstgeest (NL); Igor Nikolaev, Noordwijk (NL); Mats Sandgren, Uppsala (SE); Johannes Franciscus Thomas Van Lieshout, Utrecht (NL); Sander Van Stigt Thans, Zevenbergen (NL)

(73) Assignee: DANISCO US INC CA (US)

( * ) Notice: Subject to any disclaimer, the term of this patent is extended or adjusted under 35 U.S.C. 154(b) by 234 days.

(21) Appl. No.: 14/650,285

(22) PCT Filed: Dec. 10, 2013

(86) PCT No.: PCT/US2013/074005
§ 371 (c)(1),
(2) Date: Jun. 5, 2015

(87) PCT Pub. No.: WO2014/093275
PCT Pub. Date: Jun. 19, 2014

(65) Prior Publication Data
US 2016/0201104 A1 Jul. 14, 2016

Related U.S. Application Data

(60) Provisional application No. 61/736,315, filed on Dec. 12, 2012.

(51) Int. Cl.
*C12P 19/14* (2006.01)
*C12P 19/02* (2006.01)
*C12N 9/42* (2006.01)

(52) U.S. Cl.
CPC ............ *C12P 19/14* (2013.01); *C12N 9/2434* (2013.01); *C12N 9/2437* (2013.01); *C12P 19/02* (2013.01); *C12Y 302/01091* (2013.01)

(58) Field of Classification Search
CPC ..... C12N 9/2434; C12N 9/2437; C12P 19/02; C12P 19/14; C12Y 302/01091
See application file for complete search history.

(56) References Cited

U.S. PATENT DOCUMENTS

| 4,435,307 | A | 3/1984 | Barbesgaard et al. |
| 4,816,567 | A | 3/1989 | Cabilly et al. |
| 4,822,516 | A | 4/1989 | Suzuki et al. |
| 5,246,853 | A | 9/1993 | Clarkson et al. |
| 5,475,101 | A | 12/1995 | Ward et al. |
| 5,648,263 | A | 7/1997 | Schülein et al. |
| 5,650,322 | A | 7/1997 | Clarkson et al. |
| 5,691,178 | A | 11/1997 | Schülein et al. |
| 5,776,757 | A | 7/1998 | Schülein et al. |
| 5,861,271 | A | 1/1999 | Fowler et al. |
| 5,955,270 | A | 9/1999 | Radford et al. |
| 6,162,782 | A | 12/2000 | Clarkson et al. |
| 6,255,115 | B1 | 7/2001 | Beijersbergen et al. |
| 6,562,340 | B1 | 5/2003 | Bedford et al. |
| 6,599,722 | B2 | 7/2003 | Boston et al. |
| 7,375,197 | B2 | 5/2008 | Adney et al. |
| 7,452,707 | B2 | 11/2008 | Goedegebuur et al. |
| 7,951,570 | B2 | 5/2011 | Goedegebuur et al. |
| 7,951,571 | B2 | 5/2011 | Goedegebuur et al. |
| 7,972,832 | B2 | 7/2011 | Day et al. |
| 2003/0170861 | A1 | 9/2003 | Adney et al. |
| 2005/0048619 | A1 | 3/2005 | Teter et al. |
| 2006/0172379 | A1 | 8/2006 | Teter et al. |
| 2006/0246566 | A1 | 11/2006 | Vehmaanpera et al. |
| 2007/0173431 | A1 | 7/2007 | Day et al. |
| 2008/0289066 | A1 | 11/2008 | Lanahan et al. |
| 2008/0299613 | A1 | 12/2008 | Merino et al. |
| 2009/0019608 | A1 | 1/2009 | Lopez De Leon et al. |
| 2009/0123979 | A1 | 5/2009 | Xu |
| 2009/0130707 | A1 | 5/2009 | Zu |
| 2009/0162916 | A1 | 6/2009 | Adney et al. |
| 2009/0221039 | A1 | 9/2009 | Record et al. |
| 2009/0325240 | A1 | 12/2009 | Daniell |
| 2010/0075363 | A1 | 3/2010 | McBride et al. |
| 2010/0124769 | A1 | 5/2010 | Brown et al. |
| 2010/0129860 | A1 | 5/2010 | McFarland et al. |
| 2010/0159494 | A1 | 6/2010 | Sweeney et al. |
| 2010/0159509 | A1 | 6/2010 | Xu et al. |

(Continued)

FOREIGN PATENT DOCUMENTS

EP 0137280 A1 4/1985
EP 2322607 A1 5/2011
(Continued)

OTHER PUBLICATIONS

International Preliminary Report on Patentability, Corresponding PCT Application No. PCT/US2013/74005, dated Jun. 16, 2015.
Ahn, J-H., et al. "Molecular Cloning and Characterization of Cel2 from the Fungus *Cochlibolus carbonum*." Biosci. Biotechnol. Biochem. vol. 65, No. 6, pp. 1406-1411, 2001.
Altschul, Stephen F. et al., "Basic Local Alignment Search Tool," J. Mol. Biol., 215:403-410, 1990.
Aro, Nina et al., "ACEII, a Novel Transcriptional Activator Involved in Regulation of Cellulase and Xylanase Genes of *Trichoderma reesei*," J. Biol. Chem., vol. 276, No. 26, pp. 24309-24314, Jun. 29, 2001.

(Continued)

*Primary Examiner* — Kagnew H Gebreyesus

(57) ABSTRACT

Disclosed are a number of homologs and variants of *Hypocrea jecorina* Cel7A (formerly *Trichoderma reesei* cellobiohydrolase I or CBH1), nucleic acids encoding the same and methods for producing the same. The homologs and variant cellulases have the amino acid sequence of a glycosyl hydrolase of family 7A wherein one or more amino acid residues are substituted and/or deleted.

13 Claims, 7 Drawing Sheets

(56) References Cited

U.S. PATENT DOCUMENTS

| | | | |
|---|---|---|---|
| 2010/0159535 A1 | 6/2010 | Xu et al. |
| 2010/0159536 A1 | 6/2010 | Sweeney et al. |
| 2010/0221778 A1 | 9/2010 | Scott et al. |
| 2010/0299788 A1 | 11/2010 | Harris et al. |
| 2010/0299789 A1 | 11/2010 | Harris et al. |
| 2010/0304434 A1 | 12/2010 | Harris et al. |
| 2010/0304437 A1 | 12/2010 | Garner et al. |
| 2010/0306881 A1 | 12/2010 | Harris et al. |
| 2011/0099671 A1 | 4/2011 | Wogulis |
| 2011/0111453 A1 | 5/2011 | McBrayer et al. |
| 2011/0124074 A1 | 5/2011 | Den Haan et al. |
| 2011/0189744 A1 | 8/2011 | McBride et al. |
| 2011/0296558 A1 | 12/2011 | Lopez De Leon et al. |
| 2011/0312054 A1 | 12/2011 | Brevnova et al. |
| 2012/0003703 A1 | 1/2012 | Mitchell et al. |
| 2012/0040409 A1 | 2/2012 | Hau et al. |
| 2012/0096597 A1 | 4/2012 | Schnorr et al. |
| 2012/0129229 A1 | 5/2012 | McBride et al. |
| 2013/0123115 A1 | 5/2013 | Kettling et al. |
| 2013/0177959 A1 | 7/2013 | Blanquet et al. |

FOREIGN PATENT DOCUMENTS

| | | |
|---|---|---|
| GB | 1368599 | 10/1974 |
| GB | 2094826 | 9/1982 |
| GB | 2095275 | 9/1982 |
| WO | WO-91/04673 | 4/1991 |
| WO | WO-92/06209 | 4/1992 |
| WO | WO-94/28117 | 12/1994 |
| WO | WO-98/21339 | 5/1998 |
| WO | WO-98/31821 | 7/1998 |
| WO | 199906574 A1 | 2/1999 |
| WO | WO-99/006574 | 2/1999 |
| WO | WO-01/04284 | 1/2001 |
| WO | 2004016760 A2 | 2/2004 |
| WO | WO-2004/016760 | 2/2004 |
| WO | 2005001036 A2 | 1/2005 |
| WO | 2006110901 A2 | 10/2006 |
| WO | 2006117432 A1 | 11/2006 |
| WO | 2009048488 A1 | 4/2009 |
| WO | 2010141779 A1 | 12/2010 |
| WO | 2011038019 A2 | 3/2011 |
| WO | 2012048171 A1 | 4/2012 |

OTHER PUBLICATIONS

Bajar, Aslam, et al., "Identification of a fungal cutinase promoter that is inducible by a plant signal via a phosphorylated trans-acting factor," Proc. Natl. Acad. Sci. USA, vol. 88, pp. 8208-8212, Sep. 1991.

Ballance, D.J., et al., "Transformation of Aspergillus nidulans by the Orotidine-5'-Phosphate Decarboxylase Gene of Neurospora crassa," Biochemical and Biophysical Research Communications, vol. 112, No. 1, pp. 284-289, Apr. 15, 1983.

Baulcombe, D., "Viruses and gene silencing in plants," Archives of Virology, Calisher and Horzinek eds., Springer-Verlag, New York, NY 15:189-201, 1999.

Becker, et al., "Engineering of a glycosidase Family 7 cellobiohydrolase to more Alkaline pH optimum: The pH behaviour of Trichoderma reesei Cel7A and its E22/A224H/L225V/T226A/D262G mutant," Biochemical Journal, V356:1 (May 15, 2001 pp. 19-30.

Berges, Thierry et al., "Isolation of uridine auxotrophs from Trichoderma reesei and efficient transformation with the cloned ura3 and ura5 genes," Curr. Genet. vol. 19, pp. 359-365, 1991.

Bhikhabhai, Ramagauri et al., "Isolation of Cellulolytic Enzymes from Trichoderma reesei QM 9414," J. Appl. Biochem. 6:336-345, 1984.

Brumbauer, Aniko et al., "Fractionation of cellulase and .beta.-glucosidase in a Trichoderma reesei culture liquid by use of two-phase partitioning," Bioseparation 7:287-295, 1999.

Burley, S.K. et al., "Aromatic-Aromatic Interaction: A Mechanism of Protein Structure Stabilization," Science 229:23-28, 1985.

Cadwell, Craig R., et al., "Randominzation of Genes by PCR Mutagenesis," PCR Methods and Applications, 2:28-33, 1992.

Campbell, Edward I., et al., "Improved transformation efficiency of Aspergillus niger using the homologous niaD gene for nitrate reductase," Current Genetics, 16:53-56, 1989.

Cao, Qing-Na et al., "Penicillopepsin-JT2, a recombinant enzyme from Penicillium janthinellum and the contribution of a hydrogen bond in subsite S.sub.3 to k.sub.cat," Protein Science, vol. 9, pp. 991-1001, 2000.

Carter, Paul et al., "Improved oligonucleotide site-directed mutagenesis using M13 vectors," Nucleic Acids Research, vol. 13, No. 12, pp. 4431-4443, 1985.

Cees, A. M. et al., "Heterologous Gene Expression in Filamentous Fungi," More Gene Manipulations in Fungi, Bennett, J.W. et al., ed., pp. 396-428, Academic Press, 1991.

Cheng et al. GenBank Accession No. S11439, created Nov. 21, 1993.

Cheng, C., et al. "Nucleotide sequence of the cellobiohydrolase gene from Trichoderma viride." Nucleic Acids Research, vol. 18, No. 18, p. 5559, 1990.

Coughlan, Michael, P. et al., "Comparative Biochemistry of Fungal and Bacterial Cellulolytic Enzyme Systems," Biochemistry and Genetics of Cellulose Degradation, pp. 11-30 1988.

Covert, S.F., et al. "Genomic Organizations of a Cellulase Gene Family in Phanerochaete chrysosporium." Curr. Genet., vol. 22, pp. 407-413, 1992.

Covert, S.F., et al. "Structure, Organization, and Transcription of a Cellobiohydrolase Gene Cluster from Phanerochaete chrysosporium." Appl. Environ. Microbiol., vol. 58, No. 7, pp. 2168-2175, Jul. 1992.

Cummings, C. et al., "Secretion of Trichoderma reesei .beta.-glucosidase by Saccharomyces cerevisiae," Curr. Genet. 29:227-233, 1996.

Davies, Gideon J., "Oligosaccharide specificity of a family 7 endoglucanase: Insertion of potential sugar-binding subsites," Journal of Biotechnology, 57:91-100, 1997.

Deutscher, Murray P., "Rethinking Your Purification Procedure," Methods in Enzymology, vol. 182, No. 57, p. 779, 1990.

Divne, Christina, et al., "High-resolution Crystal Structures Reveal How a Cellulose Chain is Bound in the 50 .ANG. Long Tunnel of Cellobiohydrolase I from Trichoderma reesei," J. Mol. Biol., 275:309-325, 1998.

Ellouz, S. et al., "Analytical Separation of Trichoderma reesei Cellulases by Ion-Exchange Fast Protein Liquid Chromatography," Journal of Chromatography, 396:307-317, 1987.

Eriksson, A. E., et al., "Response of a Protein Structure to Cavity-Creating Mutations and its Relation to the Hydrophobic Effect," Science, 255:178-183, 1992.

Filho, Edivaldo X. F., "Purification and characterization of a .beta.-glucosidase from solid-state cultures of Humicola grisea var. thermoidea," Can. J. Microbiol., 42:1-5, 1996.

Fliess, A., et al., "Characterization of Cellulases by HPLC Separation," Eur. J. Appl. Microbiol. Biotechnol., vol. 17, pp. 314-318, 1983.

Freer, Shelby N., "Kinetic Characterization of a .beta.-Glucosidase from a Yeast, Candida wickerhamii," J. Biol. Chem., vol. 268, No. 13, pp. 9337-9342, 1993.

Gloss, Lisa M., et al., "Urea and Thermal Equilibrium Denaturation Studies on the Dimerization Domain of Escherichia coil Trp Repressor," Biochem., vol. 36, No. 19, pp. 5612-5623, 1997.

Goedegebuur, Frits, et al., "Cloning and relational analysis of 15 novel fungal endoglucanases from family 12 glycosyl hydrolase," Current Genetics, vol. 41, pp. 89-98, 2002.

Goldman, G. H., et al., "Transformation of Trichoderma harzianum by high-voltage electric pulse," Current Genetics, 17:169-174, 1990.

Goyal, Anil, et al., "Characteristics of Fungal Cellulases," Bioresource Technology, vol. 36, pp. 37-50, 1991.

Gross, L.S., et al. "Changing the properties of Hypocrea jecorina Cel7A (Trichoderma reesei CBH1) by single amino acid mutations." Biophys. J., vol. 82, No. part 2, p. 459a, Jan. 2002.

(56) References Cited

OTHER PUBLICATIONS

Halldorsdottir, S, et al., "Cloning, sequencing and overexpression of a Rhodothermus marinus gene encoding a thermostable cellulase of glycosyl hydrolase family 12," Appl. Microbiol. Biotechnol., 49(3):277-284, 1998.
Hemmpel, W. H., "The surface modification of woven and knitted cellulose fibre fabrics by enzymatic degradation," ITB Dyeing/Printing/Finishing, 3:5-14, 1991.
Henikoff, Steven, et al., "Amino acid substitution matrices from protein blocks," Proc. Natl. Acad. Sci. USA, 89:10915-10919, Nov. 1992.
Higuchi, Russell, "Recombinant PCR," PCR Protocols: A Guide to Methods and Applications, pp. 177-183, Academic Press, Inc. 1990.
Himmel, Michael E., "Adanced Bioethanol Production Technologies: A Perspective," American Chemical Society, pp. 2-45, 1997.
Hu, Qianjin, et al., "Antibodies Specific for the Human Retinoblastoma Protein Identify a Family of Related Polypeptides," Molecular and Cellular Biology, vol. 11, No. 11, pp. 5792-5799, Nov. 1991.
Ilmen, Marja, et al., "Regulation of Cellulase Gene Expression in the Filamentous Fungus Trichoderma reesei," Appl. And Envir. Micro., vol. 63, No. 4, pp. 1298-1306, Apr. 1997.
Jakobovits, Aya, "Production of fully human antibodies by transgenic mice," Curr. Opin. Biotechnol., 6(5):561-566, 1995.
Jakobovits, Aya, et al., "Production of Antigen-Specific Human Antibodies from Mice Engineered with Human Heavy and Light Chain YACs.sup.3," Annals New York Academy of Sciences, 764:525-535, 1995.
Jones, Peter T. et al., "Replacing the complementarity—determining regions in a human antibody with those from a mouse," Nature, 321:522-525, 1986.
Karlin, Samuel, et al., "Applications and statistics for multiple high-scoring segments in molecular sequences," Proc. Natl. Acad. Sci. USA, 90:5873-5877, 1993.
Kawaguchi, Takashi, et al., "Cloning and sequencing of the cDNA encoding .beta.-glucosidase 1 from Aspergillus aculeatus," Gene 173(2):287-288, 1996.
Kellis, James T. Jr., et al., "Contribution of hydrophobic Interactions to protein stability," Nature, 333:784-786, 1988.
Kleywegt, Gerard J., "The Crystal Structure of the Catalytic Core Domain of Endoglucanase I from Trichoderma reesei at 3.6 .ANG. Resolution, and a Comparison with Related Enzymes," J. Mol. Biol., 272:383-397, 1997.
Knowles, Jonathan, et al., "Cellulase families and their genes," TIBTECH 5, pp. 255-261, 1987.
Kohler, G. et al., "Continuous cultures of fused cells secreting antibody of predefined specificity," Nature, vol. 256, pp. 495-499, Aug. 7, 1975.
Krishna, S. Hari, et al., "Simultaneous saccharification and fermentation of lignocellulosic wastes to ethanol using a thermotolerant yeast," Bioresource Tech., 77:193-196, 2001.
Kuhls, K., et al., "Molecular evidence that the asexual industrialfungus Trichoderma reesei is a clonal derivative of the ascomycete Hypocrea jecorina," Proc. Natl. Acad. Sci. USA, vol. 92, pp. 7755-7760, Jul. 1996.
Kumar, Akhil, et al., "Optimizing the Use of Cellulase Enzymes in Finishing Cellulosic Fabrics," Textile Chemist and Colorist, 29:37-42, Apr. 1997.
Kunkel, Thomas A., "Rapid and efficient site-specific mutagenesis without phenotypic selection," Proc. Natl. Acad. Sci. USA, vol. 82, pp. 488-492, Jan. 1985.
Lazraq, R., et al., "Conjugative transfer of a shuttle plasmid for Escherichia coil to Mycobacterium smegmatis," FEMS Microbiology Letters, 69:135-138, 1990.
Li, Xin-Liang, et al., "Expression of Aureobasidium pullulans xynA in, and Secretion of the Xylanase from, Saccharomyces cerevisiae," Applied and Environmental Microbiology, vol. 62, No. 1, pp. 209-213, 1996.
Linder, Marcus et al., "The roles and function of cellulose-binding domains," Journal of Biotechnol. 57:15-28, 1997.

Linko, Matti, Proceedings of the Second TRICEL Symposium on Trichoderma reesei Cellulases and Other Hydrolases, Espoo 1993, ed. by P. Suominen & T. Reinikainen. Foundation for Biotechnical and Industrial Fermentation Research 8, pp. 9-11, 1993.
Lorito, M., et al., "Biolistic transformation of Trichoderma harzianum and Gliocladium virens using plasmid and genomic DNA," Current Genetics, 24:349-356, 1993.
Luo, J., et al., "Detection of a Stable Intermediate in the Thermal Unfolding of a Cysteine-Free Form of Dihydrofolate Reductase from Escherichia coli," Biochem., vol. 34, No. 33, pp. 10669-10675, 1995.
Matthews, B. W., et al., "Enhanced protein thermostability from site-directed mutations that decrease the entropy of unfolding," Proc. Natl. Acad. Sci. USA, vol. 84, pp. 6663-6667, 1987.
Matthews, Brian W.,"Structural and Genetic Analysis of Protein Stability," Annu. Rev. Biochem., 62:139-160, 1993.
Medve, Jozsef et al., "Ion-exchange chromatographic purification and quantitative analysis of Trichoderma reesei cellulases cellobiohydrolase I, II and endoglucanase II by fast protein liquid chromatography," J. Chromatography A, 808:153-165, 1998.
Mitsuishi, Yasushi, et al., "Site-directed mutagenesis of the putative catalytic residues of Trichoderma reesei, cellobiohydrolase I and endoglucanase I," FEBS, 275(1.2):135-138, 1990.
Munoz et al. Family 7 cellobiohydrolases from Phanerochaete chrysosporium: Crystal structure of the catalytic module of Cel7D (CBH58) at 1.32 A resolution and homology models of the isozymes, J Mol Biol. Dec. 14, 2001;314(5):1097-111.
Needleman, Saul B., "A General Method Applicable to the Search for Similarities in the Amino Acid Sequence of Two Proteins," J. Mol. Biol., 48:443-453, 1970.
Nevalainen, H., et al., "Molecular Biology of Cellulolytic Fungi," The Mycota II, Genetics and Biotechnology, Kuck (Ed.), Springer-Verlag Berlin Heidelberg, 1995, pp. 303-319.
Nidetzky, Bernd, "Specific Quantification of Trichoderma reesei Cellulases in Reconstituted Mixtures and its Application to Cellulase-Cellulose Binding Studies," Biotechnology and Bioengineering, vol. 44, pp. 961-966, 1994.
Ohmiya, Kunio, et al., "Structure of Cellulases and Their Applications," Biotechnol. Gen. Engineer. Rev., vol. 14, pp. 365-414, 1997.
Ooi, Toshihiko, et al., "Complete nucleotide sequence of a gene coding for Aspergillus aculeatus cellulase (FI-CMCase)", Nucleic Acids Research, vol. 18, No. 19, 1990.
Pearson, William R., et al., "Improved tools for biological sequence comparison," Proc. Natl. Acad. Sci. USA, vol. 85, pp. 2444-2448, Apr. 1988.
Penttila, Marja E., et al., "Expression of Two Trichoderma reesei Endoglucanases in the Yeast Saccharomyces cerevisiae," Yeast, vol. 3, pp. 175-185, 1987.
Penttila, Menta E., et al., "A versatile transformation system for the cellulolytic filamentous fungus Trichoderma reesei," Gene, vol. 61, pp. 155-164, 1987.
Penttila, Merja E., et al., "Efficient secretion of two fungal cellobiohydrolases by Saccharomyces cerevisiae," Gene, 63:103-112, 1988.
Pere J., et al., "Use of Purified Enzymes in Mechanical Pulping," 1996 Tappi Pulping Conference, pp. 693-696, Nashville, TN.
Pourquie, J., et al., "Scale Up of Cellulase Production and Utilization," Biochemistry and Genetics of Cellulose Degradation, Academic Press Ltd., pp. 71-86, 1988.
Riechmann, Lutz, et al., "Reshaping human antibodies for therapy," Nature, vol. 332, pp. 323-327, 1988.
Rothstein, Steven J., et al., "Synthesis and secretion of wheat .alpha.-amylase in Saccharomyces cerevisiae," Gene, 55:353-356, 1987.
Russell, Rupert J. M., et aL, "Engineering thermostability: lessons from thermophilic proteins," Current Opinion in Biotechnology, 6:370-374, 1995.
Saarilahti, Hannu T., et al., "CelS: a novel endoglycanase identified from Erwinia carotovora subsp. carotovora," Gene, 90:9-14, 1990.
Sakamoto, S., et al., "Cloning and sequencing of cellulase cDNA from Aspergillus kawachii and its expression in Saccharomyces cerevisiae," Curr. Genet., 27:435-439, 1995.

(56) References Cited

OTHER PUBLICATIONS

Saloheimo, M., et al., "EGIII, a new endoglucanase from Trichoderma reesei: the characterization of both gene and enzyme," Gene, 63:11-21, 1988.
Sandgren, Mats, et al., "Comparison of family 12 glycoside hydrolases and recruited substitutions important for thermal stability," Protein Science, vol. 12, pp. 848-860, 2003.
Schülein, Martin, "Cellulases of Trichoderma reesei," Methods Enzymol., 160, 25, pp. 234-243, 1988.
Scopes, Robert K., et al. "Purification of All Glycolytic Enzymes from One Muscle Extract," Methods Enzymol., 90:479-491, 1982.
Sheehan, John, et al., "Enzymes, Energy, and the Environment: A Strategic Perspective on the U.S. Department of Energy's Research and Development Activities for Bioethanol," Biotechnol. Prog., 15:817-827, 1999.
Sheir-Neiss, G., et al., "Characterization of the secreted cellulases of Trichoderma reesei wild type and mutants during controlled fermentations," Appl. Microbiol. Biotechnol., vol. 20, pp. 46-53, 1984.
Shoemaker, S. P., et al., "Enzymic Activities of Endo-1,4-.beta.-D-Glucanases Purified From Trichoderma Viride," Biochemica et Biophysica Acta, 523:133-146, 1978.
Shoemaker, S., et al., "Molecular Cloning of Exo-Cellobiohydrolase I Derived from Trichoderma reesei Strain L27," Bio/Technology, pp. 691-696,1983.
Smith, Temple F., et al., "Comparison of Biosequences," Advances in Applied Mathematics, vol. 2, pp. 482-489, 1981.
Spilliaert, Remi, et al., "Cloning and sequencing of a Rhodothermus marinus gene, bglA, coding for a thermostable .beta.-glucanase and its expression in *Escherichia coli*," Eur. J. Biochem., 224(3):923-930, 1994.
Srisodsuk, Malee, et al., "Trichoderma reesei cellobiohydrolase I with an endoglucanase cellulose-binding domain: action on bacterial microcrystalline cellulose," Journal of Biotechnology, 57:49-57, 1997.
Stahlberg, Jerry, et al., "A New Model for Enzymatic Hydrolysis of Celluloase Based on the Two-Domain Structure of Cellobiohydrolase I," Bio/Technol., 9:286-290, 1991.
Strathern et al., eds. The Molecular Biology of the Yeast *Saccharomyces*, 1981.
Sulzenbacher, Gerlind, et al., "Structure of the Endoglucanase I from Fusarium oxysporum: Native, Cellobiose, and 3,4-Epoxybutyl .beta.-D-Cellobioside-Inhibited Forms, at 2.3 .ANG. Resolution," Biochemistry, 36:5902-5911, 1997.
Suurnakki, A., et al., "Trichoderma reesei cellulases and their core domains in the hydrolysis and modification of chemical pulp," Cellulose 7:189-209, 2000.
Tanner, John J., et al., "Determinants of Enzyme Thermostability Observed in the Molecular Structure of Thermus acquaticus D-Glyceraldehyde-3-phosphate Dehydrogenase at 2.5 .ANG. Resolution," Biochemistry, 35(8):2597-2609, 1996.
Teeri, T., T., Spec. Publ.—R. Soc. Chem., 246 (Recent Advances in Carbohydrate Bionginering), pp. 302-308, 1999.
Teeri, Tuula T., "Crystalline cellulose degradation: new insight into the function of cellobiohydrolases," TIBTECH, vol. 15, pp. 160-167, 1997.
Teeri, Tuula T., et al., "Homologous domains in Trichoderma reesei cellulolytic enzymes: gene sequence and expression of cellobiohydrolase II," Gene, 51:43-52, 1987.
Te'o, Valentino S. J., et al., "Codon optimization of xylanase gene xynB from the thermophilic bacterium Dictyoglomus thermophilum for expression in the filamentous fungus *Trichoderma reesei*," FEMS Microbiology Letters, 190:13-19, 2000.
Tomaz, Candida T., et al., "Studies on the chromatographic fractionation of Trichoderma reesei cellulases by hydrophobic interaction," J. Chromatography A, 865:123-128, 1999.
Tomme, Peter, et al., "Studies of the cellulolytic system of Trichoderma reesei QM 9414. Analysis of domain function in two cellobiohydrolases by limited proteolysis," Eur. J. Biochem., 170:575-581, 1988.
Tormo, Jose, et al., "Crystal structure of a bacterial family-III cellulose-binding domain: a general mechanism for attachment to cellulose," EMBO J. , vol. 15, No. 21, pp. 5739-5751, 1996.
Tyndall, R. M., "Improving the Softness and Surface Appearance of Cotton Fabrics and Garments by Treatment with Cellulase Enzymes," Textile Chemist and Colorist, 24(6):23-26, 1992.
Vallette, Francois, et al., "Construction of mutant and chimeric genes using the polymerase chain reaction," Nucleic Acids Research, vol. 17, No. 2, pp. 723-733, 1989.
van Hartingsveldt, Wim, et al., "Development of a homologous transformation system for Aspergillus niger based on the pyrG gene," Mol. Gen. Genet., 206:71-75, 1987.
van Rensburg, Pierre, "Engineering Yeast for Efficient Cellulose Degradation," Yeast, 14:67-76, 1998.
van Tilbeurgh, Herman, et al., Separation of endo- and exo-type cellulases using a new affinity chromatography method, FEBS, vol. 169, No. 2, pp. 215-218, 1984.
Verhoeyen, Martine, et al., "Reshaping Human Antibodies: Grafting an Antilysozyme Activity," Science, vol. 239, pp. 1534-1536, 1986.
Ward, Michael, et al., "Use of Aspergillus overproducing mutants, cured for integrated plasmid, to overproduce heterologous proteins," Appl. Microbiol. Biotechnol., vol. 39, pp. 738-743, 1993.
Watanabe, Kunihiko, et al., "Multiple proline substitutions cumulatively thermostabilize Bacillus cereus ATCC7064 oligo-1, 6-glucosidase," Eur. J. Biochem., 226:277-283, 1994.
Wells, James A., et al., "Cassette mutagenesis: an efficient method for generation of multiple mutations at defined sites," Gene, vol. 34, pp. 315-323, 1985.
Wood, Thomas M., et al., "Methods for Measuring Cellulase Activities," Methods in Enzymology, vol. 160, No. 9, pp. 87-116, 1988.
Wood, Thomas M., et al., "Properties of cellulolytic enzyme systems," Biochemical Society Transactions, 611.sup.th Meeting, Galway, vol. 13, pp. 407-410, 1985.
Yelton, M. Melanie, et al, "Transformation of Aspergillus nidulans by using a trpC plasmid," Proc. Natl. Acad. Sci., vol. 81, pp. 1470-1474, 1984.
Zeng, A.-P, et al., Microbial Conversion of Glycerol to 1,3-Propanediol: Recent Progress, Fuels and Chemicals from Biomass, pp. 264-279, 1997.
Zuber, H., "Temperature adaptation of lactate dehydrogenase Structural, functional and genetic aspects," Biophysical Chemistry, 29:171-179, 1988.

```
SEQ ID NO:1 (top)
SEQ ID NO:3 (bottom)

1      cagtcggcctgcactctccaatcggagactcacccgcctctgacatggcagaaatgctcg
1       Q  S  A  C  T  L  Q  S  E  T  H  P  P  L  T  W  Q  K  C  S 61     tctggtggcacttgcactcaacagacaggctccgtggtcatcgacgccaactggcgctgg
21      S  G  G  T  C  T  Q  Q  T  G  S  V  V  I  D  A  N  W  R  W 121    actcacgctacgaacagcagcacgaactgctacgatggcaacacttggagctcgaccta
41      T  H  A  T  N  S  S  T  N  C  Y  D  G  N  T  W  S  S  T  L 181    tgtcctgacaacgagacctgcgcgaagaactgctgtctggacggtgccgcctacgcgtcc
61      C  P  D  N  E  T  C  A  K  N  C  C  L  D  G  A  A  Y  A  S 241    acgtacggagttaccacgagcggtaacagcctctccattggctttgtcacccagtctgcg
81      T  Y  G  V  T  T  S  G  N  S  L  S  I  G  F  V  T  Q  S  A 301    cagaagaacgttggcgctcgcctttaccttatggcgagcgacacgacctaccaggaattc
101     Q  K  N  V  G  A  R  L  Y  L  M  A  S  D  T  T  Y  Q  E  F 361    accctgcttggcaacgagttctctttcgatgttgatgtttcgcagctgccgtgcggcttg
121     T  L  L  G  N  E  F  S  F  D  V  D  V  S  Q  L  P  C  G  L 421    aacggagctctctacttcgtgtccatggacgcggatggtggcgtgagcaagtatccacc
141     N  G  A  L  Y  F  V  S  M  D  A  D  G  G  V  S  K  Y  P  T 481    aacaccgctggcgccaagtacggcacggggtactgtgacagccagtgtccccgcgatctg
161     N  T  A  G  A  K  Y  G  T  G  Y  C  D  S  Q  C  P  R  D  L 541    aagttcatcaatggccaggccaacgttgagggctgggagccgtcatccaacaacgcgaac
181     K  F  I  N  G  Q  A  N  V  E  G  W  E  P  S  S  N  N  A  N 601    acgggcattggaggacacggaagctgctgctctgagatggatatctgggaggccaactcc
201     T  G  I  G  G  H  G  S  C  C  S  E  M  D  I  W  E  A  N  S 661    atctccgaggctcttaccccccacccttgcacgactgtcggccaggagatctgcgagggt
221     I  S  E  A  L  T  P  H  P  C  T  T  V  G  Q  E  I  C  E  G 721    gatgggtgcggcggaacttactccgataacagatatggcggcacttgcgatcccgatggc
241     D  G  C  G  G  T  Y  S  D  N  R  Y  G  G  T  C  D  P  D  G 781    tgcgactggaaccctataccgcctgggcaacaccagcttctacggccctggctcaagcttt
261     C  D  W  N  P  Y  R  L  G  N  T  S  F  Y  G  P  G  S  S  F 841    accctcgataccaccaagaaattgaccgttgtcacccagttcgagacgtcgggtgccatc
281     T  L  D  T  T  K  K  L  T  V  V  T  Q  F  E  T  S  G  A  I
```

FIG. 1A

SEQ ID NO:1 (top; continued)
SEQ ID NO:3 (bottom; continued)

```
901       aaccgatactatgtccagaatggcgtcactttccagcagcccaacgccgagcttggtagt
301        N  R  Y  Y  V  Q  N  G  V  T  F  Q  Q  P  N  A  E  L  G  S 961       tactctggcaacgagctcaacgatgattactgcacagctgaggaggcagaattcggcgga
321        Y  S  G  N  E  L  N  D  D  Y  C  T  A  E  E  A  E  F  G  G 1021      tcctctttctcagacaagggcggcctgactcagttcaagaaggctacctctggcggcatg
341        S  S  F  S  D  K  G  G  L  T  Q  F  K  K  A  T  S  G  G  M 1081      gttctggtcatgagtctgtgggatgattactacgccaacatgctgtggctggactccacc
361        V  L  V  M  S  L  W  D  D  Y  Y  A  N  M  L  W  L  D  S  T 1141      tacccgacaaacgagacctcctccacacccggtgccgtgcgcggaagctgctccaccagc
381        Y  P  T  N  E  T  S  S  T  P  G  A  V  R  G  S  C  S  T  S 1201      tccggtgtccctgctcaggtcgaatctcagtctcccaacgccaaggtcaccttctccaac
401        S  G  V  P  A  Q  V  E  S  Q  S  P  N  A  K  V  T  F  S  N 1261      atcaagttcggacccattggcagcaccggcaaccctagcggcggcaaccctcccggcgga
421        I  K  F  G  P  I  G  S  T  G  N  P  S  G  G  N  P  P  G  G 1321      aacccgcctggcaccaccaccacccgccgcccagccactaccactggaagctctcccgga
441        N  P  P  G  T  T  T  T  R  R  P  A  T  T  T  G  S  S  P  G 1381      cctacccagtctcactacggccagtgcggcggtattggctacagcggccccacggtctgc
461        P  T  Q  S  H  Y  G  Q  C  G  G  I  G  Y  S  G  P  T  V  C 1441      gccagcggcacaacttgccaggtcctgaaccctactactctcagtgcctg
481        A  S  G  T  T  C  Q  V  L  N  P  Y  Y  S  Q  C  L
```

FIG. 1B

```
                        1                                                50
                        |                                                 |
H. jecorina         QSACTLQSETHPPLTWQKCSSGGTCTQQTGSVVIDANWRWTHATNSSTNC
H. oriantalis       QSACTLQTETHPSLTWQKCSSGGTCTQQTGSVVIDANWRWTHATNSSTNC
H. schweinitzii     QSACTLQTETHPSLTWQKCSSGGTCTQQTGSVVIDANWRWTHATNSSTNC
T. citrinoviride    QSACTLQTETHPSLTWQKCSSGGTCTQQTGSVVIDANWRWTHATNSSTNC
T. pseudokoningii   QSACTLQTETHPPLTWQKCSSGGTCTQQTGSVVIDANWRWTHATNSSTNC
T. koninlangbra     QSACTIQAETHPPLTWQKCSSGGSCTSQTGSVVIDANWRWTHATNSTTNC
T. harzanium        QQVCTQQAETHPPLTWQKCTASG-CTPQQGSVVLDANWRWTHDTKSTTNC
A. aculeatus        QQVGTYTAETHPSLTWQTCSGSGSCTTTSGSVVIDANWRWVHEVGGYTNC
A. niger            QQVGTYTTETHPSLTWQTCTSSGSCTTNDGAVVIDANWRWVHSTSSSTNC
P. janthinellum     QQVGTLTAETHPALTWSKCT-AGXCSQVSGSVVIDANWPXVHSTSGSTNC
H. grisea           QQACSLTTERHPSLSWKKCTAGGQCQTVQASITLDSNWRWTHQVSGSTNC
S. thermophilum     QQACSLTTERHPSLSWKKCTAGGQCQTVQASITLDSNWRWTHQVSGSTNC
P. anderina         QQVCSLTPESHPPLTWQRCSAGGSCTNVAGSVTLDSNWRWTHTLQGSTNC
                    *..  :  .* **.*:*. *: .* *     .::..:*:**  .*   . ***

51                                               100
                        |                                                 |
H. jecorina         YDGNTWSSTLCPDNETCAKNCCLDGAAYASTYGVTTSGNSLSIGFVTQSA
H. oriantalis       YDGNTWSSTLCPDNETCAKNCCLDGAAYASTYGVTTSADSLSIGFVTQSA
H. schweinitzii     YDGNTWSSTLCPDNETCAKNCCLDGAAYASTYGVTTSADSLSIGFVTQSA
T. citrinoviride    YDGNTWSSTLCPDNETCAKNCCLDGAAYASTYGVTTSADSLSIGFVTQSA
T. pseudokoningii   YDGNTWSSTLCPDNETCAKNCCLDGAAYASTYGVTTSADSLSIGFVTQSA
T. koninlangbra     YDGNTWSSSLCPDNESCAKNCCLDGAAYASTYGVTTSADSLSIGFVTQSQ
T. harzanium        YDGNTWSSTLCPDDATCAKNCCLDGANYSGTYGVTTSGDALTLQFVTAS-
A. aculeatus        YSGNTWDSSICSTDTTCASECALEGATYESTYGVTTSGSSLRLNFVTTAS
A. niger            YTGNEWDTSICTDDVTCAANCALDGATYEATYGVTTSGDELRLNFVTQGS
P. janthinellum     YTGNTWDATLCPDDVTCAANCAVDGARRQHLR-VTTSGNSLRINFVTTAS
H. grisea           YTGNKWDTSICTDAKSCAQNCCVDGADYTSTYGITTNGDSLSLKFVTKGQ
S. thermophilum     YTGNEWDSSICTDAKSCAQNCCVDGADYTSTYGITTNGDSLSLKFVTKGQ
P. anderina         YSGNEWDTSICTTGTKCAQNCCVEGAEYAATYGITTSGNQLNLKFVTEGK
                    *  ** *.:::*.        .** :*.::**       :**... *  : *** .

101                                              149
                        |                                                 |
H. jecorina         -QKNVGARLYLMASDTTYQEFTLLGNEFSFDVDVSQLPCGLNGALYFVSM
H. oriantalis       -QKNVGARLYLMASDTTYQEFTLLGNEFSFDVDVSQLPCGLNGALYFVSM
H. schweinitzii     -QKNVGARLYLMASDTTYQEFTLLGNEFSFDVDVSQLPCGLNGALYFVSM
T. citrinoviride    -QKNVGARLYLMASDTTYQEFTLLGNEFSFDVDVSQLPCGLNGALYFVSM
T. pseudokoningii   -QKNVGARLYLMASDTTYQEFTLLGNEFSFDVDVSQLPCGLNGALYFVSM
T. koninlangbra     -QKNVGARLYLMASDTTYQEFTLLGNEFSFDVDVSQLPCGLNGALYFVSM
T. harzanium        ---NVGSRLYLMANDSTYQEFTLSGNEFSFDVDVSQLPCGLNGALYFVSM
A. aculeatus        -QKNIGSRLYLLADDSTYETFKLFNREFTFDVDVSNLPCGLNGALYFVSM
A. niger            -SKNIGSRLYLMSDDSTYEMFKLLGQEFTFDVDVSNLPCGLNGALYFVAM
P. janthinellum     -QKNIGSRLYLLENDTTYQKFNLLNQEFTFDVDVSNLPCGLNGALYFVDM
H. grisea           HSTNVGSRTYLMDGEDKYQTFELLGNEFTFDVDVSNIGCGLNGALYFVSM
S. thermophilum     YSTNVGSRTYLMDGEDKYQTFELLGNEFTFDVDVSNIGCGLNGALYFVSM
P. anderina         YSTNVGSRTYLMENATKYQGFNLLGNEFTFDVDVSNIGCGLNGALYFVSM
                        *:*:* **:   .  .*: * *  ..**:*****::: ********** *
```

FIG. 2A

```
                           150                                              199
                           |                                                |
         H. jecorina       DADGGVSKYPTNTAGAKYGTGYCDSQCPRDLKFINGQANVEGWEPSSNNA
         H. oriantalis     DADGGVSKYPTNTAGAKYGTGYCDSQCPRDLKFINGQANVEGWEPSSNNA
         H. schweinitzii   DADGGVSKYPTNTAGAKYGTGYCDSQCPRDLKFINGQANVEGWEPSSNNA
         T. citrinoviride  DADGGVSKYPTNTAGAKYGTGYCDSQCPRDLKFINGQANVEGWEPSSNNA
         T. pseudokoningii DADGGVSKYPTNTAGAKYGTGYCDSQCPRDLKFINGEANVEGWEPFSNNA
         T. koninlangbra   DADGGVSKYPSNTAGAKYGTGYCDSQCPRDLKFINGEANVEGWEPASNNA
         T. harzanium      DADGGQSKYPGNAAGAKYGTGYCDSQCPRDLKFINGQANVEGWEPSSNNA
         A. aculeatus      DADGGVSRFPTNKAGAKYGTGYCDSQCPRDLKFIDGQANIEGWEPSSTDV
         A. niger          DADGGTSEYSGNKAGAKYGTGYCDSQCPRDLKFINGEANCDGWEPSSNNV
         P. janthinellum   DADGGMAKYPTNKAGAKYGTGYCDSQCPRDLKFINGQANVDGWTPSKNDV
         H. grisea         DADGGLSRYPGNKAGAKYGTGYCDAQCPRDIKFINGEANIEGWTGSTNDP
         S. thermophilum   DADGGLSRYPGNKAGAKYGTGYCDAQCPRDIKFINGEANIEGWTGSTNDP
         P. anderina       DLDGGLAKYSGNKAGAKYGTGYCDAQCPRDIKFINGEANIEGWNPSTNDV
                           *  ***  :.:. * ************:*****:***:*:**  :**    ..:

200                                          248
                           |                                            |
         H. jecorina       NTGIGGHGSCCSEMDIWEANSISEALTPHPCTTVGQEICEGDGCGGTYS-
         H. oriantalis     NTGIGGHGSCCSEMDIWEANSISEALTPHPCTTVGQEICDGDGCGGTYS-
         H. schweinitzii   NTGIGGHGSCCSEMDIWEANSISEALTPHPCTNVGQEICDGDGCGGTYS-
         T. citrinoviride  NTGIGGHGSCCSEMDIWXANSISEALTPHPCTTVGQEICEGDGCGGTYS-
         T. pseudokoningii NTGIGGHGSCCSEMDIWEANSISEALTPHPCTTVGQEICDGDSCGGTYS-
         T. koninlangbra   NTGIGGHGSCCSEMDIWEANSISEALTPHPCTTVGQAICDGDGCGGTYS-
         T. harzanium      NTGVGGHGSCCSEMDIWEANSISEALTPHPCETVGQTMCSGDSCGGTYS-
         A. aculeatus      NAGTGNHGSCCPEMDIWEANSISSAFTAHPCDSVQQTMCTGDTCGGTYSD
         A. niger          NTGVGDHGSCCPEMDIWEANSISNAFTAHPCDSVSQTMCDGDSCGGTYSA
         P. janthinellum   NSGIGNHGSCCAEMDIWEANSISNAVTPHPCDTPSQTMCTGQRCGGTYS-
         H. grisea         NAGAGRYGTCCSEMDIWEANNMATAFTPHPCTIIGQSRCEGDSCGGTYS-
         S. thermophilum   NAGAGRYGTCCSEMDIWEANNMATAFTPHPCTIIGQSRCEGDSCGGTYS-
         P. anderina       NAGAGRYGTCCSEMDIWEANNMATAYTPHSCTILDQSRCEGESCGGTYS-
                           *:*  *  :*:**.***** **.:: *  *.*.*     *   * *: ******

249                                         291
                           |                                           |
         H. jecorina       -DNRYGGTCDPDGCDWNPYRLGNTSFYGPG------SSFTLDTTKKLTVV
         H. oriantalis     -NDRYGGTCDPDGCDWNPYRLGNTSFYGPG------SSFTLDTTKKLTVV
         H. schweinitzii   -NDRYGGTCDPDGCDWNPYRLGNTSFYGPG------SSFTLDTTKKLTVV
         T. citrinoviride  -NDRYGGTCDPDGCDWNPYRLGNTSFYGPG------SSFTLDTTKKLTVV
         T. pseudokoningii -GDRYGGTCDPDGCDWNPYRLGNTSFYGPG------SSFALDTTKKLTVV
         T. koninlangbra   -DDRYGGTCDPDGCDWNPYRLGNTSXYGPG------SSFTLDTTKKMTVV
         T. harzanium      -NDRYGGTCDPDGCDWNPYRLGNTSFYGPG------SSFALDTTKKLTVV
         A. aculeatus      TIDRYSGTCDPDGCDFNPYRFGNTNFYGPGKTVDNSKPFTVVTQFITHDG
         A. niger          SGDRYSGTCDPDGCDYNPYRLGNTDFYGPGLTVDTNSPFTVVTQFITDDG
         P. janthinellum   -IDRYGGTCDPDGCDFNPYRMGVTNFYGPGETIDTKSPFTVVTQFLTNDG
         H. grisea         -NERYAGVCDPDGCDFNSYRQGNKTFYGKGMTVDTTKKITVVTQFLKD--
         S. thermophilum   -NDRYAGVCDPDGCDFNAYRQGNKTFYGKGMTVDTTKKLTVVTQFLKD--
         P. anderina       -SDRYGGVCDPDGCDFNSYRMGNKEFYGKGKTVDTTKKMTVVTQFLKN--
                           :**.*.*******:*.**  *   ** *          . ::: *
```

FIG. 2B

```
                        292                                             340
                         |                                               |
H. jecorina         TQFETSGAINRYYVQNGVTFQQPNAELGSYSG-NELNDDYCTAEEAEFGG
H. oriantalis       TQFETSGAINRYYVQNGVTYQQPNAELGSYSG-NELNDDYCTAEEESEFGG
H. schweinitzii     TQFETSGAINRYYVQNGVTYQQPNAELGSYSG-NELNDAYCTAEEESEFGG
T. citrinoviride    TQFETSGAINRYYVQNGVTYKQPNAELGSYSG-NELNDDYCTAEEESEFGG
T. pseudokoningii   TQFETSGAINRYYVQNGVTFQQPNAELGSYSG-NSLDDDYCAAEEAEFGG
T. koninlangbra     TQFATSGAINRYYVQNGVTFQQPNAELGSYSG-NTLNDAYCAAEEAEFGG
T. harzanium        TQFATDGSISRYYVQNGVKFQQPNAQVGSYSG-NTINTDYCAAEQTAFGG
A. aculeatus        TDTGTLTEIRRLYVQNGVVIGNGPSTYTAASG-NSITESFCKAEKTLFGD
A. niger            TSSGTLTEIKRLYVQNGEVIANGASTYSSVNG-SSITSDFCESEKTLFGD
P. janthinellum     TSTGTLSEIKRFYVQGGKVIGNPQSTIVGVSG-NSITDSWCNAQKSAFGD
H. grisea           -ANGDLGEIKRFYVQDGKIIPNSESTIPGVEG-NSITQDWCDRQKVAFGD
S. thermophilum     -ANGDLGEIKRFYVQDGKIIPNSESTIPGVEG-NSITQDWCDRQKVAFGD
P. anderina         -AAGELSEIKRFYVQNGVVIPNSVSSIPGVPNQNSITQDWCDAQKIAFGD
                     *  *  ***.*       :    :   .  . .:    :*   ::   **.

341                                             389
                         |                                               |
H. jecorina         SS-FSDKGGLTQFKKATSGGMVLVMSLWDDYYANMLWLDSTYPTNETSST
H. oriantalis       SS-FSDKGGLTQFKKATSGGMVLVMSLWDDYYANMLWLDSTYPTNETSST
H. schweinitzii     SS-FSDKGGLTQFKKATSGGMVLVMSLWDDYYANMLWLDSTYPTNETSST
T. citrinoviride    SS-FSDKGGLTQFKKATSGGMVLVMSLWDDYYANMLWLDSTYPTNETSST
T. pseudokoningii   SS-FSDKGGLTQFKKATSGGMVLVMSLWDDYYANMLWLDSTYPTNETSST
T. koninlangbra     SS-FSDKGGLTQFKQATSGGMVLVMSLWDDYYANMLWLDSIYPTNETSST
T. harzanium        TS-FTDKGGLAQINKAFQGGMVLVMSLWDDYAVNMLWLDSTYPTNATAST
A. aculeatus        TNVFETHGGLSAMGDALGDGMVLVLSLWDDHAADMLWLDSDYPTTSCASS
A. niger            ENVFDTHGGLAGMGEAMANGMVLVLSLWDDYAANMLWLDSDYPVNSSAST
P. janthinellum     TNEFSKHGGMAGMGAGLADGMVLVMSLWDDHASDMLWLDSTYPTNATSTT
H. grisea           IDDFNRKGGMKQMGKALAGPMVLVMSIWDDHASNMLWLDSTFPVDA-AGK
S. thermophilum     IDDFNRKGGMKQMGKALAGPMVLVMSIWDDHASNMLWLDSTFPVDA-AGK
P. anderina         PDDNTAKGGLRQMGLALDKPMVLVMSIWNDHAAHMLWLDSTYPVDA-AGR
                      .   :**:    :   .    ****:*:*:*:  .****** :*.    :

390                                             439
                         |                                               |
H. jecorina         PGAVRGSCSTSSGVPAQVESQSPNAKVTFSNIKFGPIGSTGNPSGGNPPG
H. oriantalis       PGAVRGSCSTSSGVPAQLESQSPNAKVVYSNIKFGPIGSTGNPSGGNPPG
H. schweinitzii     PGAVRGSCSTSSGVPAQLESQSANAKVVYSNIKFGPIGSTGNPSGGNPPG
T. citrinoviride    PGAVRGSCSTSSGVPAQLESQSPNAKVVYSNIKFGPIGSTGNPSGGNPPG
T. pseudokoningii   PGAVRGSCSTSSGVPAQLESQSTNAKVVYSNIKFGPIGSTGNSSGGSPPG
T. koninlangbra     PGAARGSCSTSSGVPAQLESQSTNAKVVFSNIKFGPIGSTGNSSGGNPPG
T. harzanium        PGAKRGSCSTSSGVPAQVEAQSPNSKVIYSNIRFGPIGSTGGNTGSNPPG
A. aculeatus        PGVARGTCPTTTGNATYVEANYPNSYVTYSNIKFGTLNSTYSGTSSGGSS
A. niger            PGVARGTCSTDSGVPATVEADSPNAYVTYSNIKFGPIGSTYSSGSSSGSG
P. janthinellum     PGAKRGTCDI-SRRPNTVESTYPNAYVIYSNIKTGPLNSTFTGGTTSSSS
H. grisea           PGAERGACPTTSGVPAEVEAEAPNSNVVFSNIRFGPIGSTVAGLPGAGNG
S. thermophilum     PGAERGACPTTSGVPAEVEAEAPNSNVVFSNIRFGPIGSTVAGLPSDGGN
P. anderina         PGAERGACPTTSGVPSEVEAEAPNSNVAFSNIKFGPIGSTFNSGSTNPNP
                    **. **:*     :   .  .*:   .*: *  :***: *.:..**
```

FIG. 2C

```
                        440                                           475
                        |                                             |
H. jecorina             GNPP--------------GTTTTRRPATTTGSSPGPTQSHYGQCGGIGYS
H. oriantalis           GNPP--------------GTTTTRRPATTTGSSPGPTQTHYGQCGGIGYS
H. schweinitzii         GNPP--------------GTTTTRRPATTTGSSPGPTQTHYGQCGGIGYS
T. citrinoviride        GNPP--------------GTTTTRRPATTTGSSPGPTQTHYGQCGGIGYS
T. pseudokoningii       GGNPP-------------GTTTTRRPATSTGSSPGPTQTHYGQCGGIGYS
T. koninlangbra         GGNPP-------------GTTTTRRPATTTGSSPGPTQTHYGQCGGIGYS
T. harzanium            TSTT------------------RAPPSSTGSSPTATQTHYGQCGGTGWT
A. aculeatus            SSSTTLTTKASTSTTSS-KTTTTTSKTSTTSSSSTNVAQLYGQCGGQGWT
A. niger                SSSSSSSTTTKATSTTL-KTTTTTS----SGSSSTSAAQAYGQCGGQSWT
P. janthinellum         TTTTTSKSTSTSSSSKT-TTTVTTT--TTSSGSSGTGARDWAQCGGNGWT
H. grisea               GNNGGNPPPPTTTTS--------SAPATTTTASAGPKAGRWQQCGGIGFT
S. thermophilum         NGGNTTVQPPPSTTTTSASSSTTSAPATTTTASAGPKAGRWQQCGGIGFT
P. anderina             ISSSTATTPTSTRVSS------TSTAAQTPTSAPGGTVPRWGQCGGQGYT
                                  . .:.         : ****  .::

476              497
                        |                |
H. jecorina             GPTVCASGTTCQVLNPYYSQCL
H. oriantalis           GPTVCASGTTCQVLNPYYSQCL
H. schweinitzii         GPTICASGTTCQVLNPYYSQCL
T. citrinoviride        GPTVCASGTTCQVLNEYYSQCL
T. pseudokoningii       GPTVCASGSTCQVLNPYYSQCL
T. koninlangbra         GPTVCASGSTCQVLNPYYSQCL
T. harzanium            GPTRCASGYTCQVLNPFYSQCL
A. aculeatus            GPTTCASG-TCTKQNDYYSQCL
A. niger                GPTTCVSGYTCTYQNAYYSQCL
P. janthinellum         GPTTCVSPYTCTKQNDWYSQCL
H. grisea               GPTQCEEPYTCTKLNDWYSQCL
S. thermophilum         GPTQCEEPYTCTKLNDWYSQCL
P. anderina             GPTQCVAPYTCVVSNQWYSQC-
                        *** *    **  *  :****
```

FIG. 2D

VARIANTS OF CELLOBIOHYDROLASES

CROSS REFERENCE TO RELATED APPLICATIONS

This application is the National Stage application of international application no. PCT/US2013/074005, filed on 10 Dec. 2013, which claims benefit of priority from U.S. provisional patent application No. 61/736,315, filed on 12 Dec. 2012, both of which are incorporated herein by reference in their entireties.

GOVERNMENT RIGHTS

This invention was made with government support under grant number DE-FC36-08GO18078 awarded by the U.S. Department of Energy. The government has certain rights in this invention.

SEQUENCE LISTING

The content of the electronically submitted sequence listing in ASCII text (File Name: NB40236USPCT_SeqList_ST25 Size: 64,677 bytes, and date of creation Dec. 18, 2015) is incorporated herein by reference in its entirety.

FIELD OF THE INVENTION

The present disclosure generally relates to glycoside hydrolase enzyme variants, particularly variants of cellobiohydrolase (CBH). Nucleic acids encoding the CBH variants, compositions including the CBH variants, methods of producing the CBH variants, and methods of using the variants are also described.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., 1987; Shulein, 1988). Endoglucanases act mainly on the amorphous parts of the cellulose fiber, whereas cellobiohydrolases are also able to degrade crystalline cellulose (Nevalainen and Penttila, 1995). Thus, the presence of a cellobiohydrolase in a cellulase system is required for efficient solubilization of crystalline cellulose (Suurnakki, et al. 2000). Beta-glucosidase acts to liberate D-glucose units from cellobiose, cellooligosaccharides, and other glucosides (Freer, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. (See, e.g., Aro et al., 2001; Aubert et al., 1988; Wood et al., 1988, and Coughlan, et al.)

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, i.e., CBH I and CBH II, at least 8 EGs, i.e., EG I, EG II, EG III, EGIV, EGV, EGVI, EGVII and EGVIII, and at least 5 BGs, i.e., BG1, BG2, BG3, BG4 and BG5.

In order to efficiently convert crystalline cellulose to glucose the complete cellulase system comprising components from each of the CBH, EG and BG classifications is required, with isolated components less effective in hydrolyzing crystalline cellulose (Filho et al., 1996). A synergistic relationship has been observed amongst cellulase components from different classifications. In particular, the EG-type cellulases and CBH-type cellulases synergistically interact to more efficiently degrade cellulose. (See, e.g., Wood, 1985.)

Cellulases are known in the art to be useful in the treatment of textiles for the purposes of enhancing the cleaning ability of detergent compositions, for use as a softening agent, for improving the feel and appearance of cotton fabrics, and the like (Kumar et al., 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hammamatsu Textile Industrial Research Institute Report, Vol. 24, pp. 54-61, 1986), have been described.

Cellulases are further known in the art to be useful in the conversion of cellulosic feedstocks into ethanol. This process has a number of advantages, including the ready availability of large amounts of feedstock that is otherwise discarded (e.g., burning or land filling the feedstock). Other materials that consist primarily of cellulose, hemicellulose, and lignin, e.g., wood, herbaceous crops, and agricultural or municipal waste, have been considered for use as feedstock in ethanol production.

It would be an advantage in the art to provide cellobiohydrolase (CBH) variants with improved properties for converting cellulosic materials to monosaccharides, disaccharides, and polysaccharides. Improved properties of the variant CBH include, but are not limited to: altered temperature-dependent activity profiles, thermostability, pH activity, pH stability, substrate specificity, product specificity, and chemical stability.

BRIEF SUMMARY OF THE INVENTION

The present disclosure describes isolated variant cellobiohydrolase (CBH) enzymes having cellulase activity, nucleic acids encoding such CBH enzymes, host cells containing CBH enzyme-encoding polynucleotides (e.g., host cells that express the CBH enzymes), compositions containing the CBH enzyme, and methods for producing and using the same.

As such, aspects of the present invention provide variants of a parent CBH enzyme, where the variant has cellulase activity, has at least 80% sequence identity to SEQ ID NO:3, and has at least one improved property over the parent CBH enzyme selected from: (a) expression (Protein Content Determination), (b) PASC Hydrolysis Assay, (c) PASC Hydrolysis Assay in the Presence of EG2, (d) PASC Hydrolysis Assay After Heat Incubation, (e) Whole Hydrolysate PCS (whPCS) Assay, (f) Dilute Ammonia Corn Cob (daCC) Assay, and (g) dilute ammonia corn stover (daCS) assay.

In certain embodiments, a CBH variant has at least two, at least three, at least four, at least five, or more improved properties selected from the list above over the parent CBH.

In certain embodiments, a CBH variant has one or more highly combinable substitutions that fall into Group A as defined herein (see Examples section below).

In certain embodiments, a CBH variant has one or more highly combinable substitutions that fall into Group B as defined herein, where the variant further may have one or more amino acid substitutions that fall into Group A.

In certain embodiments, a CBH variant has one or more highly combinable substitutions that fall into Group C as defined herein, where the variant further may have one or more amino acid substitutions that fall into Group A or Group B.

In certain embodiments, the CBH variant has an amino acid substitution at at least one site that has a productivity score of 4 as defined herein (see Examples section below and Table 4).

In certain embodiments, the CBH variant has an amino acid substitution at at least one site that has a productivity score of 3, where the variant further may have at least one additional substitution at a site that has a productivity score of 4.

In certain embodiments, the CBH variant has an amino acid substitution at at least one site that has a productivity score of 2, where the variant further may have at least one additional substitution at a site that has a productivity score of 3 or 4.

In certain embodiments, the CBH variant has an amino acid substitution at at least one site that has a productivity score of 1, where the variant further may have at least one additional substitution at a site that has a productivity score of 2 or 3 or 4.

In certain embodiments, the CBH variant has at least one amino acid substitution that has a variant suitability score of +++++ as defined herein (see Examples section below and Table 4).

In certain embodiments, the CBH variant has at least one amino acid substitution that has a variant suitability score of ++++, where the variant further may have at least one additional substitution that has a variant suitability score of +++++.

In certain embodiments, the CBH variant has at least one amino acid substitution that has a variant suitability score of +++, where the variant further may have at least one additional substitution that has a variant suitability score of ++++ or +++++.

In certain embodiments, the CBH variant has at least one amino acid substitution that has a variant suitability score of ++, where the variant further may have at least one additional substitution that has a variant suitability score of +++ or ++++ or +++++.

In certain embodiments, the CBH variant has at least one amino acid substitution that has a variant suitability score of +, where the variant further may have at least one additional substitution that has a variant suitability score of ++ or +++ or ++++ or +++++.

In certain embodiments, the CBH variant has at least one amino acid substitution that falls into one of the specific productivity score/variant suitability score categories A to T as set forth in Table 1 below:

TABLE 1

| CBH Varian Categories | | | | | | |
|---|---|---|---|---|---|---|
| | | Variant Suitability Score | | | | |
| | | +++++ | ++++ | +++ | ++ | + |
| Productivity Score | 4 | A | B | C | D | E |
| | 3 | F | G | H | I | J |
| | 2 | K | L | M | N | O |
| | 1 | P | Q | R | S | T |

The specific amino acid positions and substitutions for each category can be readily identified in Table 4 of Example 3 herein. For example, a CBH variant can have at least one substitutions selected from the following, each of which falls into category A: A414F, G22Q, G22M, G22K, G22S, G394R, R394D, R394V, T417Y, T417S, and T417Q.

Examples of CBH variants include, but are not limited to the following:

1. A CBH variant having at least one amino acid substitution at a position selected from the group consisting of: A414, G22, R394, T417, P227, T255, V403, F280, E337, P258, T332, T296, N49, Y493, S196, G430, T246, Y247, N307, T356, Y466, S357, Q27, S387, L318, T389, Y303, Y370, K287, T285, N350, D249, F338, S113, Y492, S398, T226, Y371, A316, K346, G340, S342, D368, M374, D179, E236, Y474, G391, F418, F311, R251, T281, V104, L326, A224, and E385, where the position of each amino acid substitution corresponds to SEQ ID NO:3.
2. The CBH variant as set forth in 1 above where the at least one amino acid substitution is selected from Table 4.
3. The CBH variant as set forth in any one of 1 or 2 above and having an amino acid substitution at position A414 selected from the group consisting of: F, N, L, M, W, R, G, K, I, H, Q, D, C, and T.
4. The CBH variant as set forth in any one of 1 to 3 above and having an amino acid substitution at position G22 selected from the group consisting of: D, E, H, P, T, F, C, A, W, L, Y, I, Q, M, K, and S.
5. The CBH variant as set forth in any one of 1 to 4 above and having an amino acid substitution at position R394 selected from the group consisting of: E, P, Y, F, W, Q, L, N, T, M, C, A, I, S, G, R, D, and V.
6. The CBH variant as set forth in any one of 1 to 5 above and having an amino acid substitution at position T417 selected from the group consisting of: W, L, I, F, E, D, K, R, H, A, T, V, Y, S, and Q.
7. The CBH variant as set forth in any one of 1 to 6 above and having an amino acid substitution at position P227 selected from the group consisting of: I, W, M, V, E, T, L, A, and C.
8. The CBH variant as set forth in any one of 1 to 7 above and having an amino acid substitution at position T255 selected from the group consisting of: E, F, L, S, W, P, D, I, N, Q, C, R, V, and K.

9. The CBH variant as set forth in any one of 1 to 8 above and having an amino acid substitution at position V403 selected from the group consisting of: T, Y, N, E, D, M, I, K, R, and V.

10. The CBH variant as set forth in any one of 1 to 9 above and having an amino acid substitution at position F280 selected from the group consisting of: I, H, D, N, V, W, E, F, and S.

11. The CBH variant as set forth in any one of 1 to 10 above and having an amino acid substitution at position E337 selected from the group consisting of: C, V, G, Q, R, I, M, S, and W.

12. The CBH variant as set forth in any one of 1 to 11 above and having an amino acid substitution at position P258 selected from the group consisting of: R, I, K, G, M, H, N, S, L, Q, and A.

13. The CBH variant as set forth in any one of 1 to 12 above and having an amino acid substitution at position T332 selected from the group consisting of: S, M, C, Y, K, Q, R, and A.

14. The CBH variant as set forth in any one of 1 to 13 above and having an amino acid substitution at position T296 selected from the group consisting of: T, D, E, Y, N, F, K, W, A, S, and L.

15. The CBH variant as set forth in any one of 1 to 14 above and having an amino acid substitution at position N49 selected from the group consisting of: M, Q, L, G, E, D, A, S, and P.

16. The CBH variant as set forth in any one of 1 to 15 above and having an amino acid substitution at position Y493 selected from the group consisting of: E, K, N, D, I, A, V, and F.

17. The CBH variant as set forth in any one of 1 to 16 above and having an amino acid substitution at position S196 selected from the group consisting of: D, V, E, F, A, K, G, R, L, P, M, and I.

18. The CBH variant as set forth in any one of 1 to 17 above and having an amino acid substitution at position G430 selected from the group consisting of: N, Q, S, A, R, L, M, C, D, I, and T.

19. The CBH variant as set forth in any one of 1 to 18 above and having an amino acid substitution at position T246 selected from the group consisting of: K, L, M, E, W, N, R, I, Q, T, F, P, and S.

20. The CBH variant as set forth in any one of 1 to 19 above and having an amino acid substitution at position Y247 selected from the group consisting of: Q, T, M, W, D, and F.

21. The CBH variant as set forth in any one of 1 to 20 above and having an amino acid substitution at position N307 selected from the group consisting of: E, R, A, C, D, and H.

22. The CBH variant as set forth in any one of 1 to 21 above and having an amino acid substitution at position T356 selected from the group consisting of: M, I, and L.

23. The CBH variant as set forth in any one of 1 to 22 above and having an amino acid substitution at position Y466 selected from the group consisting of: R, C, V, and S.

24. The CBH variant as set forth in any one of 1 to 23 above and having an amino acid substitution at position S357 selected from the group consisting of: A, G, T, R, and V.

25. The CBH variant as set forth in any one of 1 to 24 above and having an amino acid substitution at position Q27 selected from the group consisting of: A, E, K, V, T, and I.

26. The CBH variant as set forth in any one of 1 to 25 above and having an amino acid substitution at position S387 selected from the group consisting of: K, I, W, G, D, V, and A.

27. The CBH variant as set forth in any one of 1 to 26 above and having an amino acid substitution at position L318 selected from the group consisting of: I, V, and C.

28. The CBH variant as set forth in any one of 1 to 27 above and having an amino acid substitution at position T389 selected from the group consisting of: S, H, V, and D.

29. The CBH variant as set forth in any one of 1 to 28 above and having an amino acid substitution at position Y303 selected from the group consisting of: W, L, and F.

30. The CBH variant as set forth in any one of 1 to 29 above and having an amino acid substitution at position Y370 selected from the group consisting of: R, Q, L, G, and F.

31. The CBH variant as set forth in any one of 1 to 30 above and having an amino acid substitution at position K287 selected from the group consisting of: E, Y, D, and N.

32. The CBH variant as set forth in any one of 1 to 31 above and having an amino acid substitution at position T285 selected from the group consisting of: R, C, K, and Q.

33. The CBH variant as set forth in any one of 1 to 32 above and having an amino acid substitution at position N350 selected from the group consisting of: K, D, Q, L, and I.

34. The CBH variant as set forth in any one of 1 to 33 above and having an amino acid substitution at position D249 selected from the group consisting of: A, Q, and S.

35. The CBH variant as set forth in any one of 1 to 34 above and having an amino acid substitution at position F338 selected from the group consisting of: D, L, and R.

36. The CBH variant as set forth in any one of 1 to 35 above and having an amino acid substitution at position S113 selected from the group consisting of: G, E, N, and T.

37. The CBH variant as set forth in any one of 1 to 36 above and having an amino acid substitution at position Y492 selected from the group consisting of: M, H, A, and F.

38. The CBH variant as set forth in any one of 1 to 37 above and having an amino acid substitution at position S398 selected from the group consisting of: A, D, and P.

39. The CBH variant as set forth in any one of 1 to 38 above and having an amino acid substitution at position T226 selected from the group consisting of: G, A, C, D, V, and S.

40. The CBH variant as set forth in any one of 1 to 39 above and having an amino acid substitution at position Y371 selected from the group consisting of: Y and W.

41. The CBH variant as set forth in any one of 1 to 40 above and having an amino acid substitution at position A316 selected from the group consisting of: I and C.

42. The CBH variant as set forth in any one of 1 to 41 above and having a K346H amino acid substitution.

43. The CBH variant as set forth in any one of 1 to 42 above and having a G340D amino acid substitution.

44. The CBH variant as set forth in any one of 1 to 43 above and having a S342C amino acid substitution.

45. The CBH variant as set forth in any one of 1 to 44 above and having a D368C amino acid substitution.

46. The CBH variant as set forth in any one of 1 to 45 above and having a M374C amino acid substitution.

47. The CBH variant as set forth in any one of 1 to 46 above and having an E236D amino acid substitution.

48. The CBH variant as set forth in any one of 1 to 47 above and having an amino acid substitution at position Y474 selected from the group consisting of: K, and W.

49. The CBH variant as set forth in any one of 1 to 48 above and having a G391Y amino acid substitution.

50. The CBH variant as set forth in any one of 1 to 49 above and having a F418Y amino acid substitution.
51. The CBH variant as set forth in any one of 1 to 50 above and having an amino acid substitution at position F311 selected from the group consisting of: Y and V.
52. The CBH variant as set forth in any one of 1 to 51 above and having an R251A amino acid substitution.
53. The CBH variant as set forth in any one of 1 to 52 above and having a T281D amino acid substitution.
54. The CBH variant as set forth in any one of 1 to 53 above and having an amino acid substitution at position V104 selected from the group consisting of: F and H.
55. The CBH variant as set forth in any one of 1 to 54 above and having an L326I amino acid substitution.
56. The CBH variant as set forth in any one of 1 to 55 above and having an A224Q amino acid substitution.
57. The CBH variant as set forth in any one of 1 to 56 above and having an E385Y amino acid substitution.
58. The CBH variant as set for the in any one of 1 to 57 above and further including an additional amino acid mutation at one or both amino acid positions corresponding to S92 and T41 of SEQ ID NO:3.
59. The CBH variant of 58 above where the additional amino acid mutation is a substitution selected from S92T and T41I.
60. The CBH variant of 59 above having a S92T substitution.
61. The CBH variant of 59 or 60 above having a T41I substitution.

In certain embodiments, the parent CBH is a fungal cellobiohydrolase 1 (CBH1), e.g., a CBH1 from *Hypocrea jecorina, Hypocrea orientalis, Hypocrea schweinitzii, Trichoderma citrinoviride; Trichoderma pseudokoningii; Trichoderma konilangbra, Trichoderma harzanium, Aspergillus aculeatus, Aspergillus niger; Penicillium janthinellum, Humicola grisea, Scytalidium thermophilum,* and *Podospora anderina* (or their respective anamorph, teleomorph or holomorph counterpart forms), e.g., a CBH1 selected from any one of SEQ ID NOs: 3 to 15. In certain embodiments, the parent CBH has at least 90% sequence identity to SEQ ID NO:3, e.g., at least 95% sequence identity.

Aspects of the subject invention include an isolated polynucleotide comprising a polynucleotide sequence encoding a variant of a parent CBH as described herein. The isolated polynucleotide may be present in a vector, e.g., an expression vector or a vector for propagation of the polynucleotide. The vector may be present in a host cell to propagate the vector and/or that expresses the encoded CBH variant as described herein. The host cell can be any cell that finds use in propagation of the CBH variant polynucleotide and/or expression of the encoded CBH variant, e.g., a bacterial cell, a fungal cell, etc. Examples of suitable fungal cell types that can be employed include filamentous fungal cells, e.g., cells of *Trichoderma reesei, Trichoderma longibrachiatum, Trichoderma viride, Trichoderma koningii, Trichoderma harzianum, Penicillium, Humicola, Humicola insolens, Humicola grisea, Chrysosporium, Chrysosporium lucknowense, Myceliophthora thermophila, Gliocladium, Aspergillus, Fusarium, Neurospora, Hypocrea, Emericella, Aspergillus niger, Aspergillus awamori, Aspergillus aculeatus,* and *Aspergillus nidulans*. Alternatively, the fungal host cell can be a yeast cell, e.g., *Saccharomyces cervisiae, Schizzosaccharomyces pombe, Schwanniomyces occidentalis, Kluveromyces lactus, Candida utilis, Candida albicans, Pichia stipitis, Pichia pastoris, Yarrowia lipolytica, Hansenula polymorpha, Phaffia rhodozyma, Arxula adeniniv-* *orans, Debaryomyces hansenii,* or *Debaryomyces polymorphus*. In a particular aspect, a suitable host cell may even be one that is an ethanologen microorganism, including, for example, an engineered *Zymomonas mobilis* or a yeast ethanologen.

Aspects of the present invention include methods of producing a variant CBH that includes culturing a host cell that contains a polynucleotide encoding the CBH variant in a suitable culture medium under suitable conditions to express (or produce) the CBH variant from the polynucleotide, e.g., where the polynucleotide encoding the CBH variant is present in an expression vector (i.e., where the CBH variant-encoding polynucleotide is operably linked to a promoter that drives expression of the CBH variant in the host cell). In certain embodiments, the method further includes isolating the produced CBH variant.

Aspects of the present invention also include compositions containing a CBH variant as described herein. Examples of suitable compositions include, but are not limited to detergent compositions, feed additives, and compositions for treating (or hydrolyzing) a cellulosic substrate (e.g., a cellulose containing textile, e.g., denim; a cellulose containing biomass material, e.g., a mixture of lignocellulosic biomass material which has optionally been subject to pre-treatment of pre-hydrolysis processing, etc.). Compositions that include a CBH variant as described herein and a cellulosic substrate represent further aspects of the present invention. CHB variant-containing detergent compositions include laundry detergents and dish detergents, where such detergents may further include additional components, e.g., surfactants. Examples of suitable cellulosic substrates include, but are not limited to: grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, wood pulp, recycled wood pulp fiber, paper sludge, sawdust, hardwood, softwood, and combinations thereof.

Aspects of the present invention include methods for hydrolyzing a cellulosic substrate comprising contacting the substrate with a variant CBH as described herein. In certain embodiments, the CBH variant is provided as a cell-free composition, whereas in other embodiments, the CBH variant is provided as a host cell composition in which the host cell expresses the CBH variant. Thus, certain embodiments of the methods for hydrolyzing a cellulosic substrate contacting the substrate with a host cell containing a CBH variant expression vector. In certain embodiments, the method is for converting a lignocellulosic biomass to glucose, where in some of these embodiments, the lignocellulosic biomass is selected, without limitation, from: grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, wood pulp, recycled wood pulp fiber, paper sludge, sawdust, hardwood, softwood, and combinations thereof. In certain other embodiments, the cellulosic substrate is a cellulosic-containing textile, e.g., denim, where in some of these embodiments the method is for treating indigo dyed denim (e.g., in a stonewashing process).

Aspects of the present invention include cell culture supernatant compositions that contain a CBH variant as described herein. For example, a cell culture supernatant obtained by culturing a host cell that contains a polynucleotide encoding the CBH variant in a suitable culture medium under suitable conditions to express the CBH variant from the polynucleotide and secrete the CBH variant into the cell culture supernatant. Such a cell culture supernatant can include other proteins and/or enzymes produced by the host cell, including endogenously- and/or exogenously-expressed proteins and/or enzymes. Such supernatant of the culture medium can be used as is, with minimum or no post-production processing, which may typically include filtration to remove cell debris, cell-kill procedures, and/or ultrafiltration or other steps to enrich or concentrate the enzymes therein. Such supernatants are referred to herein as "whole broths" or "whole cellulase broths".

The CBH variants can be produced by co-expression with one or more other cellulases, and/or one or more hemicellulases. Alternatively, the CBH variants can be produced without other cellulases or hemicellulases. In the latter case, the CBH variant optionally can be physically mixed with one or more other cellulases and/or one or more hemicellulases to form an enzyme composition that is useful for a particular application, e.g., in hydrolyzing lignocellulosic biomass substrates.

Other compositions containing a desired variant cellulase, as well as methods for using such compositions, are also contemplated.

BRIEF DESCRIPTION OF THE DRAWINGS

FIGS. 1A and 1B show the nucleic acid sequence (top line) (SEQ ID NO:1) and amino acid sequence (bottom line) (SEQ ID NO:3) of the wild type Cel7A (CBH1) from *H. jecorina*.

FIGS. 2A, 2B, 2C and 2D show the amino acid alignment of the mature form of CBH enzymes derived from *Hypocrea jecorina* (SEQ ID NO:3), *Hypocrea orientalis* (SEQ ID NO:4), *Hypocrea schweinitzii* (SEQ ID NO:5), *Trichoderma citrinoviride* (SEQ ID NO:6); *Trichoderma pseudokoningii* (SEQ ID NO:7); *Trichoderma konilangbra* (SEQ ID NO:8), *Trichoderma harzanium* (SEQ ID NO:9), *Aspergillus aculeatus* (SEQ ID NO:10), *Aspergillus niger* (SEQ ID NO:11); *Penicillium janthinellum* (SEQ ID NO:12), *Humicola grisea* (SEQ ID NO:13), *Scytalidium thermophilum* (SEQ ID NO:14), and *Podospora anderina* (SEQ ID NO:15). The numbering at the top indicates the amino acid number of the mature form of *Hypocrea jecorina*. Identical, conserved, and semi-conserved amino acids are indicated with an asterisk (*), colon (:), and period (.), respectively.

DETAILED DESCRIPTION

Figure 3:
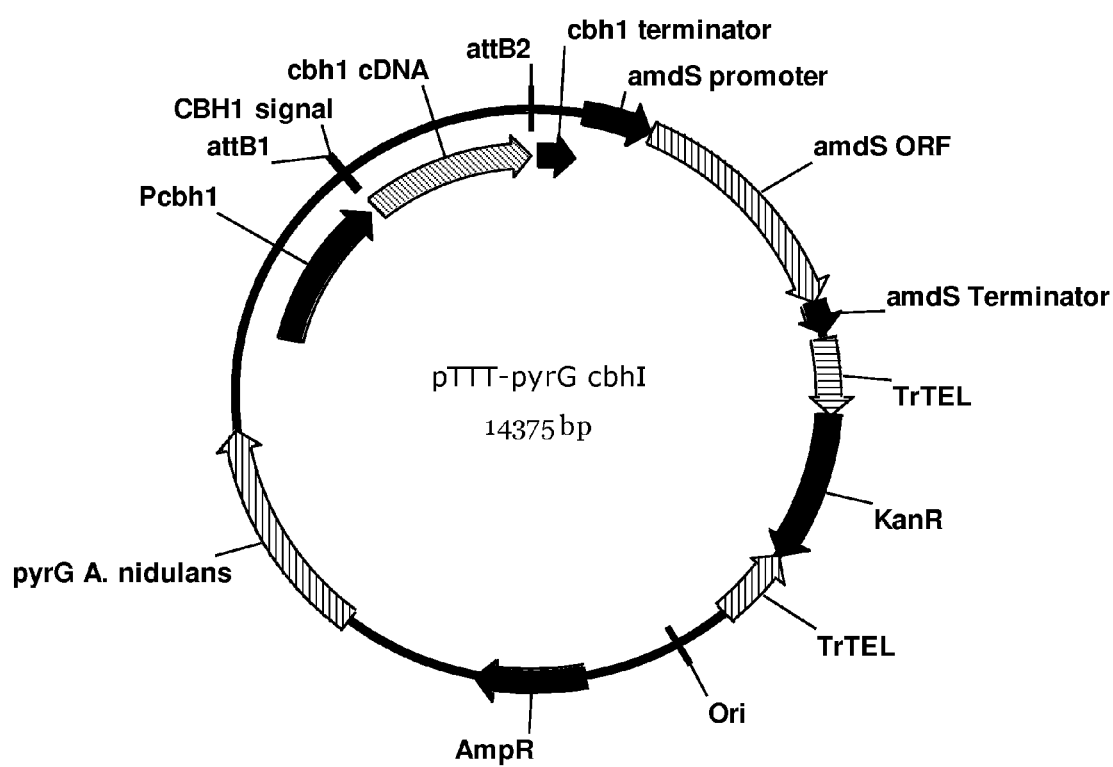
FIG. 3 is a schematic representation of the expression vector pTTT-pyrG-cbh1.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 3RD ED., John Wiley and Sons, Ltd., New York (2007), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation. Practitioners are particularly directed to Green and Sambrook *Molecular Cloning: A Laboratory Manual* (Fourth Edition), Cold Spring Harbor Laboratory Press 2012, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. As such, the present invention contemplates every possible variant nucleotide sequence encoding CBH or a variant thereof, all of which are possible given the degeneracy of the genetic code. Unless otherwise indicated, nucleic acid sequences are presented in 5'-to-3' orientation.

"Cellulase" or "cellulase enzyme" means bacterial or fungal exoglucanases or exocellobiohydrolases, and/or endoglucanases, and/or β-glucosidases. These three different types of cellulase enzymes are known to act synergistically to convert cellulose and its derivatives to glucose.

"Cellobiohydrolase" or "CBH" or "CBH enzyme" or "CBH polypeptide," as used herein is defined as a 1,4-D-glucan cellobiohydrolase (E.C. 3.2.1.91) which catalyzes the hydrolysis of 1,4-beta-D-glucosidic linkages in cellulose, cellotetriose, or any beta-1,4-linked glucose containing polymer, releasing cellobiose from the non-reducing ends of the chain. Cellobiohydrolase (CBH) activity is determined for purposes of the present invention according to the procedures described by Lever et al., 1972, Anal. Biochem. 47: 273-279 and variations thereof (see Examples section below), and/or by van Tilbeurgh et al., 1982, FEBS Letters, 149: 152-156.

A "variant" of an enzyme, protein, polypeptide, nucleic acid, or polynucleotide as used herein means that the variant is derived from a parent polypeptide or parent nucleic acid (e.g., native, wildtype or other defined parent polypeptide or nucleic acid) that includes at least one modification or alteration as compared to that parent. Alterations/modifications can include a substitution of an amino acid/nucleic acid residue in the parent for a different amino acid/nucleic acid residue at one or more sites, deletion of an amino acid/nucleic acid residue (or a series of amino acid/nucleic acid residues) in the parent at one or more sites, insertion of an amino acid/nucleic acid residue (or a series of amino acid/nucleic acid residues) in the parent at one or more sites, truncation of amino- and/or carboxy-terminal amino acid sequences or 5' and or 3' nucleic acid sequences, and any combination thereof. A variant CBH enzyme (sometimes referred to as a "CBH variant") according to aspects of the invention retains cellulase activity but may have an altered property in some specific aspect, e.g., an improved property. For example, a variant CBH enzyme may have an altered pH optimum, improved thermostability or oxidative stability, or a combination thereof, but will retain its characteristic cellulase activity.

"Combinatorial variants" are variants comprising two or more mutations, e.g., 2, 3, 4, 5, 6, 7, 8, 9, 10, or more, substitutions, deletions, and/or insertions.

A "parent CBH1 enzyme" or "parent CBH enzyme" or "parent CBH polypeptide" or equivalents thereto as used herein means a polypeptide that in its mature form comprises an amino acid sequence which has at least 80% identity with SEQ ID NO: 3, including amino acid sequences having at least 81%, 82%, 83%, 84%, 85%, 86%, 87%, 88%, 89%, 90%, 91%, 92%, 93%, 94%, 95%, 96%, 97%, 98%, 99%, or 100% identity with SEQ ID NO: 3, which provides the amino acid sequence of the mature form of wild type CBH1 from Hypocrea jecorina. It is further noted that the words "parent" and "parental" are used interchangeably in this context. In certain aspects, a parent CBH enzyme comprises the amino acid sequence of any one of SEQ ID NOs: 2 to 8, or an allelic variant thereof, or a fragment thereof that has cellulase activity. In certain embodiments, the parent CBH enzyme is from a filamentous fungus of the subdivision Eumycota or Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic. A filamentous fungal parent cell may be a cell of a species of, but not limited to, Trichoderma, e.g., Trichoderma longibrachiatum, Trichoderma viride, Trichoderma koningii, Trichoderma harzianum; Penicillium sp.; Humicola sp., including Humicola insolens and Humicola grisea; Chrysosporium sp., including C. lucknowense; Myceliophthora sp.; Gliocladium sp.; Aspergillus sp.; Fusarium sp., Neurospora sp., Hypocrea sp., e.g., Hypocrea jecorina, and Emericella sp. As used herein, the term "Trichoderma" or "Trichoderma sp." refers to any fungal strains which have previously been classified as Trichoderma or are currently classified as Trichoderma.

The term "wild-type" refers to a naturally-occurring polypeptide or nucleic acid sequence, i.e., one that does not include a man-made variation.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion polypeptide).

The term "recombinant" when used with reference, e.g., to a cell, or nucleic acid, polypeptide, or vector, indicates that the cell, nucleic acid, polypeptide or vector, has been modified by the introduction of a heterologous nucleic acid or polypeptide or the alteration of a native nucleic acid or polypeptide, or that the cell is derived from a cell so modified. Thus, for example, recombinant cells express genes that are not found within the native (non-recombinant) form of the cell or express native genes that are otherwise abnormally expressed, under expressed or not expressed at all.

The terms "isolated" or "purified" as used herein refer to a nucleic acid or polynucleotide that is removed from the environment in which it is naturally produced. In general, in an isolated or purified nucleic acid or polypeptide sample, the nucleic acid(s) or polypeptide(s) of interest are present at an increased absolute or relative concentration as compared to the environment in which they are naturally produced.

The term "enriched" when describing a component or material in a composition (e.g., a polypeptide or polynucleotide) means that the component or material is present at a relatively increased concentration in that composition as compared to the starting composition from which the enriched composition was generated. For example, an enriched CBH composition (or sample) is one in which the relative or absolute concentration of CBH is increased as compared to the initial fermentation product from the host organism.

As used herein, the terms "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A "constitutive" promoter is a promoter that is active under most environmental and developmental conditions. An "inducible" promoter is a promoter that is active under environmental or developmental regulation. An example of an inducible promoter useful in the present invention is the T. reesei (H. jecorina) cbh1 promoter which is deposited in GenBank under Accession Number D86235. In another aspect the promoter is a cbh II or xylanase promoter from H. jecorina. Examples of suitable promoters include the promoter from the A. awamori or A. niger glucoamylase genes (Nunberg, J. H. et al. (1984) Mol. Cell. Biol. 4, 2306-2315; Boel, E. et al. (1984) EMBO J. 3, 1581-1585), the Mucor miehei carboxyl protease gene, the Hypocrea jecorina cellobiohydrolase I gene (Shoemaker, S. P. et al. (1984) European Patent Application No. EPO0137280A1), the A. nidulans trpC gene (Yelton, M. et al. (1984) Proc. Natl. Acad. Sci. USA 81, 1470-1474; Mullaney, E. J. et al. (1985) Mol. Gen. Genet. 199, 37-45) the A. nidulans alcA gene (Lockington, R. A. et al. (1986) Gene 33, 137-149), the A. nidulans tpiA gene (McKnight, G. L. et al. (1986) Cell 46, 143-147), the A. nidulans amdS gene (Hynes, M. J. et al. (1983) Mol. Cell Biol. 3, 1430-1439), the H. jecorina xln1 gene, the H. jecorina cbh2 gene, the H. jecorina egl gene, the H.

jecorina eg2 gene, the *H. jecorina* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Thus, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "signal sequence", "signal peptide", "secretory sequence", "secretory peptide", "secretory signal sequence", "secretory signal peptide" and the like denotes a peptide sequence that, as a component of a larger polypeptide, directs the larger polypeptide through a secretory pathway of a cell in which it is synthesized, as well as nucleic acids encoding such peptides. In general, the larger polypeptide (or protein) is commonly cleaved to remove the secretory/signal peptide during transit through the secretory pathway, where the cleaved form of the polypeptide (i.e., the form without the signal/secretory peptide) is often referred to herein as the "mature form" of the polypeptide. For example, SEQ ID NO:2 provides the amino acid sequence of CBH1 from *H. jecorina* with the signal peptide while SEQ ID NO:3 provides the amino acid sequence of the mature form of CBH1 from *H. jecorina*, i.e., without the signal peptide.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct that forms an extrachromosomal self-replicating genetic element when present in many bacteria and some eukaryotes. Plasmids may be employed for any of a number of different purposes, e.g., as cloning vectors, propagation vectors, expression vectors, etc.

As used herein, the term "selectable marker" refers to a nucleotide sequence or polypeptide encoded thereby which is capable of expression in cells and where expression of the selectable marker in cells confers the ability to be differentiated from cells that do not express the selectable marker. In certain embodiments, a selectable marker allows a cell expressing it to grow in the presence of a corresponding selective agent, or under corresponding selective growth conditions. In other embodiments, a selectable marker allows a cell expressing it to be identified and/or isolated from cells that do not express it by virtue of a physical characteristic, e.g., by differences in fluorescence, immunoreactivity, etc.

In general, nucleic acid molecules which encode the variant CBH1 will hybridize, under moderate to high stringency conditions to the wild type sequence provided herein as SEQ ID NO:1 (native *H. jecorina* CBH1). However, in some cases a CBH1-encoding nucleotide sequence is employed that possesses a substantially different codon usage, while the enzyme encoded by the CBH1-encoding nucleotide sequence has the same or substantially the same amino acid sequence as the native enzyme. For example, the coding sequence may be modified to facilitate faster expression of CBH1 in a particular prokaryotic or eukaryotic expression system, in accordance with the frequency with which a particular codon is utilized by the host (commonly referred to as "codon optimization"). Te'o, et al. (2000), for example, describes the optimization of genes for expression in filamentous fungi. Such nucleic acid sequences are sometimes referred to as "degenerate" or "degenerated sequences".

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "desired cellulase expression" refers to transcription and translation of the desired cellulase gene, the products of which include precursor RNA, mRNA, polypeptide, post-translationally processed polypeptides. By way of example, assays for CBH1 expression include Western blot for CBH1 enzyme, Northern blot analysis and reverse transcriptase polymerase chain reaction (RT-PCR) assays for CBH1 mRNA, and endoglucanase activity assays as described in Shoemaker S. P. and Brown R. D. Jr. (Biochim. Biophys. Acta, 1978, 523:133-146) and Schulein (1988).

By the term "host cell" is meant a cell that contains a vector and supports the replication, and/or transcription and/or transcription and translation (expression) of the expression construct. Host cells for use in the present invention can be prokaryotic cells, such as E. coli, or eukaryotic cells such as yeast, plant, insect, amphibian, or mammalian cells. In certain embodiments, host cells are filamentous fungi.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

When an amino acid position (or residue) in a first polypeptide is noted as being "equivalent" to an amino acid position in a second, related polypeptide, it means that the amino acid position of the first polypeptide corresponds to the position noted in the second, related polypeptide by one or more of (i) primary sequence alignment (see description of sequence alignment and sequence identity below); (ii) structural sequence homology; or (iii) analogous functional property. Thus, an amino acid position in a first CBH enzyme (or a variant thereof) can be identified as "equivalent" (or "homologous") to an amino acid position in a second CBH enzyme (or even multiple different CBH enzymes).

Primary sequence alignment: Equivalent amino acid positions can be determined using primary amino acid sequence alignment methodologies, many of which are known in the art. For example, by aligning the primary amino acid sequences of two or more different CBH enzymes, it is possible to designate an amino acid position number from one CBH enzyme as equivalent to the position number of another one of the aligned CBH enzymes. In this manner, the numbering system originating from the amino acid sequence of one CBH enzyme (e.g., the CBH1 enzyme denoted in SEQ ID NO: 3) can be used to identify equivalent (or homologous) amino acid residues in other CBH enzymes (e.g., the CBH1 enzymes denoted in SEQ ID NOs: 4 to 15; see FIG. 2).

Structural sequence homology: In addition to determining "equivalent" amino acid positions using primary sequence alignment methodologies, "equivalent" amino acid positions may also be defined by determining homology at the level of secondary and/or tertiary structure. For example, for a cellulase whose tertiary structure has been determined by x-ray crystallography, equivalent residues can be defined as those for which the atomic coordinates of two or more of the main chain atoms of a particular amino acid residue of the cellulase are within 0.13 nm and preferably 0.1 nm after alignment with *Hypocrea jecorina* CBH1 (N on N, CA on CA, C on C, and O on O). Alignment is achieved after the best model has been oriented and positioned to give the maximum overlap of atomic coordinates of non-hydrogen protein atoms of the cellulase in question to the *H. jecorina* CBH1. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Analogous functional property: Equivalent amino acid residues in a first polypeptide which are functionally analogous to a specific residue of a second related polypeptide (e.g., a first cellulase and *H. jecorina* CBH1) are defined as those amino acids in the first polypeptide that adopt a conformation such that they alter, modify, or contribute to polypeptide structure, substrate binding, or catalysis in a manner defined and attributed to a specific residue of the second related polypeptide (e.g., *H. jecorina* CBH1). When a tertiary structure has been obtained by x-ray crystallography for the first polypeptide, amino acid residues of the first polypeptide that are functionally analogous to the second polypeptide occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the second polypeptide (e.g., *H. jecorina* CBH1).

The term "improved property" or "improved performance" and the like with respect to a variant enzyme (e.g., a CBH variant) is defined herein as a characteristic or activity associated with a variant enzyme which is improved as compared to its respective parent enzyme. Improved properties include, but are not limited to, improved thermostability or altered temperature-dependent activity profile, improved activity or stability at a desired pH or pH range, improved substrate specificity, improved product specificity, and improved stability in the presence of a chemical or other component in a cellulase process step, etc. Improved performance may be determined using a particular assay(s) including, but not limited to: (a) Expression (Protein Content Determination assay), (b) PASC Hydrolysis Assay, (c) PASC Hydrolysis Assay in the Presence of EG2, (d) PASC Hydrolysis Assay After Heat Incubation, (e) Whole Hydrolysate PCS (whPCS) Assay, (f) Dilute Ammonia Corn Cob (daCC) Assay, and (g) Dilute Ammonia Corn Stover (daCS) assay.

The term "improved thermostability" with respect to a variant protein (e.g., a CBH variant) is defined herein as a variant enzyme displaying retention of enzymatic activity after a period of incubation at an elevated temperature relative to the parent enzyme. Such a variant may or may not display an altered thermal activity profile relative to the parent. For example, a variant may have an improved ability to refold following incubation at elevated temperature relative to the parent.

By "improved product specificity" is meant a variant enzyme displaying an altered product profile as compared to the parent enzyme, where the altered product profile of the variant is improved in a given application as compared to the parent. A "product profile" is defined herein as the chemical composition of the reaction products produced by the enzyme of interest.

By "improved chemical stability" is meant that a variant enzyme displays retention of enzymatic activity after a period of incubation in the presence of a chemical or chemicals that reduce the enzymatic activity of the parent enzyme under the same conditions. Variants with improved chemical stability are better able to catalyze a reaction in the presence of such chemicals as compared to the parent enzyme.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

"Percent sequence identity" or grammatical equivalents means that a particular sequence has at least a certain percentage of amino acid residues identical to those in a specified reference sequence using an alignment algorithm. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (<www(dot)ncbi(dot)nlm(dot)nih(dot)gov>). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

When questions of percent sequence identity arise, alignment using the CLUSTAL W algorithm with default parameters will govern. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

II. Molecular Biology

Embodiments of the subject invention provide for the expression of a desired cellulase enzyme (or combination of cellulase enzymes) from cellulase-encoding nucleic acids under control of a promoter functional in a host cell of interest, e.g., a filamentous fungus. Therefore, this invention relies on a number of routine techniques in the field of recombinant genetics. Basic texts disclosing examples of suitable recombinant genetics methods are noted above.

Any method known in the art that can introduce mutations into a parent nucleic acid/polypeptide is contemplated by the present invention.

The present invention relates to the expression, purification and/or isolation and use of variant CBH1 enzymes. These enzymes may be prepared by recombinant methods utilizing any of a number of cbh1 genes known in the art (e.g., the cbh1 gene in SEQ ID NOs:3 to 15, e.g., from *H. jecorina*). Any convenient method for introducing mutations may be employed, including site directed mutagenesis. As indicated above, mutations (or variations) include substitutions, additions, deletions or truncations that will correspond to one or more amino acid changes in the expressed CBH1 variant. Again, site directed mutagenesis and other methods of incorporating amino acid changes in expressed proteins at the DNA level can be found in numerous references, e.g., Green and Sambrook, et al. 2012 and Ausubel, et al.

DNA encoding an amino acid sequence variant of a parent CBH1 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the parent CBH1 enzyme.

Site-directed mutagenesis is one method that can be employed in preparing substitution variants. This technique is well known in the art (see, e.g. Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the parent CBH1. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a desired cellulase can be determined, and a nucleic acid sequence encoding such amino acid sequence variant can be generated synthetically.

The desired cellulase(s) so prepared may be subjected to further modifications, oftentimes depending on the intended use of the cellulase. Such modifications may involve further alteration of the amino acid sequence, fusion to heterologous polypeptide(s) and/or covalent modifications.

III. Variant CBH1 Polypeptides and Nucleic Acids Encoding Same

In one aspect, variant CBH enzymes are provided. The variant CBH enzymes have one or more mutations, as set forth herein, with respect to a parent CBH enzyme that has at least 80% (i.e., 80% or greater) amino acid sequence identity to *H. jecorina* CBH1 (SEQ ID NO: 3), including at least 81%, 82%, 83%, 84%, 85%, 86%, 87%, 88%, 89%, 90%, 91%, 92%, 93%, 94%, 95%, 96%, 97%, 98%, 99%, up to and including 100% amino acid sequence identity to SEQ ID NO:3. In certain embodiments, the parent CBH is a fungal cellobiohydrolase 1 (CBH1), for example fungal CBH1 enzymes from *Hypocrea jecorina, Hypocrea schweinitzii, Hypocrea orientalis, Trichoderma pseudokoningii, Trichoderma konilangbra, Trichoderma citrinoviride, Trichoderma harzanium, Aspergillus aculeatus, Aspergillus niger; Penicillium janthinellum, Humicola grisea, Scytalidium thermophilum,* or *Podospora anderina*. Further, the variant CBH enzyme has cellulase activity, where in certain embodiments, the variant CBH has an improved property as compared to the parent CBH (as detailed herein). The amino acid sequence for the wild type, mature form of *H. jecorina* CBH1 is shown in FIG. 1.

In certain embodiments, a variant CBH enzyme comprises an amino acid mutation at one or more amino acid positions in the mature form of CBH1 from *H. jecorina* (SEQ ID NO:3). Because certain parent CBH enzymes according to aspects of the invention may not have the same amino acid as wild type CBH1 from *H. jecorina*, amino acid positions corresponding to the residues noted above may also be designated either by the position number alone (e.g., amino acid position 414, as denoted in Table 4) or with an "X" prefix (e.g., amino acid position X414). It is noted here that all three ways of designating the amino acid positions corresponding to a specific amino acid residue in CBH1 from *H. jecorina* are interchangeable.

The amino acid sequence of the CBH variant differs from the parent CBH amino acid sequence by the substitution, deletion or insertion of one or more amino acids of the parent amino acid sequence. A residue (amino acid) of a CBH variant is equivalent to a residue of *Hypocrea jecorina* CBH1 if it is either homologous (i.e., corresponding in position in either primary or tertiary structure) or is functionally analogous to a specific residue or portion of that residue in *Hypocrea jecorina* CBH1 (i.e., having the same or similar functional capacity to combine, react, or interact chemically or structurally). As used herein, numbering is intended to correspond to that of the mature CBH1 amino acid sequence as illustrated in FIG. 1.

Alignment of amino acid sequences to determine homology can be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. *Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada. See also the description of "percent sequence identity" provided in the Definitions section above.

In certain embodiments, the mutation(s) in a variant CBH enzyme is an amino acid substitution at a site in CBH1 from *H. jecorina* (SEQ ID NO:3) as shown in Table 4 (see Example 3). All possible combinations of the substitutions shown in Table 4 at the indicated sites are contemplated embodiments of the invention, including but not limited to the following:

1. CBH variant having at least one amino acid substitution at a position selected from the group consisting of: A414, G22, R394, T417, P227, T255, V403, F280, E337, P258, T332, T296, N49, Y493, S196, G430, T246, Y247, N307, T356, Y466, S357, Q27, S387, L318, T389, Y303, Y370, K287, T285, N350, D249, F338, S113, Y492, S398, T226, Y371, A316, K346, G340, S342, D368, M374, D179, E236, Y474, G391, F418, F311, R251, T281, V104, L326, A224, and E385.
2. CBH variant of 1 above having a A414F substitution.
3. CBH variant of 1 above having a A414N substitution.
4. CBH variant of 1 above having a A414L substitution.
5. CBH variant of 1 above having a A414M substitution.
6. CBH variant of 1 above having a A414W substitution.
7. CBH variant of 1 above having a A414R substitution.
8. CBH variant of 1 above having a A414G substitution.
9. CBH variant of 1 above having a A414K substitution.
10. CBH variant of 1 above having a A414I substitution.
11. CBH variant of 1 above having a A414H substitution.
12. CBH variant of 1 above having a A414Q substitution.
13. CBH variant of 1 above having a A414D substitution.
14. CBH variant of 1 above having a A414C substitution.
15. CBH variant of 1 above having a A414T substitution.
16. CBH variant of any one of 1 to 15 above having a G22D substitution.
17. CBH variant of any one of 1 to 15 above having a G22E substitution.
18. CBH variant of any one of 1 to 15 above having a G22H substitution.
19. CBH variant of any one of 1 to 15 above having a G22P substitution.
20. CBH variant of any one of 1 to 15 above having a G22T substitution.
21. CBH variant of any one of 1 to 15 above having a G22F substitution.
22. CBH variant of any one of 1 to 15 above having a G22C substitution.
23. CBH variant of any one of 1 to 15 above having a G22A substitution.
24. CBH variant of any one of 1 to 15 above having a G22W substitution.
25. CBH variant of any one of 1 to 15 above having a G22L substitution.
26. CBH variant of any one of 1 to 15 above having a G22Y substitution.
27. CBH variant of any one of 1 to 15 above having a G22I substitution.
28. CBH variant of any one of 1 to 15 above having a G22Q substitution.
29. CBH variant of any one of 1 to 15 above having a G22M substitution.
30. CBH variant of any one of 1 to 15 above having a G22K substitution.
31. CBH variant of any one of 1 to 15 above having a G22S substitution.
32. CBH variant of any one of 1 to 31 above having a R394E substitution.
33. CBH variant of any one of 1 to 31 above having a R394P substitution.
34. CBH variant of any one of 1 to 31 above having a R394Y substitution.
35. CBH variant of any one of 1 to 31 above having a R394F substitution.
36. CBH variant of any one of 1 to 31 above having a R394W substitution.
37. CBH variant of any one of 1 to 31 above having a R394Q substitution.
38. CBH variant of any one of 1 to 31 above having a R394L substitution.
39. CBH variant of any one of 1 to 31 above having a R394N substitution.
40. CBH variant of any one of 1 to 31 above having a R394T substitution.
41. CBH variant of any one of 1 to 31 above having a R394M substitution.
42. CBH variant of any one of 1 to 31 above having a R394C substitution.
43. CBH variant of any one of 1 to 31 above having a R394A substitution.
44. CBH variant of any one of 1 to 31 above having a R394I substitution.
45. CBH variant of any one of 1 to 31 above having a R394S substitution.
46. CBH variant of any one of 1 to 31 above having a R394G substitution.
47. CBH variant of any one of 1 to 31 above having a R394R substitution.
48. CBH variant of any one of 1 to 31 above having a R394D substitution.
49. CBH variant of any one of 1 to 31 above having a R394V substitution.
50. CBH variant of any one of 1 to 49 above having a T417W substitution.
51. CBH variant of any one of 1 to 49 above having a T417L substitution.
52. CBH variant of any one of 1 to 49 above having a T417I substitution.
53. CBH variant of any one of 1 to 49 above having a T417F substitution.
54. CBH variant of any one of 1 to 49 above having a T417E substitution.
55. CBH variant of any one of 1 to 49 above having a T417D substitution.
56. CBH variant of any one of 1 to 49 above having a T417K substitution.
57. CBH variant of any one of 1 to 49 above having a T417R substitution.
58. CBH variant of any one of 1 to 49 above having a T417H substitution.
59. CBH variant of any one of 1 to 49 above having a T417A substitution.
60. CBH variant of any one of 1 to 49 above having a T417T substitution.
61. CBH variant of any one of 1 to 49 above having a T417V substitution.
62. CBH variant of any one of 1 to 49 above having a T417Y substitution.

63. CBH variant of any one of 1 to 49 above having a T417S substitution.
64. CBH variant of any one of 1 to 49 above having a T417Q substitution.
65. CBH variant of any one of 1 to 64 above having a P227I substitution.
66. CBH variant of any one of 1 to 64 above having a P227W substitution.
67. CBH variant of any one of 1 to 64 above having a P227M substitution.
68. CBH variant of any one of 1 to 64 above having a P227V substitution.
69. CBH variant of any one of 1 to 64 above having a P227E substitution.
70. CBH variant of any one of 1 to 64 above having a P227T substitution.
71. CBH variant of any one of 1 to 64 above having a P227L substitution.
72. CBH variant of any one of 1 to 64 above having a P227A substitution.
73. CBH variant of any one of 1 to 64 above having a P227C substitution.
74. CBH variant of any one of 1 to 73 above having a T255E substitution.
75. CBH variant of any one of 1 to 73 above having a T255F substitution.
76. CBH variant of any one of 1 to 73 above having a T255L substitution.
77. CBH variant of any one of 1 to 73 above having a T255D substitution.
78. CBH variant of any one of 1 to 73 above having a T255W substitution.
79. CBH variant of any one of 1 to 73 above having a T255P substitution.
80. CBH variant of any one of 1 to 73 above having a T255D substitution.
81. CBH variant of any one of 1 to 73 above having a T255I substitution.
82. CBH variant of any one of 1 to 73 above having a T255N substitution.
83. CBH variant of any one of 1 to 73 above having a T255Q substitution.
84. CBH variant of any one of 1 to 73 above having a T255C substitution.
85. CBH variant of any one of 1 to 73 above having a T255R substitution.
86. CBH variant of any one of 1 to 73 above having a T255V substitution.
87. CBH variant of any one of 1 to 73 above having a T255K substitution.
88. CBH variant of any one of 1 to 87 above having a V403T substitution.
89. CBH variant of any one of 1 to 87 above having a V403Y substitution.
90. CBH variant of any one of 1 to 87 above having a V403N substitution.
91. CBH variant of any one of 1 to 87 above having a V403E substitution.
92. CBH variant of any one of 1 to 87 above having a V403D substitution.
93. CBH variant of any one of 1 to 87 above having a V403M substitution.
94. CBH variant of any one of 1 to 87 above having a V403I substitution.
95. CBH variant of any one of 1 to 87 above having a V403K substitution.
96. CBH variant of any one of 1 to 87 above having a V403R substitution.
97. CBH variant of any one of 1 to 87 above having a V403V substitution.
98. CBH variant of any one of 1 to 97 above having a F280I substitution.
99. CBH variant of any one of 1 to 97 above having a F280H substitution.
100. CBH variant of any one of 1 to 97 above having a F280D substitution.
101. CBH variant of any one of 1 to 97 above having a F280N substitution.
102. CBH variant of any one of 1 to 97 above having a F280V substitution.
103. CBH variant of any one of 1 to 97 above having a F280W substitution.
104. CBH variant of any one of 1 to 97 above having a F280E substitution.
105. CBH variant of any one of 1 to 97 above having a F280F substitution.
106. CBH variant of any one of 1 to 97 above having a F280S substitution.
107. CBH variant of any one of 1 to 106 above having a E337C substitution.
108. CBH variant of any one of 1 to 106 above having a E337V substitution.
109. CBH variant of any one of 1 to 106 above having a E337G substitution.
110. CBH variant of any one of 1 to 106 above having a E337Q substitution.
111. CBH variant of any one of 1 to 106 above having a E337R substitution.
112. CBH variant of any one of 1 to 106 above having a E337I substitution.
113. CBH variant of any one of 1 to 106 above having a E337M substitution.
114. CBH variant of any one of 1 to 106 above having a E337S substitution.
115. CBH variant of any one of 1 to 106 above having a E337W substitution.
116. CBH variant of any one of 1 to 115 above having a P258R substitution.
117. CBH variant of any one of 1 to 115 above having a P258I substitution.
118. CBH variant of any one of 1 to 115 above having a P258K substitution.
119. CBH variant of any one of 1 to 115 above having a P258G substitution.
120. CBH variant of any one of 1 to 115 above having a P258M substitution.
121. CBH variant of any one of 1 to 115 above having a P258H substitution.
122. CBH variant of any one of 1 to 115 above having a P258N substitution.
123. CBH variant of any one of 1 to 115 above having a P258S substitution.
124. CBH variant of any one of 1 to 115 above having a P258L substitution.
125. CBH variant of any one of 1 to 115 above having a P258Q substitution.
126. CBH variant of any one of 1 to 115 above having a P258A substitution.
127. CBH variant of any one of 1 to 126 above having a T332S substitution.
128. CBH variant of any one of 1 to 126 above having a T332M substitution.

129. CBH variant of any one of 1 to 126 above having a T332C substitution.
130. CBH variant of any one of 1 to 126 above having a T332Y substitution.
131. CBH variant of any one of 1 to 126 above having a T332K substitution.
132. CBH variant of any one of 1 to 126 above having a T332Q substitution.
133. CBH variant of any one of 1 to 126 above having a T332R substitution.
134. CBH variant of any one of 1 to 126 above having a T332A substitution.
135. CBH variant of any one of 1 to 134 above having a T296T substitution.
136. CBH variant of any one of 1 to 134 above having a T296D substitution.
137. CBH variant of any one of 1 to 134 above having a T296E substitution.
138. CBH variant of any one of 1 to 134 above having a T296Y substitution.
139. CBH variant of any one of 1 to 134 above having a T296N substitution.
140. CBH variant of any one of 1 to 134 above having a T296F substitution.
141. CBH variant of any one of 1 to 134 above having a T296K substitution.
142. CBH variant of any one of 1 to 134 above having a T296W substitution.
143. CBH variant of any one of 1 to 134 above having a T296A substitution.
144. CBH variant of any one of 1 to 134 above having a T296S substitution.
145. CBH variant of any one of 1 to 134 above having a T296L substitution.
146. CBH variant of any one of 1 to 145 above having a N49M substitution.
147. CBH variant of any one of 1 to 145 above having a N49Q substitution.
148. CBH variant of any one of 1 to 145 above having a N49L substitution.
149. CBH variant of any one of 1 to 145 above having a N49G substitution.
150. CBH variant of any one of 1 to 145 above having a N49E substitution.
151. CBH variant of any one of 1 to 145 above having a N49D substitution.
152. CBH variant of any one of 1 to 145 above having a N49A substitution.
153. CBH variant of any one of 1 to 145 above having a N49S substitution.
154. CBH variant of any one of 1 to 145 above having a N49P substitution.
155. CBH variant of any one of 1 to 154 above having a Y493E substitution.
156. CBH variant of any one of 1 to 154 above having a Y493K substitution.
157. CBH variant of any one of 1 to 154 above having a Y493N substitution.
158. CBH variant of any one of 1 to 154 above having a Y493D substitution.
159. CBH variant of any one of 1 to 154 above having a Y493I substitution.
160. CBH variant of any one of 1 to 154 above having a Y493A substitution.
161. CBH variant of any one of 1 to 154 above having a Y493V substitution.
162. CBH variant of any one of 1 to 154 above having a Y493F substitution.
163. CBH variant of any one of 1 to 162 above having a S196D substitution.
164. CBH variant of any one of 1 to 162 above having a S196V substitution.
165. CBH variant of any one of 1 to 162 above having a S196E substitution.
166. CBH variant of any one of 1 to 162 above having a S196F substitution.
167. CBH variant of any one of 1 to 162 above having a S196A substitution.
168. CBH variant of any one of 1 to 162 above having a S196K substitution.
169. CBH variant of any one of 1 to 162 above having a S196G substitution.
170. CBH variant of any one of 1 to 162 above having a S196R substitution.
171. CBH variant of any one of 1 to 162 above having a S196L substitution.
172. CBH variant of any one of 1 to 162 above having a S196P substitution.
173. CBH variant of any one of 1 to 162 above having a S196M substitution.
174. CBH variant of any one of 1 to 162 above having a S196I substitution.
175. CBH variant of any one of 1 to 174 above having a G430N substitution.
176. CBH variant of any one of 1 to 174 above having a G430Q substitution.
177. CBH variant of any one of 1 to 174 above having a G430S substitution.
178. CBH variant of any one of 1 to 174 above having a G430A substitution.
179. CBH variant of any one of 1 to 174 above having a G430R substitution.
180. CBH variant of any one of 1 to 174 above having a G430L substitution.
181. CBH variant of any one of 1 to 174 above having a G430M substitution.
182. CBH variant of any one of 1 to 174 above having a G430C substitution.
183. CBH variant of any one of 1 to 174 above having a G430D substitution.
184. CBH variant of any one of 1 to 174 above having a G430I substitution.
185. CBH variant of any one of 1 to 174 above having a G430T substitution.
186. CBH variant of any one of 1 to 185 above having a T246K substitution.
187. CBH variant of any one of 1 to 185 above having a T246L substitution.
188. CBH variant of any one of 1 to 185 above having a T246M substitution.
189. CBH variant of any one of 1 to 185 above having a T246E substitution.
190. CBH variant of any one of 1 to 185 above having a T246W substitution.
191. CBH variant of any one of 1 to 185 above having a T246N substitution.
192. CBH variant of any one of 1 to 185 above having a T246R substitution.
193. CBH variant of any one of 1 to 185 above having a T246I substitution.
194. CBH variant of any one of 1 to 185 above having a T246Q substitution.

195. CBH variant of any one of 1 to 185 above having a T246T substitution.
196. CBH variant of any one of 1 to 185 above having a T246F substitution.
197. CBH variant of any one of 1 to 185 above having a T246P substitution.
198. CBH variant of any one of 1 to 185 above having a T246S substitution.
199. CBH variant of any one of 1 to 198 above having a Y247Q substitution.
200. CBH variant of any one of 1 to 198 above having a Y247T substitution.
201. CBH variant of any one of 1 to 198 above having a Y247M substitution.
202. CBH variant of any one of 1 to 198 above having a Y247W substitution.
203. CBH variant of any one of 1 to 198 above having a Y247D substitution.
204. CBH variant of any one of 1 to 198 above having a Y247F substitution.
205. CBH variant of any one of 1 to 204 above having a N307E substitution.
206. CBH variant of any one of 1 to 204 above having a N307R substitution.
207. CBH variant of any one of 1 to 204 above having a N307A substitution.
208. CBH variant of any one of 1 to 204 above having a N307C substitution.
209. CBH variant of any one of 1 to 204 above having a N307D substitution.
210. CBH variant of any one of 1 to 204 above having a N307H substitution.
211. CBH variant of any one of 1 to 210 above having a T356M substitution.
212. CBH variant of any one of 1 to 210 above having a T356I substitution.
213. CBH variant of any one of 1 to 210 above having a T356L substitution.
214. CBH variant of any one of 1 to 213 above having a Y466R substitution.
215. CBH variant of any one of 1 to 213 above having a Y466C substitution.
216. CBH variant of any one of 1 to 213 above having a Y466V substitution.
217. CBH variant of any one of 1 to 213 above having a Y466S substitution.
218. CBH variant of any one of 1 to 217 above having a S357A substitution.
219. CBH variant of any one of 1 to 217 above having a S357G substitution.
220. CBH variant of any one of 1 to 217 above having a S357T substitution.
221. CBH variant of any one of 1 to 217 above having a S357R substitution.
222. CBH variant of any one of 1 to 217 above having a S357V substitution.
223. CBH variant of any one of 1 to 222 above having a Q27A substitution.
224. CBH variant of any one of 1 to 222 above having a Q27E substitution.
225. CBH variant of any one of 1 to 222 above having a Q27K substitution.
226. CBH variant of any one of 1 to 222 above having a Q27V substitution.
227. CBH variant of any one of 1 to 222 above having a Q27T substitution.
228. CBH variant of any one of 1 to 222 above having a Q27I substitution.
229. CBH variant of any one of 1 to 226 above having a S387K substitution.
230. CBH variant of any one of 1 to 226 above having a S387I substitution.
231. CBH variant of any one of 1 to 226 above having a S387W substitution.
232. CBH variant of any one of 1 to 226 above having a S387G substitution.
233. CBH variant of any one of 1 to 226 above having a S387D substitution.
234. CBH variant of any one of 1 to 226 above having a S387V substitution.
235. CBH variant of any one of 1 to 226 above having a S387A substitution.
236. CBH variant of any one of 1 to 235 above having a L318I substitution.
237. CBH variant of any one of 1 to 235 above having a L318V substitution.
238. CBH variant of any one of 1 to 235 above having a L318C substitution.
239. CBH variant of any one of 1 to 238 above having a T389S substitution.
240. CBH variant of any one of 1 to 238 above having a T389H substitution.
241. CBH variant of any one of 1 to 238 above having a T389V substitution.
242. CBH variant of any one of 1 to 238 above having a T389D substitution.
243. CBH variant of any one of 1 to 242 above having a Y303W substitution.
244. CBH variant of any one of 1 to 242 above having a Y303L substitution.
245. CBH variant of any one of 1 to 242 above having a Y303F substitution.
246. CBH variant of any one of 1 to 245 above having a Y370R substitution.
247. CBH variant of any one of 1 to 245 above having a Y370Q substitution.
248. CBH variant of any one of 1 to 245 above having a Y370L substitution.
249. CBH variant of any one of 1 to 245 above having a Y370G substitution.
250. CBH variant of any one of 1 to 245 above having a Y370F substitution.
251. CBH variant of any one of 1 to 250 above having a K287E substitution.
252. CBH variant of any one of 1 to 250 above having a K287Y substitution.
253. CBH variant of any one of 1 to 250 above having a K287D substitution.
254. CBH variant of any one of 1 to 250 above having a K287N substitution.
255. CBH variant of any one of 1 to 254 above having a T285R substitution.
256. CBH variant of any one of 1 to 254 above having a T285C substitution.
257. CBH variant of any one of 1 to 254 above having a T285K substitution.
258. CBH variant of any one of 1 to 254 above having a T285Q substitution.
259. CBH variant of any one of 1 to 258 above having a N350K substitution.
260. CBH variant of any one of 1 to 258 above having a N350D substitution.

261. CBH variant of any one of 1 to 258 above having a N350Q substitution.
262. CBH variant of any one of 1 to 258 above having a N350L substitution.
263. CBH variant of any one of 1 to 258 above having a N350I substitution.
264. CBH variant of any one of 1 to 263 above having a D249A substitution.
265. CBH variant of any one of 1 to 263 above having a D249Q substitution.
266. CBH variant of any one of 1 to 263 above having a D249S substitution.
267. CBH variant of any one of 1 to 266 above having a F338D substitution.
268. CBH variant of any one of 1 to 266 above having a F338L substitution.
269. CBH variant of any one of 1 to 266 above having a F338R substitution.
270. CBH variant of any one of 1 to 269 above having a S113G substitution.
271. CBH variant of any one of 1 to 269 above having a S113E substitution.
272. CBH variant of any one of 1 to 269 above having a S113N substitution.
273. CBH variant of any one of 1 to 269 above having a S113T substitution.
274. CBH variant of any one of 1 to 273 above having a Y492M substitution.
275. CBH variant of any one of 1 to 273 above having a Y492H substitution.
276. CBH variant of any one of 1 to 273 above having a Y492A substitution.
277. CBH variant of any one of 1 to 273 above having a Y492F substitution.
278. CBH variant of any one of 1 to 277 above having a S398A substitution.
279. CBH variant of any one of 1 to 277 above having a S398D substitution.
280. CBH variant of any one of 1 to 277 above having a S398P substitution.
281. CBH variant of any one of 1 to 280 above having a T226G substitution.
282. CBH variant of any one of 1 to 280 above having a T226A substitution.
283. CBH variant of any one of 1 to 280 above having a T226C substitution.
284. CBH variant of any one of 1 to 280 above having a T226D substitution.
285. CBH variant of any one of 1 to 280 above having a T226V substitution.
286. CBH variant of any one of 1 to 280 above having a T226S substitution.
287. CBH variant of any one of 1 to 286 above having a Y371Y substitution.
288. CBH variant of any one of 1 to 286 above having a Y371W substitution.
289. CBH variant of any one of 1 to 288 above having a A316I substitution.
290. CBH variant of any one of 1 to 288 above having a A316C substitution.
291. CBH variant of any one of 1 to 290 above having a K346H substitution.
292. CBH variant of any one of 1 to 291 above having a G340D substitution.
293. CBH variant of any one of 1 to 292 above having a S342C substitution.
294. CBH variant of any one of 1 to 293 above having a D368C substitution.
295. CBH variant of any one of 1 to 294 above having a M374C substitution.
296. CBH variant of any one of 1 to 295 above having a E236D substitution.
297. CBH variant of any one of 1 to 296 above having a Y474K substitution.
298. CBH variant of any one of 1 to 296 above having a Y474W substitution.
299. CBH variant of any one of 1 to 298 above having a G391Y substitution.
300. CBH variant of any one of 1 to 299 above having a F418Y substitution.
301. CBH variant of any one of 1 to 300 above having a F311Y substitution.
302. CBH variant of any one of 1 to 300 above having a F311V substitution.
303. CBH variant of any one of 1 to 302 above having a R251A substitution.
304. CBH variant of any one of 1 to 303 above having a T281D substitution.
305. CBH variant of any one of 1 to 304 above having a V104F substitution.
306. CBH variant of any one of 1 to 304 above having a V104H substitution.
307. CBH variant of any one of 1 to 306 above having a L326I substitution.
308. CBH variant of any one of 1 to 307 above having a A224Q substitution.
309. CBH variant of any one of 1 to 308 above having a E385Y substitution.

In certain embodiments, a variant CBH enzyme as described above further includes an additional amino acid mutation at one or both amino acid positions corresponding to S92 and T41 of SEQ ID NO:3, where in certain of these embodiments the mutation(s) is a substitution selected from: S92T and T41I.

All possible combinations of these additional mutations with the substitutions described above are contemplated embodiments of the invention, including but not limited to the following:

310. CBH variant of any one of 1 to 309 above and further including a S92T substitution.
311. CBH variant of any one of 1 to 310 above and further including a T41I substitution.

In another aspect, nucleic acids encoding a variant CBH enzyme having one or more mutations with respect to a parent CBH enzyme (e.g., as described above) are provided. In certain embodiments, the parent CBH1 has at least 80% (i.e., 80% or greater) amino acid sequence identity to *H. jecorina* CBH1 (SEQ ID NO:3). In certain embodiments, the nucleic acid encoding a variant CBH enzyme is at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence). It will be appreciated that due to the degeneracy of the genetic code, a plurality of nucleic acids may encode the same variant CBH enzyme. Moreover, nucleic acids encoding a variant CBH enzyme as described herein may be engineered to be codon optimized, e.g., to improve expression in a host cell of interest. Certain codon optimization techniques are known in the art.

In certain embodiments, the variant CBH enzyme-encoding nucleic acid hybridizes under stringent conditions to a nucleic acid encoding (or complementary to a nucleic acid encoding) a CBH having at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 1 (excluding the portion of the nucleic acid that encodes the signal sequence).

Nucleic acids may encode a "full-length" ("fl" or "FL") variant CBH enzyme, which includes a signal sequence, only the mature form of a variant CBH enzyme, which lacks the signal sequence, or a truncated form of a variant CBH enzyme, which lacks portions of the N and/or C-terminus of the mature form.

A nucleic acid that encodes a variant CBH enzyme can be operably linked to various promoters and regulators in a vector suitable for expressing the variant CBH enzyme in a host cell(s) of interest, as described below.

IV. Expression of Recombinant CBH1 Variants

Aspects of the subject invention include methods and compositions related to the generation nucleic acids encoding CBH variants, host cells containing such nucleic acids, the production of CBH variants by such host cells, and the isolation, purification and/or use of the CBH variants.

As such, embodiments of the invention provide host cells that have been transduced, transformed or transfected with an expression vector comprising a desired CBH variant-encoding nucleic acid sequence. For example, a filamentous fungal cell or yeast cell is transfected with an expression vector having a promoter or biologically active promoter fragment or one or more (e.g., a series) of enhancers which functions in the host cell line, operably linked to a DNA segment encoding a desired CBH variant, such that desired CBH variant is expressed in the cell line.

A. Nucleic Acid Constructs/Expression Vectors

Natural or synthetic polynucleotide fragments encoding a desired CBH variant may be incorporated into heterologous nucleic acid constructs or vectors, capable of introduction into, and replication in, a host cell of interest (e.g., a filamentous fungal or yeast cell). The vectors and methods disclosed herein are suitable for use in host cells for the expression of a desired CBH variant. Any vector may be used as long as it meets the desired replication/expression characteristics in the host cell(s) into which it is introduced (such characteristics generally being defined by the user). Large numbers of suitable vectors and promoters are known to those of skill in the art, some of which are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant host cells comprising the coding sequence for a desired CBH variant may be produced by introducing a heterologous nucleic acid construct comprising the desired CBH variant coding sequence into the desired host cells (e.g., as described in further detail below). For example, a desired CBH variant coding sequence may be inserted into a suitable vector according to well-known recombinant techniques and used to transform a filamentous fungi capable of CBH expression. As has been noted above, due to the inherent degeneracy of the genetic code, other nucleic acid sequences which encode substantially the same or a functionally equivalent amino acid sequence may be used to clone and express a desired CBH variant. Therefore it is appreciated that such substitutions in the coding region fall within the sequence variants covered by the present invention.

The present invention also includes recombinant nucleic acid constructs comprising one or more of the desired CBH variant-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a desired CBH variant: (i) in isolation; (ii) in combination with additional coding sequences; such as fusion polypeptide or signal peptide coding sequences, where the desired CBH variant coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the desired CBH variant coding sequence is a heterologous gene.

In one aspect of the present invention, a heterologous nucleic acid construct is employed to transfer a desired CBH variant-encoding nucleic acid sequence into a host cell in vitro, e.g., into established filamentous fungal and yeast lines. Long-term production of a desired CBH variant can be achieved by generating a host cell that has stable expression of the CBH variant. Thus, it follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Examples of suitable promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular host cell for expression purposes. It is operably linked to DNA sequence encoding a variant CBH1 polypeptide. Such linkage comprises positioning of the promoter with respect to the initiation codon of the DNA sequence encoding the variant CBH1 polypeptide in the expression vector such that the promoter can drive transcription/translation of the CBH variant-encoding sequence. The promoter sequence contains transcription and translation control sequence which mediate the expression of the variant CBH1 polypeptide. Examples include the promoters from the *Aspergillus niger, A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional examples of suitable selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Examples of suitable plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991.

B. Host Cells and Culture Conditions for CBH1 and Variant CBH1 Enzyme Production After DNA sequences that encode the CBH1 variants have been cloned into DNA constructs, the DNA is used to transform microorganisms. The microorganism to be transformed for the purpose of expressing a variant CBH1 according to the present invention can be chosen from a wide variety of host cells. The sections below are provided as examples of host cells/microorganisms and are not meant to limit the scope of host cells that can be employed in practicing aspects of the present invention.

(i) Filamentous Fungi

Aspect of the present invention include filamentous fungi which have been modified, selected and cultured in a manner effective to result in desired CBH variant production or expression relative to the corresponding non-transformed parental filamentous fungi.

Examples of species of parental filamentous fungi that may be treated and/or modified for desired cellulase expression include, but are not limited to *Trichoderma, Penicillium* sp., *Humicola* sp., including *Humicola insolens; Aspergillus* sp., including *Aspergillus niger, Chrysosporium* sp., *Myceliophthora* sp., *Fusarium* sp., *Hypocrea* sp., and *Emericella* sp.

Cells expressing a desired CBH variant are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Standard culture conditions are known in the art, e.g., cultures are incubated at 28° C. in shaker cultures or fermenters until desired levels of desired CBH variant expression are achieved.

Culture conditions for a given filamentous fungus can be found, for example, in the scientific literature and/or from the source of the fungi such as the American Type Culture Collection (ATCC). After fungal growth has been established, the cells are exposed to conditions effective to cause or permit the expression of a desired CBH variant.

In cases where a desired CBH variant coding sequence is under the control of an inducible promoter, the inducing agent, e.g., a sugar, metal salt or antibiotic, is added to the medium at a concentration effective to induce expression of the desired CBH variant.

In one embodiment, the strain is an *Aspergillus niger* strain, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAPS-4 are known Ward et al (Ward, M, Wilson, L. J. and Kodama, K. H., 1993, Appl. Microbiol. Biotechnol. 39:738-743).

In another embodiment, the strain is a *Trichoderma reesei* strain, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH.

Where it is desired to obtain the desired CBH variant in the absence of potentially detrimental native cellulase activity, it is useful to obtain a host cell strain which has had one or more cellulase genes deleted prior to introduction of a DNA construct or plasmid containing the DNA fragment encoding the desired CBH variant. Such strains may be prepared in any convenient manner, for example by the method disclosed in U.S. Pat. No. 5,246,853 and WO 92/06209, which disclosures are hereby incorporated by reference. By expressing a desired CBH variant in a host microorganism that is missing one or more cellulase genes (e.g., the endogenous CBH1 gene of a host cell), identification and subsequent purification procedures, where desired, are simplified.

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, for example from about 0.5 to about 2.0 kb may remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

In certain embodiments, more than one copy of DNA encoding a desired CBH variant may be present in a host strain to facilitate overexpression of the CBH variant. For example, a host cell may have multiple copies of a desired CBH variant integrated into the genome or, alternatively, include a plasmid vector that is capable of replicating autonomously in the host organism.

(ii) Yeast

The present invention also contemplates the use of yeast as a host cell for desired CBH production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from *Aureobasidlium pullulans* (Li and Ljungdahl, 1996), an alpha-amylase from wheat (Rothstein et al., 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (BgI1) was successfully expressed in a laboratory strain of *S. cerevisiae* (Van Rensburg et al., 1998).

(iii) Other

It is further contemplated that in some embodiments, expression systems in host cells other than filamentous fungal cells or yeast cells may be employed, including insect cell or bacterial cell expression systems. Certain of the bacterial host cells can, for example, be one that is also an ethanologen, such as an engineered *Zymomonas mobilis*, which is not only capable of expressing the enzyme(s)/variant(s) of interest but also capable of metabolizing certain monomeric and other fermentable sugars, turning them into ethanol. The selection of a host cell may be determined by the desires of the user of the CBH variants described herein, and thus no limitation in that regard is intended.

C. Introduction of a Desired CBH-Encoding Nucleic Acid Sequence Into Host Cells

The invention further provides cells and cell compositions which have been genetically modified to comprise an exogenously provided desired CBH variant-encoding nucleic acid sequence. A parental cell or cell line may be genetically modified (e.g., transduced, transformed or transfected) with a cloning vector or an expression vector. The vector may be, for example, in the form of a plasmid, a viral particle, a phage, etc., as further described above.

The methods of transformation of the present invention may result in the stable integration of all or part of the transformation vector into the genome of the host cell. However, transformation resulting in the maintenance of a self-replicating extra-chromosomal transformation vector is also contemplated.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). In essence, the particular genetic engineering procedure used should be capable of successfully introducing a polynucleotide (e.g., an expression vector) into the host cell that is capable of expressing the desired CBH variant.

Many standard transfection methods can be used to produce *Trichoderma reesei* cell lines that express large quantities of the heterologus polypeptide. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138). An example of a suitable transformation process for *Aspergillus* sp. can be found in Campbell et al. Improved transformation efficiency of *A. niger* using homologous niaD gene for nitrate reductase. Curr. Genet. 16:53-56; 1989.

The invention further includes novel and useful transformants of host cells, e.g., filamentous fungi such as *H. jecorina* and *A. niger*, for use in producing fungal cellulase compositions. Thus, aspects of the subject invention include transformants of filamentous fungi comprising the desired CBH variant coding sequence, sometimes also including a deletion of the endogenous cbh coding sequence.

In addition, heterologous nucleic acid constructs comprising a desired cellulase-encoding nucleic acid sequence can be transcribed in vitro, and the resulting RNA introduced into the host cell by well-known methods, e.g., by injection.

D. Analysis for CBH1 Nucleic Acid Coding Sequences and/or Protein Expression

In order to evaluate the expression of a desired CBH variant by a cell line that has been transformed with a desired CBH variant-encoding nucleic acid construct, assays can be carried out at the protein level, the RNA level or by use of functional bioassays particular to cellobiohydrolase activity and/or production.

In general, assays employed to analyze the expression of a desired CBH variant include, but are not limited to, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a desired CBH variant may be measured in a sample directly, for example, by assays for cellobiohydrolase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of CBH1 to hydrolyze isolated soluble and insoluble substrates can be measured using assays described in Srisodsuk et al., J. Biotech. (1997) 57:49-57 and Nidetzky and Claeyssens Biotech. Bioeng. (1994) 44:961-966. Substrates useful for assaying cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression may be evaluated by immunological methods, such as ELISA, competitive immunoassays, radioimmunoassays, Western blot, indirect immunofluorescent assays, and the like. Certain of these assays can be performed using commercially available reagents and/or kits designed for detecting CBH enzymes. Such immunoassays can be used to qualitatively and/or quantitatively evaluate expression of a desired CBH variant. The details of such methods are known to those of skill in the art and many reagents for practicing such methods are commercially available. In certain embodiments, an immunological reagent that is specific for a desired variant CBH enzyme but not its parent CBH may be employed, e.g., an antibody that is specific for a CBH substitution or a fusion partner of the CBH variant (e.g., an N or C terminal tag sequence, e.g., a hexa-Histidine tag or a FLAG tag). Thus, aspects of the present invention include using a purified form of a desired CBH variant to produce either monoclonal or polyclonal antibodies specific to the expressed polypeptide for use in various immunoassays. (See, e.g., Hu et al., 1991).

V. Methods for Enrichment, Isolation and/or Purification of CBH Variant Polypeptide In general, a desired CBH variant polypeptide produced in a host cell culture is secreted into the medium (producing a culture supernatant containing the CBH variant) and may be enriched, purified or isolated, e.g., by removing unwanted components from the cell culture medium. However, in some cases, a desired CBH variant polypeptide may be produced in a cellular form necessitating recovery from a cell lysate. The desired CBH variant polypeptide is harvested from the cells or cell supernatants in which it was produced using techniques routinely employed by those of skill in the art. Examples include, but are not limited to, filtration (e.g., ultra- or micro-filtration), centrifugation, density gradient fractionation (e.g., density gradient ultracentrifugation), affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

While enriched, isolated or purified CBH variant polypeptide is sometimes desired, in some embodiments, a host cell expressing a CBH variant polypeptide is employed directly in an assay that requires cellobiohydrolase activity. Thus, enrichment, isolation or purification of the desired CBH variant polypeptide is not always required to obtain a CBH variant polypeptide composition that finds use in a cellulase assay or process. For example, a cellulase system according to aspects of the present invention might be designed to allow a host cell that expresses a variant CBH1 as described herein to be used directly in a cellulase process, i.e., without isolation of the CBH1 away from the host cell prior to its use in an assay of interest. In one such example, CBH1 variant-expressing yeast cells may be added directly into a fermentation process such that the yeast cell expresses the variant CBH1 directly into the fermentation broth where its cellulase activity converts a non-fermentable substrate into fermentable sugars for the yeast cell to convert directly to a desired product, e.g., into ethanol (see, e.g., Ilmén et al., High level secretion of cellobiohydrolases by *Saccharomyces cerevisiae* Biotechnology for Biofuels 2011, 4:30).

VI. Utility of CBH1 Variants

It can be appreciated that the desired CBH variant-encoding nucleic acids, the desired CBH variant polypeptide and compositions comprising the same find utility in a wide variety applications, some of which are described below. The improved property or properties of the CBH variants described herein can be exploited in many ways. For example, CBH variants with improved performance under conditions of thermal stress can be used to increase cellulase activity in assays carried out at high temperatures (e.g., temperatures at which the parent CBH would perform poorly), allowing a user to reduce the total amount of CBH employed (as compared to using the parent CBH). Other improved properties of CBH variant polypeptides can be exploited in cellulase assays, including CBH variants having altered pH optima, increased stability or activity in the presence of surfactants, increased specific activity for a substrate, altered substrate cleavage pattern, and/or high level expression in a host cell of interest.

Thus, CBH variant polypeptides as describe herein find use in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of CBH variants provides the ability to control characteristics and activity of such compositions.

A cellulase composition containing a desired CBH variant as described herein finds use in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Separate saccharification and fermentation is a process whereby cellulose present in biomass, e.g., corn stover, is converted to glucose and subsequently yeast strains convert the glucose into ethanol. Simultaneous saccharification and fermentation is a process whereby cellulose present in biomass is converted to glucose and, at the same time and in the same reactor, yeast strains convert glucose into ethanol.

Thus, the CBH variants of the invention find use in the both of these processes for the degradation of biomass to ethanol. Ethanol production from readily available sources of cellulose provides a stable, renewable fuel source. It is further noted that in some processes, biomass is not fully broken down to glucose (containing, e.g., disaccharides), as such products find uses apart from ethanol production.

Cellulose-based feedstocks can take a variety of forms and can contain agricultural wastes, grasses and woods and other low-value biomass such as municipal waste (e.g., recycled paper, yard clippings, etc.). Ethanol may be produced from the fermentation of any of these cellulosic feedstocks. As such, a large variety of feedstocks may be used with the inventive desired cellulase(s) and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

In another embodiment the cellulosic feedstock may be pretreated. Pretreatment may be by elevated temperature and the addition of dilute acid, concentrated acid or dilute alkali solution. The pretreatment solution is added for a time sufficient to at least partially hydrolyze the hemicellulose components and then neutralized.

In addition to biomass conversion, CBH variant polypeptides as described herein can be present in detergent compositions which can include any one or more detergent components, e.g., a surfactant (including anionic, non-ionic and ampholytic surfactants), a hydrolase, building agents, bleaching agents, bluing agents and fluorescent dyes, caking inhibitors, solubilizers, cationic surfactants and the like. All of these components are known in the detergent art. The CBH variant polypeptide-containing detergent composition can be in any convenient form, including liquid, granule, emulsion, gel, paste, and the like. In certain forms (e.g., granules) the detergent composition can be formulated so as to contain a cellulase protecting agent. For a more thorough discussion, see U.S. Pat. No. 6,162,782 entitled "Detergent compositions containing cellulase compositions deficient in CBH1 type components," which is incorporated herein by reference.

In certain embodiments, the CBH variant polypeptide is present in the detergent compositions from 0.00005 weight percent to 5 weight percent relative to the total detergent composition, e.g., from about 0.0002 weight percent to about 2 weight percent relative to the total detergent composition.

It is noted that CBH variants with decreased thermostability find use, for example, in areas where the enzyme activity is required to be neutralized at lower temperatures so that other enzymes that may be present are left unaffected. In addition, the enzymes may find utility in the limited conversion of cellulosics, for example, in controlling the degree of crystallinity or of cellulosic chain-length. After reaching the desired extent of conversion, the saccharifying temperature can be raised above the survival temperature of the de-stabilized CBH variant. As the CBH activity is essential for hydrolysis of crystalline cellulose, conversion of crystalline cellulose will cease at the elevated temperature.

As seen from above, CBH variant polypeptides (and the nucleic acids encoding them) with improved properties as compared to their parent CBH enzymes find use in improving any of a number of assays and processes that employ cellobiohydrolases.

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

Example 1

I. Assays

The following assays were used in the examples described below. Any deviations from the protocols provided below are indicated in the examples. In these experiments, a spectrophotometer was used to measure the absorbance of the products formed after the completion of the reactions.

A. Performance Index

The performance index (P1) compares the performance or stability of the variant (measured value) and the standard enzyme (theoretical value) at the same polypeptide concentration. In addition, the theoretical values can be calculated using the parameters of the Langmuir equation of the standard enzyme. A dose response curve was generated for the wild-type EG4 by fitting the data with the Langmuir equation with intercept $(y=((x*a)/(x+b))+c)$ and the activities of the EG4 variants were divided by a calculated activity of wild-type EG4 of the same plate to yield a performance index. A performance index (PI) that is greater than 1 (PI>1) indicates improved performance by a variant as compared to the standard (e.g., wild-type *Hypocrea jecorina* cellobiohydrolase 1, also known as CBH1 or Cel7A), while a PI of 1 (PI=1) identifies a variant that performs the same as the standard, and a PI that is less than 1 (PI<1) identifies a variant that performs worse than the standard.

B. Protein Content Determination 8.1. Bradford Protein Content Determination Assay The Bradford dye reagent (Quick Start) assay was used to determine the protein concentration in samples on MTP scale. The chemical and reagent solutions used were: Quick Start Bradford Dye Reagent (BIO-RAD Catalog No. 500-0205), and dilution buffer (50 mM NaAc pH 5.0). The equipment used was a Biomek FX Robot (Beckman) and a SpectraMAX (type 340) MTP reader. The MTPs were from Costar (type 9017). Twenty (20) µL of culture supernatant for each CBH1 variant was combined with 180 µL of 50 mM NaAc pH 5.0 in a 96 well micro-titer plate. Bovine Serum Albumin (BSA) was similarly added to the plate as an assay control in concentrations ranging from 0-133.3 ppm. One-hundred seventy five (175) µL Bradford dye reagent was pipetted into each well, followed by 25 µL from the 10× diluted supernatant plate described above. After thorough mixing, the MTPs were incubated for 20 minutes at room temperature. Air bubbles were blown away and the OD of each well was read at 595 nm. The $OD_{595}$ values obtained provide a relative measure of the protein content in the samples. Variant concentrations were determined using the calibration curve generated by the BSA controls.

8.2. HPLC Protein Content Determination

The concentration of CBH1 variant polypeptides from pooled culture supernatants was determined using an Agilent 1200 HPLC equipped with a Proswift SAX-1S (4.6×50 mm) column (Dionex). Fifty (50) microliters of sample, mixed with 50 µl of 50 mM $NaH_2PO_4$ pH 6.7 in filtered demineralized water was injected following equilibration of the HPLC column for 1.5 min with 25 mM $NaH_2PO_4$ pH 6.7. Compounds were eluted using a gradient of 0% to 55% 25 mM NaH2PO4 pH 6.7+500 mM NaCl from 1.5 to 3.5 min. Protein concentrations of CBH1 variants were determined from a calibration curve generated using purified wild-type CBH1 (0-800 ppm). To calculate performance index ($P_i$ or PI), the ratio of the (average) total protein produced by a variant and (average) total protein produced by the wild-type at the same dose were averaged.

8.3. UPLC Protein Content Determination

The concentration of CBH1 variant polypeptides from pooled culture supernatants was determined using an Agilent 1200 HPLC equipped with a Acquity UPLC BEH200 SEC 1.7 µm (4.6×150 mm) column (Waters #186005225). Twenty five (25) microliters of sample was mixed with 75 µL of de-mineralized water. Ten (10) µL of the 4× diluted sample was injected onto the column. To elute the sample, 25 mM NaH2PO4 pH 6.7+100 mM NaCl was run isocratically for 5.0 min. Protein concentrations of CBH1 variants were determined from a calibration curve generated using purified wild-type CBH1 (0-1410 ppm). To calculate performance index ($P_i$ or PI), the ratio of the (average) total protein produced by a variant and (average) total protein produced by the wild-type at the same dose were averaged.

C. ABTS Assay for Measurement of Glucose

Residual glucose from *H. jecorina* culture supernatants expressing CBH1 variants was measured. Supernatants of cultures with residual glucose were excluded from pooling for further studies. Monomeric glucose was detected using the ABTS assay. The assay buffer contained 2.74 g/L 2,2'-azino-bis(3-ethylbenzo-thiazoline-6-sulfonic acid) di-ammonium salt (ABTS, Sigma, catalog no. A1888), 0.1 U/mL horseradish peroxidase Type VI-A (Sigma, catalog no. P8375), and 1 Unit/mL food grade glucose oxidase (GENENCOR® 5989 U/mL) in 50 mM sodium acetate buffer pH 5.0. Ten (10) microliters (diluted) BGL1 activity assay mix was added to 100 µL ABTS assay solution. After adding the activity assay mix, the reaction was followed kinetically for 5 min at $OD_{420}$, at ambient temperature of 22° C. An appropriate calibration curve of glucose for each assay condition was always included.

D. Phosphoric Acid Swollen Cellulose (PASC) Hydrolysis Assays

D.1. Phosphoric Acid Swollen Cellulose (PASC) Hydrolysis Assay

Phosphoric acid swollen cellulose (PASC) was prepared from Avicel according to a published method (Walseth, Tappi 35:228, 1971; and Wood, Biochem J, 121:353-362, 1971). This material was diluted with buffer and water to achieve a 0.5% w/v mixture such that the final concentration of sodium acetate was 50 mM, pH 5.0. CBH1 activity was determined by adding 15 µL culture supernatant to 85 µL reaction mix (0.15% PASC; 0.42 mg/ml culture supernatant of a *H. jecorina* strain deleted for cbh1, cbh2, eg1, eg2, eg3, and bgl1; 29.4 mM NaOAc (pH 5.0)) in a 96-well microtiterplate (Costar Flat Bottom PS 3641). The micro-titer plate was sealed and incubated in a thermostatted incubator at 50° C. under continuous shaking at 900 rpm for 3 hours, followed by 5 min cooling on ice. The hydrolysis reaction was stopped by the addition of 100 µL quench buffer (100 mM glycine buffer (pH 10); 5 mg/ml calcofluor (Sigma)). Activity was determined according to a published method (Du et al, Appl Biochem Biotechnol 161 (1-8): 313-7). A dose response curve was generated for wild-type CBH1 enzyme. Assays were performed in quadruplicate. To calculate performance index ($P_i$ or PI), the ratio of the (average) total sugar produced by a variant and (average) total sugar produced by the wild-type at the same dose were averaged.

D.2. Phosphoric Acid Swollen Cellulose (PASC) Hydrolysis Assay

Phosphoric acid swollen cellulose (PASO) was prepared from Avicel according to a published method (Walseth, Tappi 35:228, 1971; and Wood, Biochem J, 121:353-362, 1971). This material was diluted with buffer and water to achieve a 0.5% w/v mixture such that the final concentration of sodium acetate was 50 mM, pH 5.0. CBH1 activity was determined by adding 5 µL, 10 µL, 20 µL and 40 µL of 400 ppm anion purified (see 1.1) CBH1 to 140 µL reaction mix (0.36% PASO; 29.4 mM NaOAc (pH 5.0); 143 mM NaCl) in a 96-well microtiterplate (Costar Flat Bottom PS 3641). The micro-titer plate was sealed and incubated in a thermostatted incubator at 50° C. under continuous shaking at 900 rpm for 2 hours, followed by 5 min cooling on ice. The hydrolysis reaction was stopped by the addition of 100 µL quench buffer (100 mM glycine buffer (pH 10). The hydrolysis reaction products were analyzed with a PAHBAH assay according to Lever, 1972, Anal Biochem, 47:273-279 with the following modifications: PAHBAH assay: Aliquots of 150 µL of PAHBAH reducing sugar reagent (for 100 mL reagent: 1.5 g p-hydroxybenzoic acid hydrazide (Sigma #H9882), 5 g Potassium sodium tartrate tetrahydrate dissolved in 2% NaOH), were added to all wells of an empty microtiter plate. Ten (10) microliters of the hydrolysis reaction supernatants were added to the PABAH reaction plate. All plates were sealed and incubated at 69° C. under continuous shaking of 900 rpm. After one hour the plates were placed on ice for five minutes and centrifuged at 720×g at room temperature for five minutes. Absorbance of plates (endpoint) was measured at 410 nm in a spectrophotometer. A cellobiose standard was included as control and appropriate blank samples. A dose response curve was generated for wild-type CBH1 enzyme. To calculate performance index (PI), the (average) total sugar produced by a variant CBH1 was divided by the (average) total sugar produced by the wild-type CBH1 (e.g. a reference enzyme) at the same dose.

D.3. Phosphoric Acid Swollen Cellulose (PASC) Hydrolysis Assay in the Presence of EGII The PASO assay in the presence of 2.5 ppm *T. reesei* EGII was performed as described for the assay under D.2 (i.e., without EGII) with the following modifications: 400 ppm of anion purified CBH1 enzyme was diluted 1.6 fold before addition to the assay, reaction additions was the same as under D.2 only 10 µL of 37.5 ppm EGII was added to the reaction mix resulting in a total reaction volume of 150 µL. PI was calculated as described under D.2.

E. Thermostability Assays

E.1. Phosphoric Acid Swollen Cellulose (PASC) Hydrolysis Assay After Heat Incubation Residual activity of CBH1 variants after heat incubation was determined using the PASO hydrolysis assay essentially as described under assay D.1. Culture supernatants expressing CBH1 variants were diluted 2-fold in 50 mM sodium acetate buffer pH 5.0. Aliquots of 50 µL were incubated in quadruplicate in a skirted 96-well PCR plate in a PCR machine at 61.5° C. for 1 hour. After incubation, the residual specific activity of CBH1 wild-type and variant polypeptides was determined as described above with the difference that 30 µL culture supernatant to 70 µL reaction mix (0.25% PASO; 0.51 mg/ml culture supernatant of a H. jecorina strain deleted for cbh1, cbh2, eg1, eg2, eg3, and bgl1; 25 mM NaOAc (pH5.0)). The relative residual activity of the variants and that of the wild-type polypeptide were determined by the ratio of the averaged specific activity after incubation and the averaged specific activity before incubation. A performance index (PI or Pi) for the CBH1 variants was determined by dividing the relative residual activity of the variant by the relative residual activity of the wild-type CBH1 (e.g., a reference enzyme).

E.2. Phosphoric Acid Swollen Cellulose (PASC) Hydrolysis Assay after Heat Incubation Residual activity of CBH1 variants after heat incubation was determined using the PASC hydrolysis assay essentially as described under D.2. Culture supernatants expressing CBH1 variants were diluted to a total volume of 72 µL as follows: 63, 54, 32 and 0 µL 50 mM sodium acetate buffer pH 5.0 containing 500 mM NaCl and 9, 18, 36 and 72 µL of 400 ppm anion purified (e.g., as described in section J below) CBH1. These aliquots of 72 µL were incubated in 96-well VWR PCR plate in a PCR machine at 60.0° C. for 1 hour. After incubation the residual specific activity of CBH1 wild-type and variant polypeptides was determined as described above in D.2. The relative residual activity of the variants and the wild-type polypeptide was determined by the ratio of the averaged specific activity after incubation and the averaged specific activity before incubation. To calculate performance index ($P_i$ or PI), the ratio of the (average) total sugar produced by a variant and (average) total sugar produced by the wild-type at the same dose were averaged.

F. Whole Hydrolysate Acid-Pretreated Corn Stover (whPCS) Assay

Corn stover was pretreated with 2% w/w $H_2SO_4$ as described (Schell et al., J Appl Biochem Biotechnol, 105: 69-86, 2003). Volumes of 3, 5, 10 and 25 µL supernatant (2-fold diluted in 50 mM NaOAc) were added to whPCS reaction mixtures (6.5% (w/v) whPCS; 1.43 mg/ml supernatant of H. jecorina deleted for cbh1 and cbh2 (as described in WO 2005/001036); 0.22 mg/ml Xyn3; 0.15 mg/ml Fv51A; 0.18 mg/ml Fv3A; 0.15 mg/ml Fv43D; 0.22 mg/ml BGL1 with a final total volume of 160 µL. (Examples of suitable methods employing the enzymes Xyn3, Fv51A, Fv3A, Fv43D, and Bgl1 are described in PCT application publication WO2011/0038019). The micro-titer plate was sealed and incubated in a thermostatted incubator at 50° C. under continuous shaking at 900 rpm for 3 hours, followed by 5 min cooling on ice. The hydrolysis reaction was stopped by the addition of 100 µL quench buffer (100 mM glycine buffer, pH 10). Plates were centrifuged at room temperature for 5 minutes at 3,000 rpm, and a 20× dilution of the sample was made by adding 10 µL of the sample to 190 µL of water. Free glucose in the reaction was measured using the ABTS assay as described under assay C.

G. Dilute Ammonia Corn Cob (daCC) Assay

Corncob was ground to pass a 0.9 mm screen and pretreated as described (WO 2006110901). Pretreated corncob was used as a 7% cellulose suspension in 50 mM sodium acetate (pH 5.0). Volumes of 3, 5, 10 and 25 µL supernatant were added to daCC reaction mixtures (3.5% (w/v) cellulose; 2.86 mg/ml supernatant of H. jecorina deleted for cbh1 and cbh2 (as described in WO 2005/001036); 0.44 mg/ml Xyn3; 0.30 mg/ml Fv51A; 0.36 mg/ml Fv3A; 0.30 mg/ml Fv43D; 0.44 mg/ml BGL1 with a final total volume of 160 µL. (As noted above, exemplary methods employing the enzymes Xyn3, Fv51A, Fv3A, Fv43D, and Bgl1 are described in PCT application publication WO2011/0038019). The micro-titer plate was sealed and incubated in a thermostatted incubator at 50° C. under continuous shaking at 900 rpm for 3 hours, followed by 5 min cooling on ice. The hydrolysis reaction was stopped by the addition of 100 µL quench buffer (100 mM glycine buffer (pH 10). Plates were centrifuged at room temperature for 5 minutes at 3,000 rpm, and a 20× dilution of the sample was made by adding 10 µL of the sample to 190 µL of water. Free glucose in the reaction was measured using the ABTS assay as described under assay C.

H. Dilute Ammonia Corn Stover (daCS) Assay

Dilute ammonia pretreated corn stover was prepared essentially as described for dilute ammonia corncob (WO2006/110901). Pretreated corn stover was used as a 10% cellulose suspension in 50 mM sodium acetate (pH 5.0). Volumes of 3, 5, 10 and 20 µL supernatant were added to daCS reaction mixtures (5.8% (w/v) cellulose; 0.052 mg/ml H. jecorina CBH2; 0.13 mg/ml H. jecorina Xyn3; 0.011 mg/ml Fv51A; 0.006 mg/ml Fv3A; 0.011 mg/ml Fv43D; 0.08 mg/ml Fv3C; 0.04 mg/ml EG4; 0.05 mg/ml H. jecorina Δ(cbh1, cbh2) with a final total volume of 120 µL. (As noted above, examples of suitable methods employing the enzymes Xyn3, Fv51A, Fv3A, Fv43D, and Fv3C are described in PCT application publication WO2011/0038019). The micro-titer plate was sealed and incubated in a thermostatted incubator at 50° C. under continuous shaking at 900 rpm for 24 hours, followed by 5 min cooling on ice. The hydrolysis reaction was stopped by the addition of 100 µL quench buffer (100 mM glycine buffer (pH 10). Plates were centrifuged at room temperature for 5 minutes at 3,000 rpm, and a 20× dilution of the sample was made by adding 10 µL of the sample to 190 µL of water. Free glucose in the reaction was measured using the ABTS assay as described under assay C.

I. Protein Purification

For micro-scale purification, 200 µL of 90% ethanol was transferred to a Multiscreen deep-well solvinert hydrophobic PTFE filter plate (MiliPore #MDRPN0410) followed by 1 min centrifugation at 50×g. Four hundred (400) μL of DEAE Sepharose Fast-Flow resin (GE-Healthcare #17-0709-01) was transferred to the filter plate followed by centrifugation of 1 min at 50×g. The resin was washed three times using 400 μL MiliQ water, and equilibrated three times using 400 μL of 25 mM NaH$_2$PO$_4$ (pH 6.7). Four hundred and fifty (450) μL of culture supernatant was diluted 6× to 2700 μL using 25 mM NaH$_2$PO$_4$ (pH 6.7). Diluted samples were loaded on the resin. To elute all unbound protein, the resin was washed three times with 25 mM NaH$_2$PO$_4$ (pH 6.7). CBH1 variants were eluted using 400 μL of 25 mM NaAc pH5.0+ 500 mM NaCl.

For large-scale purification, a Vivaspin20 10 kDMWO filter (Sartorius #VS2001) was used to concentrate 20 mL of CBH1 shake flask sample to 2.5 mL (centrifuged for 20 minutes at 3000×g). The concentrated sample was diluted to 10 mL using 50 mM NaAc pH 5.0. A 1 mL Hitrap DEAE FF column (GE-Healthcare #17-5055-01) was equilibrated using 25 mM NaAc pH 5.0. The diluted sample was loaded on the column at 1.0 mL/min. After complete loading of the sample, the column was washed with 12 column volumes (CV) of 25 mM NaAc pH 5.0 at 1 mL/min. CBH1 was eluted from the column using a 30 CV gradient from 0% to 50% of 25 mM NaAc pH 5.0+1M NaCl. During the gradient, fractions of 5 mL were collected. Fractions were analyzed by SDS-PAGE. The three fractions containing most CBH1 were pooled.

J. Measurement of Protein Melting Temperature (Tm)

Stability of CBH1 variants was determined by a fluorescent dye-binding thermal shift assay (Lavinder et al, High-throughput thermal scanning: A general, rapid dye-binding thermal shift screen for protein engineering (2009) JACS, 131: 3794-3795). SyproOrange (Molecular Probes) was diluted 1:1000 in MQ water. In a well, 8 μl diluted dye was mixed with 25 μl 100 mg/l enzyme in 50 mM NaOAc (pH 5). Sealed plates were subjected to a temperature gradient of 25° C. to 95° C. with an approximate rate of 1° C./min in an ABI 7900HT rtPCR system (Applied Biosystems). The mid-peak temperature of the first derivative of the fluorescence signal was taken as the melting temperature (Tm) of the CBH1 enzyme in the sample.

Example 2

Generation of *Hypocrea jecorina* CBH1 Variants

In this example, the construction of *Trichoderma reesei* strains expressing wild-type *Hypocrea jecorina* cellobiohydrolase 1 (CBH1) and variants, thereof, are described. A cDNA fragment listed below as SEQ ID NO: 1 (previously described in U.S. Pat. No. 7,452,707), encoding CBH1 (SEQ ID NO: 3) served as template DNA for the construction of *Trichoderma reesei* strains expressing CBH1 and variants thereof. The cDNA was inserted into the expression plasmid pTTT-pyrG to generate pTTT-pyrG-cbh1 (as shown in FIG. 3).

SEQ ID NO: 1 includes the wild type nucleotide sequence encoding the mature form of *H. jecorina* cbh1 adjacent to a sequence encoding the CBH1 signal peptide (underlined):

<u>atgtatcggaagttggccgtcatctcggccttcttggccacagctcg</u>
<u>tgct</u>cagtcggcctgcactctccaatcggagactcaccgcctctga
catggcagaaatgctcgtctggtggcacgtgcactcaacagacaggc
tccgtggtcatcgacgccaactggcgctggactcacgctacgaacag
cagcacgaactgctacgatggcaacacttggagctcgaccctatgtc
ctgacaacgagacctgcgcgaagaactgctgtctggacggtgccgcc
tacgcgtccacgtacggagttaccacgagcggtaacagcctctccat
tggctttgtcacccagtctgcgcagaagaacgttggcgctcgcctt
accttatggcgagcgacacgacctaccaggaattcacctgcttggc
aacgagttctctttcgatgttgatgtttcgcagctgccgtgcggctt
gaacggagctctctacttcgtgtccatggacgcggatggtggcgtga
gcaagtatcccaccaacaccgctggcgccaagtacggcacggggtac
tgtgacagccagtgtccccgcgatctgaagttcatcaatggccaggc
caacgttgagggctgggagccgtcatccaacaacgcgaacacgggca
ttggaggacacggaagctgctgctctgagatggatatctgggaggcc
aactccatctccgaggctcttacccccaccccttgcacgactgtcgg
ccaggagatctgcgagggtgatgggtgcggcggaacttactccgata
acagatatggcggcacttgcgatcccgatggctgcgactggaaccca
taccgcctgggcaacaccagcttctacgccctggctcaagctttac
cctcgataccaccaagaaattgaccgttgtcacccagttcgagacgt
cgggtgccatcaaccgatactatgtccagaatggcgtcactttccag
cagcccaacgccgagcttggtagttactctggcaacgagctcaacga
tgattactgcacagctgaggaggcagaattcggcggatcctcttcct
cagacaagggcggcctgactcagttcaagaaggctacctctggcggc
atggttctggtcatgagtctgtgggatgattactacgccaacatgct
gtggctggactccacctacccgacaaacgagacctcctccacaccg
gtgccgtgcgcggaagctgctccaccagctccggtgtccctgctcag
gtcgaatctcagtctcccaacgccaaggtcaccttctccaacatcaa
gttcggacccattggcagcaccggcaaccctagcggcggcaaccctc
ccggcggaaacccgcctggcaccaccaccaccccgccgcccagccact
accactggaagctctcccggacctacccagtctcactacggccagtg
cggcggtattggctacagcggcccacggtctgcgccagcggcacaa
cttgccaggtcctgaaccttactactctcagtgcctg SEQ ID NO:2 sets forth the sequence of the *H. jecorina* CBH1 full length polypeptide containing the CBH1 signal peptide (underlined):

<u>myrklavisaflataraq</u>sactlqsethppltwqkcssggtctqqtg
svvidanwrwthatnsstncydgntwsstlcpdnetcaknccldgaa
yastygvttsgnslsigfvtqsaqknvgarlylmasdttyqeftllg
nefsfdvdvsqlpcglngalyfvsmdadggvskyptntagakygtgy
cdsqcprdlkfingqanvegwepssnnantgigghgsccsemdiwea -continued

```
nsisealtphpcttvgqeicegdgcggtysdnryggtcdpdgcdwnp yrlgntsfygpgssftldttkkltvvtqfetsgainryyvqngvtfq qpnaelgsysgnelnddyctaeeaefggssfsdkggltqfkkatsgg mvlvmslwddyyanmlwldstyptnetsstpgavrgscstssgvpaq vesqspnakvtfsnikfgpigstgnpsggnppggnppgttttrrpat ttgsspgptqshygqcggigysgptvcasgttcqvlnpyysqcl
```

SEQ ID NO:3 sets forth the sequence of the *H. jecorina* CBH1 mature enzyme:

```
qsactlcisethppltwqkcssggtctqqtgsvvidanwrwthatns stncydgntwsstlcpdnetcaknccldgaayastygvttsgnslsi gfvtqsaqknvgarlylmasdttycleftllgnefsfdvdvsqlpcg lngalyfvsmdadggvskyptntagakygtgycdsqcprdlkfingc lanvegwepssnnantgigghgsccsemdiweansisealtphpctt vgqeicegdgcggtysdnryggtcdpdgcdwnpyrlgntsfygpgss ftldttkkltvvtqfetsgainryyvqngvtfqqpnaelgsysgnel nddyctaeeaefggssfsdkggltqfkkatsggmvlvmslwddyyan mlwldstyptnetsstpgavrgscstssgvpaqvesqspnakvtfsn ikfgpigstgnpsggnppggnppgttttrrpatttgsspgptqshyg qcggigysgptvcasgttcqvlnpyysqcl
```

The pTTTpyrG-cbh1 plasmid, shown in FIG. 3, containing the *Hypocrea jecorina* CBH1 enzyme encoding sequence (SEQ ID NO: 1) was used as a template to generate site evaluation libraries (SELs) of CBH1 variants, where each CBH1 variant enzyme produced by the libraries have an amino acid substitutions at at least one position (or site) in the mature CBH1 enzyme (SEQ ID NO:2). For each site selected for substitution, typically 14-16 substitution variants were obtained.

Production of CBH1 Variant Polypeptides

Purified pTTTpyrG-cbh1 plasmids ($P_{cbh1}$, $Amp^R$, acetamidase; see plasmid schematic shown in FIG. 3) expressing genes encoding CBH1 variant enzymes were expressed in a six gene deleted *Trichoderma reesei* strain (Δeg11, Δeg12, Δeg13, Δcbh1, Δcbh2, Δbgl1) that was derived from RL-P37 (Sheir-Neiss, G et al. Appl. Microbiol. Biotechnol. 1984, 20:46-53), and is further described in PCT Application Publication WO2010/141779. Gene deletions were created according to the methods described in PCT Application Publication WO2005/001036 for making a four gene deleted *T. reesei* strain (Δeg11, Δeg12, Δcbh1, Δcbh2), which was similarly further deleted for egl3 and bgl1, resulting in the six gene deleted strain. Protoplasts of the six-fold deleted *T. reesei* were transformed with the individual pTTT-pyrG-cbh1 constructs (a single CBH1 variant per transformation) and grown on selective agar containing acetamide at 28° C. for 7 d as previously described in PCT Application Publication WO2009/048488. Transformants of *T. reesei* were revived on selective agar containing acetamide and incubated at 28° C. for 7 d. Spores were harvested by scraping each well with 300 μL saline+ 0.015% Tween-80. For CBH1 variant production, a volume of 10 μL or 25 μL spore suspension was added to 200 μL of 1 mL Aachen medium in a 96-well or 24-well plate respectively. The plates were closed with an Enzyscreen lid and fermented for 7 days at 28° C. and 80% humidity in a 50 mm throw Infors incubator. The broth was transferred to 96-well filterplates and filtrated under vacuum. Residual glucose was measured using the ABTS assay as described in Example C. The remaining spore suspensions were stored in 50% glycerol at −80° C.

Example 3

Identification of Highly Combinable and Productive Mutations

Performance index (PI) values were determined for all the CBH1 variants tested using the following assays (described in Example 1): Protein Content Determination (as described in B2 or B3), PASC Hydrolysis Assay (as described in D1 or D2), PASC Hydrolysis Assay in the Presence of EG2 (as described in D3), PASC Hydrolysis Assay After Heat Incubation (as described in E1 or E2), Whole Hydrolysate PCS (whPCS) Assay (as described in F), Dilute Ammonia Corn Cob (daCC) Assay (as described in G), and Dilute Ammonia Corn Stover (daCS) Assay (as described in H).

Productive positions are described as those positions within a molecule that are most useful for making combinatorial variants exhibiting an improved characteristic, where the position itself allows for at least one combinable mutation. Highly combinable mutations are mutations at any amino acid position that can be used to make combinatorial variants. Highly combinable mutations improve at least one desired property of the molecule, while not significantly decreasing expression, activity, or stability. Highly combinable mutations can be grouped as follows:

Group A: A mutation that produces a variant wherein the minimum performance indices (PI) relative to a defined parent polypeptide for: (i) protein expression using the Protein Content Determination Assay as described in B2 or B3; (ii) activity using the PASC hydrolysis assay as described in D1 or D2, the PASC Hydrolysis Assay in the Presence of EG2 as described in D3, the Whole Hydrolysate PCS (whPCS) Assay as described in F, the Dilute Ammonia Corn Cob (daCC) Assay described in G, or the Dilute Ammonia Corn Stover (daCS) Assay described in H; and (iii) thermostability using PASC Hydrolysis Assay After Heat Incubation described in E1 or E2, are greater than or equal to 0.9, and in addition have a PI for any one of these tests that is greater than or equal to 1.0.

Group B: A mutation that produces a variant wherein the minimum performance indices (PI) relative to a defined parent polypeptide for: (i) protein expression using the Protein Content Determination Assay as described in B2 or B3; (ii) activity using the PASC hydrolysis assay as described in D1 or D2, the PASO Hydrolysis Assay in the Presence of EG2 as described in D3, the Whole Hydrolysate PCS (whPCS) Assay as described in F, the Dilute Ammonia Corn Cob (daCC) Assay described in G, or the Dilute Ammonia Corn Stover (daCS) Assay described in H; and (iii) thermostability using PASO Hydrolysis Assay After Heat Incubation described in E1 or E2, are greater than or equal to 0.8, and in addition have a PI for any one of these tests that is greater than or equal to 1.2.

Group C: A mutation that produces a variant wherein the minimum performance indices (PI) relative to a defined parent polypeptide for: (i) protein expression using the Protein Content Determination Assay as described in B2 or B3; (ii) activity using the PASO hydrolysis assay as described in D1 or D2, the PASO Hydrolysis Assay in the Presence of EG2 as described in D3, the Whole Hydrolysate PCS (whPCS) Assay as described in F, the Dilute Ammonia Corn Cob (daCC) Assay described in G, or the Dilute Ammonia Corn Stover (daCS) Assay described in H; and (iii) thermostability using PASO Hydrolysis Assay After Heat Incubation described in E1 or E2, are greater than or equal to 0.5, and in addition have a PI for any one of these tests that is greater than or equal to 1.5.

The properties of highly combinable mutations are summarized in the following Table.

TABLE 2

Properties for each group of highly combinable mutations Performance Index (PI)

| Expression | Activity | Thermostability | Minimum PI in one or more tests |
|---|---|---|---|
| ≥0.9 | ≥0.9 | ≥0.9 | X ≥ 1.0 |
| ≥0.8 | ≥0.8 | ≥0.8 | X ≥ 1.2 |
| ≥0.5 | ≥0.5 | ≥0.5 | X ≥ 1.5 |

Preferred combinable mutations are at "productive positions," as described, below. In the case of the present cellobiohydrolases, "activity" refers to cellobiohydrolase activity, which can be measured as described, herein.

Productive positions are amino acid positions that are tolerant to substitution with different amino acid residues, wherein the resulting variants meet a set of performance criteria for combinability, as set forth above. Productive positions can be assigned a Productivity Score as follows:

Positions where less than 15% of the substitutions at a given position fall within groups A, B, or C are given a Productivity Score of "1".

Positions where less than 40%, but greater than, or equal to 15% of the substitutions at a given position fall within groups A, B, or C are given a Productivity Score of "2".

Positions where less than 75%, but greater than, or equal to 40% of the substitutions at a given position fall within groups A, B, or C are given a Productivity Score of "3".

Positions where 75% or more of the substitutions at a given position fall within groups A, B, or C are given a Productivity Score of "4".

Preferred productive positions are highly combinable mutations.

Suitability score refers to the ability of one or more highly combinable mutations to be used to make combinatorial variants, based on the performance criteria for combinability, (i.e., A, B, and C, as set forth, above) in which each of the mutations fall. A higher suitability score indicates a mutation or mutations that are more suitable for use in making combinatorial variants.

Suitability scores are described in Table 3 below.

TABLE 3

Definitions of suitability scores

| Substitutions Occur in Group(s) | Suitability Score |
|---|---|
| A, B and C | +++++ |
| A and B | ++++ |
| A or (B and C) | +++ |
| B | ++ |
| C | + |

Table 4 shows the Productivity Score (4, 3, 2, or 1) calculated for each position in the CBH1 polypeptide. For each CBH1 position, variants are listed according to the suitability score they received (+, ++, +++, ++++, or +++++). Position numbering is based on the mature CBH1 polypeptide listed in SEQ ID NO: 3.

TABLE 4

Productivity and Suitability Scores for CBH1 variant polypeptides

| POS | Productivity score | Variants suitability score | | | | |
|---|---|---|---|---|---|---|
| | | + | ++ | +++ | ++++ | +++++ |
| 414 | 4 | N, L, M, W, R, G, K, I, H, Q, D, C, T | | A | | F |
| 22 | 4 | D, E, H, P | T, F, C | A, W, L, Y, I | | Q, M, K, S |
| 394 | 4 | E | P, Y, F | W, Q, L, N, T, M, C, A, I, S | G | R, D, V |
| 417 | 4 | W | L | I, F, E, D, K, R, H, A, T, V | | Y, S, Q |
| 227 | 3 | I, W | | M, V, E, T, L | | A, C |
| 255 | 3 | E, F, L | S | W, P, D, I, N, Q, C, R | V | K |
| 403 | 3 | T, Y, N, E, D, M | I | K | | R, V |
| 280 | 3 | I, H, D | N, V | W, E, F | | S |
| 337 | 3 | C | V, G | Q, R, I | M | S, W |
| 258 | 3 | R, I | K, G, M, H | N, S, L, Q | A | |
| 332 | 3 | S | M, C | Y | K, Q, R, A | |
| 296 | 3 | T, D | E | Y, N, F, K, W, A, S | L | |
| 49 | 3 | M, Q, L, G, E, D | | A, S, P | | |
| 493 | 3 | E, K, N, D, I, A | V | F | | |
| 196 | 3 | D, V, E, F, A | K | G, R, L, P, M, I | | |
| 430 | 3 | N, Q, S, A, R, L | | M, C, D, I, T | | |
| 246 | 3 | K, L, M, E, W, N, R, I, Q, T, F, P | | S | | |
| 247 | 2 | | Q, T, M | W, D | | F |
| 307 | 2 | E | R, A | | C, D | H |

TABLE 4-continued

Productivity and Suitability Scores for CBH1 variant polypeptides

| POS | Productivity score | + | ++ | +++ | ++++ | +++++ |
|---|---|---|---|---|---|---|
| 356 | 2 | M | I | | | L |
| 466 | 2 | R | C | | V | S |
| 357 | 2 | A | G | T | R | V |
| 27 | 2 | A, E | K | V, T | I | |
| 387 | 2 | K, I, W, G, D, V | | A | | |
| 318 | 2 | I, V | | C | | |
| 389 | 2 | S, H, V | | D | | |
| 303 | 2 | W, L | | F | | |
| 370 | 2 | R, Q | L | G, F | | |
| 287 | 2 | E, Y, D | | N | | |
| 285 | 2 | R, C, K | | Q | | |
| 350 | 2 | K, D | | Q, L, I | | |
| 249 | 2 | A | | Q, S | | |
| 338 | 2 | D | L | R | | |
| 113 | 2 | G, E | N | T | | |
| 492 | 2 | M, H, A | F | | | |
| 398 | 2 | A, D | P | | | |
| 226 | 2 | G, A, C, D, V, S | | | | |
| 371 | 1 | Y | | | W | |
| 316 | 1 | I | | C | | |
| 346 | 1 | | | H | | |
| 340 | 1 | | | S | | |
| 342 | 1 | | C | | | |
| 368 | 1 | | C | | | |
| 374 | 1 | | C | | | |
| 179 | 1 | | D | | | |
| 236 | 1 | | D | | | |
| 474 | 1 | K | W | | | |
| 391 | 1 | | Y | | | |
| 418 | 1 | | Y | | | |
| 311 | 1 | | Y, V | | | |
| 251 | 1 | A | | | | |
| 281 | 1 | D | | | | |
| 104 | 1 | F, H | | | | |
| 326 | 1 | I | | | | |
| 224 | 1 | Q | | | | |
| 385 | 1 | Y | | | | |

As noted above, any combination of variants in Table 4 finds use in aspects of the present invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, et al., Ed., p11 et seq., Academic Press, 1988.
Ausubel G. M., et al. CURRENT PROTOCOLS IN MOLECULAR BIOLOGY, John Wiley & Sons, New York, N.Y., 1993.
Baldwin, D., et al., Curr. Opin. Plant Biol. 2(2):96-103, 1999.
Baulcombe, D., Arch. Virol. Suppl. 15:189-201, 1999.
Bhikhabhai, R. et al., J. Appl. Biochem. 6:336, 1984.
Boer and Koivula, 2003, Eur. J. Biochem. 270: 841-848
Brumbauer, A. et al., Bioseparation 7:287-295, 1999.
Carter et al., Nucl. Acids Res. 13:4331, 1986.
Chen et al., Biochem. Biophys. Acta. 1121:54-60, 1992.
Coligan, J. E. et al., eds., CURRENT PROTOCOLS IN IMMUNOLOGY, 1991.
Collen, A., et al., Journal of Chromatography A 910:275-284, 2001.
Coughlan, et al., BIOCHEMISTRY AND GENETICS OF CELLULOSE DEGRADATION.
Cummings and Fowler, Curr. Genet. 29:227-233, 1996.
Dayhoff et al. in Atlas of Protein Sequence and Structure, Volume 5, Supplement 3, Chapter 22, pp. 345-352, 1978.
Deutscher, M. P., Methods Enzymol. 182:779-80, 1990.
Doolittle, R. F., OF URFS AND ORFS, University Science Books, Calif., 1986.
Ellouz, S. et al., J. Chromatography 396:307, 1987.
Fields and Song, Nature 340:245-246, 1989.
Filho, et al. Can. J. Microbiol. 42:1-5, 1996.
Fliess, A., et al., Eur. J. Appl. Microbiol. Biotechnol. 17:314, 1983.
Freer, et al. J. Biol. Chem. 268:9337-9342, 1993.
Freshney, R. I., ed., ANIMAL CELL CULTURE, 1987.
Goyal, A. et al. Bioresource Technol. 36:37, 1991.
Halldorsdottir, S et al., Appl Microbiol Biotechnol. 49(3): 277-84, 1998.
Hu et al., Mol Cell Biol. 11:5792-9, 1991.
Hemmpel, W. H. ITB Dyeing/Printing/Finishing 3:5-14, 1991.
Herr et al., Appl. Microbiol. Biotechnol. 5:29-36, 1978.
Jakobovits, A, et al., Ann N Y Acad Sci 764:525-35, 1995.

Jakobovits, A, Curr Opin Biotechnol 6 (5):561-6, 1995.
Jones et al., Nature 321:522-525, 1986.
Kawaguchi, T et al., Gene 173 (2):287-8, 1996.
Knowles, J. et al., TIBTECH 5, 255-261, 1987.
Kohler and Milstein, Nature 256:495, 1975.
Krishna, S. et al., Bioresource Tech. 77:193-196, 2001.
Kumar, A., et al., Textile Chemist and Colorist 29:37-42, 1997.
Lehtio, J. et al., FEMS Microbiology Letters 195:197-204, 2001.
Li and Ljungdahl Appl. Environ. Microbiol. 62:209-213, 1996.
Linder, M. and Teeri, T. T., Biotechnol. 57:15-28, 1997.
Medve, J. et al., J. Chromatography A 808:153, 1998.
Ohmiya et al., Biotechnol. Gen. Engineer. Rev. 14:365-414, 1997.
Ooi et al., Nucleic Acids Res. 18 (19):5884, 1990.
Ortega et al., International Biodeterioration and Biodegradation 47:7-14, 2001.
Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J Biochem. 224 (3):923-30, 1994.
Stahlberg, J. et al., Bio/Technol. 9:286-290, 1991.
Stahlberg et al., 1996, J. Mol. Biol. 264: 337-349
Strathern et al., eds. (1981) The Molecular Biology of the Yeast *Saccharomyces*.
Suurnakki, A. et al., Cellulose 7:189-209, 2000.
Te'o, J. et al., FEMS Microbiology Letters 190:13-19, 2000.
Tilbeurgh, H. et al., FEBS Lett. 16:215, 1984.
Timberlake et al., *Cell* 1:29-37, 1981.
Tomaz, C. and Queiroz, J., J. Chromatography A 865:123-128, 1999.
Tomme, P. et al., Eur. J. Biochem. 170:575-581, 1988.
Tormo, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.
Verhoeyen et al., Science 239:1534-1536, 1988.
Warrington, et al., *Genomics* 13:803-808, 1992.
Wells et al., Gene 34:315, 1985.
Wells et al., Philos. Trans. R. Soc. London SerA 317:415, 1986.
Wood, Biochem. Soc. Trans., 13, pp. 407-410, 1985.
Wood et al., METHODS IN ENZYMOLOGY, 160, 25, p. 87 et seq., Academic Press, New York, 1988.
Zoller et al., Nucl. Acids Res. 10:6487, 1987.

---

What is claimed is:

1. A variant of a parent cellobiohydrolase 1 (CBH1) enzyme, wherein said variant has cellulase activity, comprises at least one amino acid substitution, has at least 90% amino acid sequence identity to SEQ ID NO:3, and has at least one improved property over said parent CBH1 enzyme selected from: (a) expression (protein content determination), (b) phosphoric acid swollen cellulose (PASC) hydrolysis assay activity, (c) PASC hydrolysis assay activity in the presence of endoglucanase 2 (EG2), (d) PASC hydrolysis assay activity after heat incubation, (e) whole hydrolysate acid-pretreated corn stover (whPCS) assay activity, (f) dilute ammonia corn cob (daCC) assay activity, and (g) dilute ammonia corn stover (daCS) assay activity; and wherein the at least one amino acid substitution is with an alanine, glutamine, or serine at a position that corresponds to position D249 of SEQ ID NO:3.

2. The variant of claim 1, wherein said at least one amino acid substitution is with an alanine.

3. The variant of claim 1, wherein said variant comprises an additional amino acid substitution at one or both amino acid positions corresponding to S92 and T41 of SEQ ID NO:3.

4. The variant of claim 3, wherein said additional amino acid substitution is selected from the group consisting of: S92T, T41I, and both S92T and T41I.

5. A host cell comprising an expression vector comprising a polynucleotide sequence encoding the variant according to claim 1.

6. The host cell of claim 5, wherein said host cell is selected from the group consisting of:
   a filamentous fungal cell selected from the group consisting of: *Trichoderma reesei, Trichoderma longibrachiatum, Trichoderma viride, Trichoderma Trichoderma harzianum, Penicillium, Humicola, Humicola insolens, Humicola grisea, Chrysosporium, Chrysosporium lucknowense, Myceliophthora thermophilia, Gliocladium, Aspergillus, Fusarium, Neurospora, Hypocrea, Emericella, Aspergillus niger, Aspergillus awamori, Aspergillus aculeatus*, and *Aspergillus nidulans*;
   a yeast cell selected from the group consisting of: *Saccharomyces cerevisiae, Schizosaccharomyces pombe, Schwanniomyces occidentalis, Kluyveromyces lactis, Candida utilis, Candida albicans, Pichia stipitis, Pichia pastoris, Yarrowia lipolytica, Hansenula polymorpha, Phaffia rhodozyma, Arxula adeninivorans, Debaryomyces hansenii*, and *Debaryomyces polymorphus*; and
   a *Zymomonas mobilis* cell.

7. The host cell of claim 5, wherein said host cell expresses the variant.

8. A method for hydrolyzing a cellulosic substrate, comprising:
   contacting said substrate with a composition comprising the variant according to claim 1,
   and optionally producing ethanol by culturing an ethanologen in a medium comprising glucose and/or glucose-containing oligosaccharide products of the hydrolysis.

9. The method of claim 8, wherein said cellulosic substrate is selected from the group consisting of grass, switch grass, cord grass, rye grass, reed canary grass, *miscanthus*, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, wood pulp, recycled wood pulp fiber, paper sludge, sawdust, hardwood, softwood, and combinations thereof.

10. The method of claim 8, wherein the composition further comprises one or more additional cellulases or hemicellulases.

11. The variant of claim 1, wherein the variant has at least 95% amino acid sequence identity to SEQ ID NO:3.

12. The variant of claim 11, wherein the variant has at least 97% amino acid sequence identity to SEQ ID NO:3.

13. The variant of claim 11, wherein the variant has at least 98% amino acid sequence identity to SEQ ID NO:3.

* * * * *

SEQUENCE LISTING

```
<160> NUMBER OF SEQ ID NOS: 15

<210> SEQ ID NO 1
<211> LENGTH: 1542
<212> TYPE: DNA
<213> ORGANISM: Hypocrea jecorina
<220> FEATURE:
<221> NAME/KEY: misc_feature
<223> OTHER INFORMATION: includes the wild type nucleotide sequence
      encoding the mature form of H. jecorina cbh1 adjacent to a
      sequence encoding the CBH1 signal peptide

<400> SEQUENCE: 1
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acgtgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg gacggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtgcggctt gaacggagct     480
ctctacttcg tgtccatgga cgcggatggt ggcgtgagca gtatcccac caacaccgct     540 ggcgccaagt acggcacggg gtactgtgac agccagtgtc cccgcgatct gaagttcatc     600
aatggccagg ccaacgttga gggctgggag ccgtcatcca caacgcgaa cacgggcatt     660 ggaggacacg gaagctgctg ctctgagatg gatatctggg aggccaactc catctccgag     720
gctcttaccc cccaccttg cacgactgtc ggccaggaga tctgcgaggg tgatgggtgc     780
```

```
ggcggaactt actccgataa cagatatggc ggcacttgcg atcccgatgg ctgcgactgg    840
aacccatacc gcctgggcaa caccagcttc tacggccctg ctcaagctt taccctcgat    900 accaccaaga aattgaccgt tgtcacccag ttcgagacgt cgggtgccat caaccgatac    960
tatgtccaga tggcgtcac tttccagcag cccaacgccg agcttggtag ttactctggc    1020
aacgagctca cgatgatta ctgcacagct gaggaggcag aattcggcgg atcctctttc    1080
tcagacaagg gcggcctgac tcagttcaag aaggctacct ctggcggcat ggttctggtc    1140
atgagtctgt gggatgatta ctacgccaac atgctgtggc tggactccac ctacccgaca    1200
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccacccgccg cccagccact accactggaa gctctcccgg acctacccag    1440
tctcactacg gccagtgcgg cggtattggc tacagcggcc ccacggtctg cgccagcggc    1500
acaacttgcc aggtcctgaa cccttactac tctcagtgcc tg    1542
```

<210> SEQ ID NO 2
<211> LENGTH: 514
<212> TYPE: PRT
<213> ORGANISM: Hypocrea jecorina
<220> FEATURE:
<221> NAME/KEY: misc_feature
<223> OTHER INFORMATION: sequence of the H. jecorina CBH1 full length
      polypeptide containing the CBH1 signal peptide

<400> SEQUENCE: 2

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
```

```
                210                 215                 220
Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
                275                 280                 285

Ser Phe Tyr Gly Pro Gly Ser Ser Phe Thr Leu Asp Thr Thr Lys Lys
                290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asn
                435                 440                 445

Pro Ser Gly Gly Asn Pro Pro Gly Gly Asn Pro Pro Gly Thr Thr Thr
                450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
                500                 505                 510

Cys Leu

<210> SEQ ID NO 3
<211> LENGTH: 497
<212> TYPE: PRT
<213> ORGANISM: Hypocrea jecorina
<220> FEATURE:
<221> NAME/KEY: misc_feature
<223> OTHER INFORMATION: sequence of the H. jecorina CBH1 mature enzyme

<400> SEQUENCE: 3

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
                35                  40                  45

Asn Cys Tyr Asp Gly Asn Thr Trp Ser Ser Thr Leu Cys Pro Asp Asn
```

```
            50                  55                  60
Glu Thr Cys Ala Lys Asn Cys Cys Leu Asp Gly Ala Ala Tyr Ala Ser
 65                  70                  75                  80

Thr Tyr Gly Val Thr Thr Ser Gly Asn Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
        130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
            275                 280                 285

Thr Val Val Thr Gln Phe Glu Thr Ser Gly Ala Ile Asn Arg Tyr Tyr
        290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr
            435                 440                 445

Arg Arg Pro Ala Thr Thr Thr Gly Ser Ser Pro Gly Pro Thr Gln Ser
        450                 455                 460

His Tyr Gly Gln Cys Gly Gly Ile Gly Tyr Ser Gly Pro Thr Val Cys
465                 470                 475                 480
```

```
Ala Ser Gly Thr Thr Cys Gln Val Leu Asn Pro Tyr Tyr Ser Gln Cys
                485                 490                 495
Leu

<210> SEQ ID NO 4
<211> LENGTH: 497
<212> TYPE: PRT
<213> ORGANISM: Hypocrea orientalis

<400> SEQUENCE: 4

Gln Ser Ala Cys Thr Leu Gln Thr Glu Thr His Pro Ser Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Asp Gly
225                 230                 235                 240

Asp Gly Cys Gly Gly Thr Tyr Ser Asn Asp Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Tyr Gln Gln Pro Asn Ala Glu Leu Gly Ser
305                 310                 315                 320

Tyr Ser Gly Asn Glu Leu Asn Asp Asp Tyr Cys Thr Ala Glu Glu Ser
                325                 330                 335

Glu Phe Gly Gly Ser Ser Phe Ser Asp Lys Gly Gly Leu Thr Gln Phe
            340                 345                 350
```

Lys Lys Ala Thr Ser Gly Gly Met Val Leu Val Met Ser Leu Trp Asp
            355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Leu Glu Ser Gln Ser Pro Asn Ala Lys Val
                405                 410                 415

Val Tyr Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
            435                 440                 445

Arg Arg Pro Ala Thr Thr Thr Gly Ser Ser Pro Gly Pro Thr Gln Thr
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 5
<211> LENGTH: 497
<212> TYPE: PRT
<213> ORGANISM: Hypocrea schweinitzii

<400> SEQUENCE: 5

Gln Ser Ala Cys Thr Leu Gln Thr Glu Thr His Pro Ser Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Asn Val Gly Gln Glu Ile Cys Asp Gly
225                 230                 235                 240

Asp Gly Cys Gly Gly Thr Tyr Ser Asn Asp Arg Tyr Gly Gly Thr Cys
            245                 250                 255

Asp Pro Asp Gly Cys Asp Trp Asn Pro Tyr Arg Leu Gly Asn Thr Ser
        260                 265                 270

Phe Tyr Gly Pro Gly Ser Ser Phe Thr Leu Asp Thr Thr Lys Lys Leu
    275                 280                 285

Thr Val Val Thr Gln Phe Glu Thr Ser Gly Ala Ile Asn Arg Tyr Tyr
290                 295                 300

Val Gln Asn Gly Val Thr Tyr Gln Gln Pro Asn Ala Glu Leu Gly Ser
305                 310                 315                 320

Tyr Ser Gly Asn Glu Leu Asn Asp Ala Tyr Cys Thr Ala Glu Glu Ser
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Leu Glu Ser Gln Ser Ala Asn Ala Lys Val
                405                 410                 415

Val Tyr Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Thr
    450                 455                 460

His Tyr Gly Gln Cys Gly Gly Ile Gly Tyr Ser Gly Pro Thr Ile Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 6
<211> LENGTH: 497
<212> TYPE: PRT
<213> ORGANISM: Trichoderma citrinoviride
<220> FEATURE:
<221> NAME/KEY: misc_feature
<222> LOCATION: (217)..(217)
<223> OTHER INFORMATION: Xaa can be any naturally occurring amino acid

<400> SEQUENCE: 6

Gln Ser Ala Cys Thr Leu Gln Thr Glu Thr His Pro Ser Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser

```
             65                  70                  75                  80
        Thr Tyr Gly Val Thr Thr Ser Ala Asp Ser Leu Ser Ile Gly Phe Val
                            85                  90                  95

Thr Gln Ser Ala Gln Lys Asn Val Gly Ala Arg Leu Tyr Leu Met Ala
                        100                 105                 110

Ser Asp Thr Thr Tyr Gln Glu Phe Thr Leu Leu Gly Asn Glu Phe Ser
                    115                 120                 125

Phe Asp Val Asp Val Ser Gln Leu Pro Cys Gly Leu Asn Gly Ala Leu
                130                 135                 140

Tyr Phe Val Ser Met Asp Ala Asp Gly Gly Val Ser Lys Tyr Pro Thr
        145                 150                 155                 160

Asn Thr Ala Gly Ala Lys Tyr Gly Thr Gly Tyr Cys Asp Ser Gln Cys
                            165                 170                 175

Pro Arg Asp Leu Lys Phe Ile Asn Gly Gln Ala Asn Val Glu Gly Trp
                        180                 185                 190

Glu Pro Ser Ser Asn Asn Ala Asn Thr Gly Ile Gly Gly His Gly Ser
                    195                 200                 205

Cys Cys Ser Glu Met Asp Ile Trp Xaa Ala Asn Ser Ile Ser Glu Ala
                210                 215                 220

Leu Thr Pro His Pro Cys Thr Thr Val Gly Gln Glu Ile Cys Glu Gly
        225                 230                 235                 240

Asp Gly Cys Gly Gly Thr Tyr Ser Asn Asp Arg Tyr Gly Gly Thr Cys
                            245                 250                 255

Asp Pro Asp Gly Cys Asp Trp Asn Pro Tyr Arg Leu Gly Asn Thr Ser
                        260                 265                 270

Phe Tyr Gly Pro Gly Ser Ser Phe Thr Leu Asp Thr Thr Lys Lys Leu
                    275                 280                 285

Thr Val Val Thr Gln Phe Glu Thr Ser Gly Ala Ile Asn Arg Tyr Tyr
                290                 295                 300

Val Gln Asn Gly Val Thr Tyr Lys Gln Pro Asn Ala Glu Leu Gly Ser
        305                 310                 315                 320

Tyr Ser Gly Asn Glu Leu Asn Asp Asp Tyr Cys Thr Ala Glu Glu Ser
                            325                 330                 335

Glu Phe Gly Gly Ser Ser Phe Ser Asp Lys Gly Gly Leu Thr Gln Phe
                        340                 345                 350

Lys Lys Ala Thr Ser Gly Gly Met Val Leu Val Met Ser Leu Trp Asp
                    355                 360                 365

Asp Tyr Tyr Ala Asn Met Leu Trp Leu Asp Ser Thr Tyr Pro Thr Asn
                370                 375                 380

Glu Thr Ser Ser Thr Pro Gly Ala Val Arg Gly Ser Cys Ser Thr Ser
        385                 390                 395                 400

Ser Gly Val Pro Ala Gln Leu Glu Ser Gln Ser Pro Asn Ala Lys Val
                            405                 410                 415

Val Tyr Ser Asn Ile Lys Phe Gly Pro Ile Gly Ser Thr Gly Asn Pro
                        420                 425                 430

Ser Gly Gly Asn Pro Pro Gly Gly Asn Pro Pro Gly Thr Thr Thr Thr
                    435                 440                 445

Arg Arg Pro Ala Thr Thr Thr Gly Ser Ser Pro Gly Pro Thr Gln Thr
                450                 455                 460

His Tyr Gly Gln Cys Gly Gly Ile Gly Tyr Ser Gly Pro Thr Val Cys
        465                 470                 475                 480

Ala Ser Gly Thr Thr Cys Gln Val Leu Asn Glu Tyr Tyr Ser Gln Cys
                            485                 490                 495
```

Leu

<210> SEQ ID NO 7
<211> LENGTH: 498
<212> TYPE: PRT
<213> ORGANISM: Trichoderma pseudokoningii

<400> SEQUENCE: 7

```
Gln Ser Ala Cys Thr Leu Gln Thr Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Glu Ala Asn Val Glu Gly Trp
            180                 185                 190

Glu Pro Phe Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Asp Gly
225                 230                 235                 240

Asp Ser Cys Gly Gly Thr Tyr Ser Gly Asp Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Ala Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Ser Leu Asp Asp Tyr Cys Ala Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365
```

```
Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Leu Glu Ser Gln Ser Ser Asn Ala Lys Val
                405                 410                 415

Val Tyr Ser Asn Ile Lys Phe Gly Pro Ile Gly Ser Thr Gly Asn Ser
            420                 425                 430

Ser Gly Gly Ser Pro Pro Gly Gly Asn Pro Pro Gly Thr Thr Thr
        435                 440                 445

Thr Arg Arg Pro Ala Thr Ser Thr Gly Ser Ser Pro Gly Pro Thr Gln
450                 455                 460

Thr His Tyr Gly Gln Cys Gly Gly Ile Gly Tyr Ser Gly Pro Thr Val
465                 470                 475                 480

Cys Ala Ser Gly Ser Thr Cys Gln Val Leu Asn Pro Tyr Tyr Ser Gln
                485                 490                 495

Cys Leu

<210> SEQ ID NO 8
<211> LENGTH: 498
<212> TYPE: PRT
<213> ORGANISM: Trichoderma konilangbra
<220> FEATURE:
<221> NAME/KEY: misc_feature
<222> LOCATION: (273)..(273)
<223> OTHER INFORMATION: Xaa can be any naturally occurring amino acid

<400> SEQUENCE: 8

Gln Ser Ala Cys Thr Ile Gln Ala Glu Thr His Pro Pro Leu Thr Trp
1               5                   10                  15

Gln Lys Cys Ser Ser Gly Gly Ser Cys Thr Ser Gln Thr Gly Ser Val
                20                  25                  30

Val Ile Asp Ala Asn Trp Arg Trp Thr His Ala Thr Asn Ser Thr Thr
            35                  40                  45

Asn Cys Tyr Asp Gly Asn Thr Trp Ser Ser Ser Leu Cys Pro Asp Asn
50                  55                  60

Glu Ser Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Gln Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Ser
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Glu Ala Asn Val Glu Gly Trp
            180                 185                 190

Glu Pro Ala Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
```

```
                 210                 215                 220
Leu Thr Pro His Pro Cys Thr Val Gly Gln Ala Ile Cys Asp Gly
225                 230                 235                 240

Asp Gly Cys Gly Gly Thr Tyr Ser Asp Asp Arg Tyr Gly Gly Thr Cys
                245                 250                 255

Asp Pro Asp Gly Cys Asp Trp Asn Pro Tyr Arg Leu Gly Asn Thr Ser
                260                 265                 270

Xaa Tyr Gly Pro Gly Ser Ser Phe Thr Leu Asp Thr Thr Lys Lys Met
                275                 280                 285

Thr Val Val Thr Gln Phe Ala Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Thr Leu Asn Asp Ala Tyr Cys Ala Ala Glu Glu Ala
                325                 330                 335

Glu Phe Gly Gly Ser Ser Phe Ser Asp Lys Gly Gly Leu Thr Gln Phe
                340                 345                 350

Lys Gln Ala Thr Ser Gly Gly Met Val Leu Val Met Ser Leu Trp Asp
                355                 360                 365

Asp Tyr Tyr Ala Asn Met Leu Trp Leu Asp Ser Ile Tyr Pro Thr Asn
370                 375                 380

Glu Thr Ser Ser Thr Pro Gly Ala Ala Arg Gly Ser Cys Ser Thr Ser
385                 390                 395                 400

Ser Gly Val Pro Ala Gln Leu Glu Ser Gln Ser Thr Asn Ala Lys Val
                405                 410                 415

Val Phe Ser Asn Ile Lys Phe Gly Pro Ile Gly Ser Thr Gly Asn Ser
                420                 425                 430

Ser Gly Gly Asn Pro Pro Gly Gly Asn Pro Pro Gly Thr Thr Thr
                435                 440                 445

Thr Arg Arg Pro Ala Thr Thr Thr Gly Ser Ser Pro Gly Pro Thr Gln
450                 455                 460

Thr His Tyr Gly Gln Cys Gly Gly Ile Gly Tyr Ser Gly Pro Thr Val
465                 470                 475                 480

Cys Ala Ser Gly Ser Thr Cys Gln Val Leu Asn Pro Tyr Tyr Ser Gln
                485                 490                 495

Cys Leu

<210> SEQ ID NO 9
<211> LENGTH: 488
<212> TYPE: PRT
<213> ORGANISM: Trichoderma harzanium

<400> SEQUENCE: 9

Gln Gln Val Cys Thr Gln Gln Ala Glu Thr His Pro Pro Leu Thr Trp
1               5                   10                  15

Gln Lys Cys Thr Ala Ser Gly Cys Thr Pro Gln Gly Ser Val Val
                20                  25                  30

Leu Asp Ala Asn Trp Arg Trp Thr His Asp Thr Lys Ser Thr Thr Asn
                35                  40                  45

Cys Tyr Asp Gly Asn Thr Trp Ser Ser Thr Leu Cys Pro Asp Asp Ala
                50                  55                  60

Thr Cys Ala Lys Asn Cys Cys Leu Asp Gly Ala Asn Tyr Ser Gly Thr
65                  70                  75                  80

Tyr Gly Val Thr Thr Ser Gly Asp Ala Leu Thr Leu Gln Phe Val Thr
```

```
                    85                  90                  95
Ala Ser Asn Val Gly Ser Arg Leu Tyr Leu Met Ala Asn Asp Ser Thr
                100                 105                 110

Tyr Gln Glu Phe Thr Leu Ser Gly Asn Glu Phe Ser Phe Asp Val Asp
            115                 120                 125

Val Ser Gln Leu Pro Cys Gly Leu Asn Gly Ala Leu Tyr Phe Val Ser
        130                 135                 140

Met Asp Ala Asp Gly Gly Gln Ser Lys Tyr Pro Gly Asn Ala Ala Gly
145                 150                 155                 160

Ala Lys Tyr Gly Thr Gly Tyr Cys Asp Ser Gln Cys Pro Arg Asp Leu
                165                 170                 175

Lys Phe Ile Asn Gly Gln Ala Asn Val Glu Gly Trp Glu Pro Ser Ser
            180                 185                 190

Asn Asn Ala Asn Thr Gly Val Gly Gly His Gly Ser Cys Cys Ser Glu
        195                 200                 205

Met Asp Ile Trp Glu Ala Asn Ser Ile Ser Glu Ala Leu Thr Pro His
210                 215                 220

Pro Cys Glu Thr Val Gly Gln Thr Met Cys Ser Gly Asp Ser Cys Gly
225                 230                 235                 240

Gly Thr Tyr Ser Asn Asp Arg Tyr Gly Gly Thr Cys Asp Pro Asp Gly
                245                 250                 255

Cys Asp Trp Asn Pro Tyr Arg Leu Gly Asn Thr Ser Phe Tyr Gly Pro
            260                 265                 270

Gly Ser Ser Phe Ala Leu Asp Thr Thr Lys Lys Leu Thr Val Val Thr
        275                 280                 285

Gln Phe Ala Thr Asp Gly Ser Ile Ser Arg Tyr Tyr Val Gln Asn Gly
290                 295                 300

Val Lys Phe Gln Gln Pro Asn Ala Gln Val Gly Ser Tyr Ser Gly Asn
305                 310                 315                 320

Thr Ile Asn Thr Asp Tyr Cys Ala Ala Glu Gln Thr Ala Phe Gly Gly
                325                 330                 335

Thr Ser Phe Thr Asp Lys Gly Gly Leu Ala Gln Ile Asn Lys Ala Phe
            340                 345                 350

Gln Gly Gly Met Val Leu Val Met Ser Leu Trp Asp Asp Tyr Ala Val
        355                 360                 365

Asn Met Leu Trp Leu Asp Ser Thr Tyr Pro Thr Asn Ala Thr Ala Ser
370                 375                 380

Thr Pro Gly Ala Lys Arg Gly Ser Cys Ser Thr Ser Ser Gly Val Pro
385                 390                 395                 400

Ala Gln Val Glu Ala Gln Ser Pro Asn Ser Lys Val Ile Tyr Ser Asn
                405                 410                 415

Ile Arg Phe Gly Pro Ile Gly Ser Thr Gly Asn Thr Gly Ser Asn
            420                 425                 430

Pro Pro Gly Thr Ser Thr Thr Arg Ala Pro Pro Ser Ser Thr Gly Ser
        435                 440                 445

Ser Pro Thr Ala Thr Gln Thr His Tyr Gly Gln Cys Gly Gly Thr Gly
        450                 455                 460

Trp Thr Gly Pro Thr Arg Cys Ala Ser Gly Tyr Thr Cys Gln Val Leu
465                 470                 475                 480

Asn Pro Phe Tyr Ser Gln Cys Leu
                485

<210> SEQ ID NO 10
```

<211> LENGTH: 518
<212> TYPE: PRT
<213> ORGANISM: Aspergillus aculeatus

<400> SEQUENCE: 10

```
Gln Gln Val Gly Thr Tyr Thr Ala Glu Thr His Pro Ser Leu Thr Trp
1               5                   10                  15

Gln Thr Cys Ser Gly Ser Gly Ser Cys Thr Thr Thr Ser Gly Ser Val
            20                  25                  30

Val Ile Asp Ala Asn Trp Arg Trp Val His Glu Val Gly Gly Tyr Thr
        35                  40                  45

Asn Cys Tyr Ser Gly Asn Thr Trp Asp Ser Ser Ile Cys Ser Thr Asp
    50                  55                  60

Thr Thr Cys Ala Ser Glu Cys Ala Leu Glu Gly Ala Thr Tyr Glu Ser
65                  70                  75                  80

Thr Tyr Gly Val Thr Thr Ser Gly Ser Ser Leu Arg Leu Asn Phe Val
                85                  90                  95

Thr Thr Ala Ser Gln Lys Asn Ile Gly Ser Arg Leu Tyr Leu Leu Ala
            100                 105                 110

Asp Asp Ser Thr Tyr Glu Thr Phe Lys Leu Phe Asn Arg Glu Phe Thr
        115                 120                 125

Phe Asp Val Asp Val Ser Asn Leu Pro Cys Gly Leu Asn Gly Ala Leu
    130                 135                 140

Tyr Phe Val Ser Met Asp Ala Asp Gly Gly Val Ser Arg Phe Pro Thr
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asp Gly Gln Ala Asn Ile Glu Gly Trp
            180                 185                 190

Glu Pro Ser Ser Thr Asp Val Asn Ala Gly Thr Gly Asn His Gly Ser
        195                 200                 205

Cys Cys Pro Glu Met Asp Ile Trp Glu Ala Asn Ser Ile Ser Ser Ala
    210                 215                 220

Phe Thr Ala His Pro Cys Asp Ser Val Gln Gln Thr Met Cys Thr Gly
225                 230                 235                 240

Asp Thr Cys Gly Gly Thr Tyr Ser Asp Thr Thr Asp Arg Tyr Ser Gly
                245                 250                 255

Thr Cys Asp Pro Asp Gly Cys Asp Phe Asn Pro Tyr Arg Phe Gly Asn
            260                 265                 270

Thr Asn Phe Tyr Gly Pro Gly Lys Thr Val Asp Asn Ser Lys Pro Phe
        275                 280                 285

Thr Val Val Thr Gln Phe Ile Thr His Asp Gly Thr Asp Thr Gly Thr
    290                 295                 300

Leu Thr Glu Ile Arg Arg Leu Tyr Val Gln Asn Gly Val Val Ile Gly
305                 310                 315                 320

Asn Gly Pro Ser Thr Tyr Thr Ala Ala Ser Gly Asn Ser Ile Thr Glu
                325                 330                 335

Ser Phe Cys Lys Ala Glu Lys Thr Leu Phe Gly Asp Thr Asn Val Phe
            340                 345                 350

Glu Thr His Gly Gly Leu Ser Ala Met Gly Asp Ala Leu Gly Asp Gly
        355                 360                 365

Met Val Leu Val Leu Ser Leu Trp Asp Asp His Ala Ala Asp Met Leu
    370                 375                 380

Trp Leu Asp Ser Asp Tyr Pro Thr Thr Ser Cys Ala Ser Ser Pro Gly
```

```
                385                 390                 395                 400
Val Ala Arg Gly Thr Cys Pro Thr Thr Thr Gly Asn Ala Thr Tyr Val
                    405                 410                 415

Glu Ala Asn Tyr Pro Asn Ser Tyr Val Thr Tyr Ser Asn Ile Lys Phe
                420                 425                 430

Gly Thr Leu Asn Ser Thr Tyr Ser Gly Thr Ser Ser Gly Ser Ser
                    435                 440                 445

Ser Ser Ser Thr Thr Leu Thr Thr Lys Ala Ser Thr Ser Thr Thr Ser
            450                 455                 460

Ser Lys Thr Thr Thr Thr Thr Ser Lys Thr Ser Thr Thr Ser Ser Ser
465                 470                 475                 480

Ser Thr Asn Val Ala Gln Leu Tyr Gly Gln Cys Gly Gly Gln Gly Trp
                    485                 490                 495

Thr Gly Pro Thr Thr Cys Ala Ser Gly Thr Cys Thr Lys Gln Asn Asp
                500                 505                 510

Tyr Tyr Ser Gln Cys Leu
            515

<210> SEQ ID NO 11
<211> LENGTH: 515
<212> TYPE: PRT
<213> ORGANISM: Aspergillus niger

<400> SEQUENCE: 11

Gln Gln Val Gly Thr Tyr Thr Thr Glu Thr His Pro Ser Leu Thr Trp
1               5                   10                  15

Gln Thr Cys Thr Ser Ser Gly Ser Cys Thr Thr Asn Asp Gly Ala Val
                    20                  25                  30

Val Ile Asp Ala Asn Trp Arg Trp Val His Ser Thr Ser Ser Ser Thr
                35                  40                  45

Asn Cys Tyr Thr Gly Asn Glu Trp Asp Thr Ser Ile Cys Thr Asp Asp
    50                  55                  60

Val Thr Cys Ala Ala Asn Cys Ala Leu Asp Gly Ala Thr Tyr Glu Ala
65                  70                  75                  80

Thr Tyr Gly Val Thr Thr Ser Gly Asp Glu Leu Arg Leu Asn Phe Val
                85                  90                  95

Thr Gln Gly Ser Ser Lys Asn Ile Gly Ser Arg Leu Tyr Leu Met Ser
                    100                 105                 110

Asp Asp Ser Thr Tyr Glu Met Phe Lys Leu Leu Gly Gln Glu Phe Thr
                115                 120                 125

Phe Asp Val Asp Val Ser Asn Leu Pro Cys Gly Leu Asn Gly Ala Leu
            130                 135                 140

Tyr Phe Val Ala Met Asp Ala Asp Gly Gly Thr Ser Glu Tyr Ser Gly
145                 150                 155                 160

Asn Lys Ala Gly Ala Lys Tyr Gly Thr Gly Tyr Cys Asp Ser Gln Cys
                    165                 170                 175

Pro Arg Asp Leu Lys Phe Ile Asn Gly Glu Ala Asn Cys Asp Gly Trp
                180                 185                 190

Glu Pro Ser Ser Asn Asn Val Asn Thr Gly Val Gly Asp His Gly Ser
                195                 200                 205

Cys Cys Pro Glu Met Asp Ile Trp Glu Ala Asn Ser Ile Ser Asn Ala
        210                 215                 220

Phe Thr Ala His Pro Cys Asp Ser Val Ser Gln Thr Met Cys Asp Gly
225                 230                 235                 240
```

Asp Ser Cys Gly Gly Thr Tyr Ser Ala Ser Gly Asp Arg Tyr Ser Gly
                245                 250                 255

Thr Cys Asp Pro Asp Gly Cys Tyr Asn Pro Tyr Arg Leu Gly Asn
        260                 265                 270

Thr Asp Phe Tyr Gly Pro Gly Leu Thr Val Asp Thr Asn Ser Pro Phe
        275                 280                 285

Thr Val Val Thr Gln Phe Ile Thr Asp Asp Gly Thr Ser Ser Gly Thr
    290                 295                 300

Leu Thr Glu Ile Lys Arg Leu Tyr Val Gln Asn Gly Glu Val Ile Ala
305                 310                 315                 320

Asn Gly Ala Ser Thr Tyr Ser Ser Val Asn Gly Ser Ser Ile Thr Ser
                325                 330                 335

Asp Phe Cys Glu Ser Glu Lys Thr Leu Phe Gly Asp Glu Asn Val Phe
            340                 345                 350

Asp Thr His Gly Gly Leu Ala Gly Met Gly Glu Ala Met Ala Asn Gly
        355                 360                 365

Met Val Leu Val Leu Ser Leu Trp Asp Asp Tyr Ala Ala Asn Met Leu
370                 375                 380

Trp Leu Asp Ser Asp Tyr Pro Val Asn Ser Ser Ala Ser Thr Pro Gly
385                 390                 395                 400

Val Ala Arg Gly Thr Cys Ser Thr Asp Ser Gly Val Pro Ala Thr Val
                405                 410                 415

Glu Ala Asp Ser Pro Asn Ala Tyr Val Thr Tyr Ser Asn Ile Lys Phe
            420                 425                 430

Gly Pro Ile Gly Ser Thr Tyr Ser Ser Gly Ser Ser Gly Ser Gly
        435                 440                 445

Ser Ser Ser Ser Ser Ser Thr Thr Thr Lys Ala Thr Ser Thr Thr
    450                 455                 460

Leu Lys Thr Thr Thr Thr Ser Ser Gly Ser Ser Thr Ser Ala
465                 470                 475                 480

Ala Gln Ala Tyr Gly Gln Cys Gly Gly Gln Ser Trp Thr Gly Pro Thr
                485                 490                 495

Thr Cys Val Ser Gly Tyr Thr Cys Thr Tyr Gln Asn Ala Tyr Tyr Ser
            500                 505                 510

Gln Cys Leu
        515

```
<210> SEQ ID NO 12
<211> LENGTH: 512
<212> TYPE: PRT
<213> ORGANISM: Penicillium janthinellum
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 12
```

Gln Gln Val Gly Thr Leu Thr Ala Glu Thr His Pro Ala Leu Thr Trp
1               5                   10                  15

Ser Lys Cys Thr Ala Gly Xaa Cys Ser Gln Val Ser Gly Ser Val Val
            20                  25                  30

Ile Asp Ala Asn Trp Pro Xaa Val His Ser Thr Ser Gly Ser Thr Asn
        35                  40                  45

```
Cys Tyr Thr Gly Asn Thr Trp Asp Ala Thr Leu Cys Pro Asp Asp Val
    50                  55                  60

Thr Cys Ala Ala Asn Cys Ala Val Asp Gly Ala Arg Arg Gln His Leu
65                  70                  75                  80

Arg Val Thr Thr Ser Gly Asn Ser Leu Arg Ile Asn Phe Val Thr Thr
                85                  90                  95

Ala Ser Gln Lys Asn Ile Gly Ser Arg Leu Tyr Leu Glu Asn Asp
            100                 105                 110

Thr Thr Tyr Gln Lys Phe Asn Leu Leu Asn Gln Glu Phe Thr Phe Asp
            115                 120                 125

Val Asp Val Ser Asn Leu Pro Cys Gly Leu Asn Gly Ala Leu Tyr Phe
130                 135                 140

Val Asp Met Asp Ala Asp Gly Gly Met Ala Lys Tyr Pro Thr Asn Lys
145                 150                 155                 160

Ala Gly Ala Lys Tyr Gly Thr Gly Tyr Cys Asp Ser Gln Cys Pro Arg
                165                 170                 175

Asp Leu Lys Phe Ile Asn Gly Gln Ala Asn Val Asp Gly Trp Thr Pro
            180                 185                 190

Ser Lys Asn Asp Val Asn Ser Gly Ile Gly Asn His Gly Ser Cys Cys
            195                 200                 205

Ala Glu Met Asp Ile Trp Glu Ala Asn Ser Ile Ser Asn Ala Val Thr
            210                 215                 220

Pro His Pro Cys Asp Thr Pro Ser Gln Thr Met Cys Thr Gly Gln Arg
225                 230                 235                 240

Cys Gly Gly Thr Tyr Ser Thr Asp Arg Tyr Gly Gly Thr Cys Asp Pro
                245                 250                 255

Asp Gly Cys Asp Phe Asn Pro Tyr Arg Met Gly Val Thr Asn Phe Tyr
            260                 265                 270

Gly Pro Gly Glu Thr Ile Asp Thr Lys Ser Pro Phe Thr Val Val Thr
            275                 280                 285

Gln Phe Leu Thr Asn Asp Gly Thr Ser Thr Gly Thr Leu Ser Glu Ile
290                 295                 300

Lys Arg Phe Tyr Val Gln Gly Gly Lys Val Ile Gly Asn Pro Gln Ser
305                 310                 315                 320

Thr Ile Val Gly Val Ser Gly Asn Ser Ile Thr Asp Ser Trp Cys Asn
                325                 330                 335

Ala Gln Lys Ser Ala Phe Gly Asp Thr Asn Glu Phe Ser Lys His Gly
            340                 345                 350

Gly Met Ala Gly Met Gly Ala Gly Leu Ala Asp Gly Met Val Leu Val
            355                 360                 365

Met Ser Leu Trp Asp Asp His Ala Ser Asp Met Leu Trp Leu Asp Ser
370                 375                 380

Thr Tyr Pro Thr Asn Ala Thr Ser Thr Thr Pro Gly Ala Lys Arg Gly
385                 390                 395                 400

Thr Cys Asp Ile Ser Arg Arg Pro Asn Thr Val Glu Ser Thr Tyr Pro
                405                 410                 415

Asn Ala Tyr Val Ile Tyr Ser Asn Ile Lys Thr Gly Pro Leu Asn Ser
            420                 425                 430

Thr Phe Thr Gly Gly Thr Ser Ser Ser Thr Thr Thr Thr
            435                 440                 445

Ser Lys Ser Thr Ser Thr Ser Ser Ser Lys Thr Thr Thr Thr Val
450                 455                 460

Thr Thr Thr Thr Thr Ser Ser Gly Ser Ser Gly Thr Gly Ala Arg Asp
```

```
            465                 470                 475                 480
Trp Ala Gln Cys Gly Gly Asn Gly Trp Thr Gly Pro Thr Thr Cys Val
                    485                 490                 495
Ser Pro Tyr Thr Cys Thr Lys Gln Asn Asp Trp Tyr Ser Gln Cys Leu
                    500                 505                 510

<210> SEQ ID NO 13
<211> LENGTH: 507
<212> TYPE: PRT
<213> ORGANISM: Humicola grisea

<400> SEQUENCE: 13

Gln Gln Ala Cys Ser Leu Thr Thr Glu Arg His Pro Ser Leu Ser Trp
1               5                   10                  15
Lys Lys Cys Thr Ala Gly Gly Gln Cys Gln Thr Val Gln Ala Ser Ile
                20                  25                  30
Thr Leu Asp Ser Asn Trp Arg Trp Thr His Gln Val Ser Gly Ser Thr
            35                  40                  45
Asn Cys Tyr Thr Gly Asn Lys Trp Asp Thr Ser Ile Cys Thr Asp Ala
        50                  55                  60
Lys Ser Cys Ala Gln Asn Cys Cys Val Asp Gly Ala Asp Tyr Thr Ser
65                  70                  75                  80
Thr Tyr Gly Ile Thr Thr Asn Gly Asp Ser Leu Ser Leu Lys Phe Val
                85                  90                  95
Thr Lys Gly Gln His Ser Thr Asn Val Gly Ser Arg Thr Tyr Leu Met
                100                 105                 110
Asp Gly Glu Asp Lys Tyr Gln Thr Phe Glu Leu Leu Gly Asn Glu Phe
            115                 120                 125
Thr Phe Asp Val Asp Val Ser Asn Ile Gly Cys Gly Leu Asn Gly Ala
        130                 135                 140
Leu Tyr Phe Val Ser Met Asp Ala Asp Gly Gly Leu Ser Arg Tyr Pro
145                 150                 155                 160
Gly Asn Lys Ala Gly Ala Lys Tyr Gly Thr Gly Tyr Cys Asp Ala Gln
                165                 170                 175
Cys Pro Arg Asp Ile Lys Phe Ile Asn Gly Glu Ala Asn Ile Glu Gly
            180                 185                 190
Trp Thr Gly Ser Thr Asn Asp Pro Asn Ala Gly Ala Gly Arg Tyr Gly
        195                 200                 205
Thr Cys Cys Ser Glu Met Asp Ile Trp Glu Ala Asn Asn Met Ala Thr
        210                 215                 220
Ala Phe Thr Pro His Pro Cys Thr Ile Ile Gly Gln Ser Arg Cys Glu
225                 230                 235                 240
Gly Asp Ser Cys Gly Gly Thr Tyr Ser Asn Glu Arg Tyr Ala Gly Val
                245                 250                 255
Cys Asp Pro Asp Gly Cys Asp Phe Asn Ser Tyr Arg Gln Gly Asn Lys
            260                 265                 270
Thr Phe Tyr Gly Lys Gly Met Thr Val Asp Thr Thr Lys Lys Ile Thr
        275                 280                 285
Val Val Thr Gln Phe Leu Lys Asp Ala Asn Gly Asp Leu Gly Glu Ile
        290                 295                 300
Lys Arg Phe Tyr Val Gln Asp Gly Lys Ile Ile Pro Asn Ser Glu Ser
305                 310                 315                 320
Thr Ile Pro Gly Val Glu Gly Asn Ser Ile Thr Gln Asp Trp Cys Asp
                325                 330                 335
```

```
Arg Gln Lys Val Ala Phe Gly Asp Ile Asp Asp Phe Asn Arg Lys Gly
                340                 345                 350

Gly Met Lys Gln Met Gly Lys Ala Leu Ala Gly Pro Met Val Leu Val
            355                 360                 365

Met Ser Ile Trp Asp Asp His Ala Ser Asn Met Leu Trp Leu Asp Ser
370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
                420                 425                 430

Thr Val Ala Gly Leu Pro Gly Ala Gly Asn Gly Gly Asn Asn Gly Gly
                435                 440                 445

Asn Pro Pro Pro Pro Thr Thr Thr Ser Ser Ala Pro Ala Thr Thr
                450                 455                 460

Thr Thr Ala Ser Ala Gly Pro Lys Ala Gly Arg Trp Gln Gln Cys Gly
465                 470                 475                 480

Gly Ile Gly Phe Thr Gly Pro Thr Gln Cys Glu Glu Pro Tyr Thr Cys
                485                 490                 495

Thr Lys Leu Asn Asp Trp Tyr Ser Gln Cys Leu
                500                 505

<210> SEQ ID NO 14
<211> LENGTH: 515
<212> TYPE: PRT
<213> ORGANISM: Scytalidium thermophilum

<400> SEQUENCE: 14

Gln Gln Ala Cys Ser Leu Thr Thr Glu Arg His Pro Ser Leu Ser Trp
1               5                   10                  15

Lys Lys Cys Thr Ala Gly Gly Gln Cys Gln Thr Val Gln Ala Ser Ile
                20                  25                  30

Thr Leu Asp Ser Asn Trp Arg Trp Thr His Gln Val Ser Gly Ser Thr
                35                  40                  45

Asn Cys Tyr Thr Gly Asn Glu Trp Asp Ser Ser Ile Cys Thr Asp Ala
50                  55                  60

Lys Ser Cys Ala Gln Asn Cys Cys Val Asp Gly Ala Asp Tyr Thr Ser
65                  70                  75                  80

Thr Tyr Gly Ile Thr Thr Asn Gly Asp Ser Leu Ser Leu Lys Phe Val
                85                  90                  95

Thr Lys Gly Gln Tyr Ser Thr Asn Val Gly Ser Arg Thr Tyr Leu Met
                100                 105                 110

Asp Gly Glu Asp Lys Tyr Gln Thr Phe Glu Leu Leu Gly Asn Glu Phe
                115                 120                 125

Thr Phe Asp Val Asp Val Ser Asn Ile Gly Cys Gly Leu Asn Gly Ala
                130                 135                 140

Leu Tyr Phe Val Ser Met Asp Ala Asp Gly Gly Leu Ser Arg Tyr Pro
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
                180                 185                 190

Trp Thr Gly Ser Thr Asn Asp Pro Asn Ala Gly Ala Gly Arg Tyr Gly
                195                 200                 205
```

Thr Cys Cys Ser Glu Met Asp Ile Trp Glu Ala Asn Asn Met Ala Thr
                210                 215                 220

Ala Phe Thr Pro His Pro Cys Thr Ile Ile Gly Gln Ser Arg Cys Glu
225                 230                 235                 240

Gly Asp Ser Cys Gly Gly Thr Tyr Ser Asn Asp Arg Tyr Ala Gly Val
                245                 250                 255

Cys Asp Pro Asp Gly Cys Asp Phe Asn Ala Tyr Arg Gln Gly Asn Lys
                260                 265                 270

Thr Phe Tyr Gly Lys Gly Met Thr Val Asp Thr Thr Lys Lys Leu Thr
                275                 280                 285

Val Val Thr Gln Phe Leu Lys Asp Ala Asn Gly Asp Leu Gly Glu Ile
290                 295                 300

Lys Arg Phe Tyr Val Gln Asp Gly Lys Ile Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Val Ala Phe Gly Asp Ile Asp Asp Phe Asn Arg Lys Gly
                340                 345                 350

Gly Met Lys Gln Met Gly Lys Ala Leu Ala Gly Pro Met Val Leu Val
                355                 360                 365

Met Ser Ile Trp Asp Asp His Ala Ser Asn Met Leu Trp Leu Asp Ser
370                 375                 380

Thr Phe Pro Val Asp Ala Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Val Phe Ser Asn Ile Arg Phe Gly Pro Ile Gly Ser
                420                 425                 430

Thr Val Ala Gly Leu Pro Ser Asp Gly Gly Asn Asn Gly Gly Asn Thr
                435                 440                 445

Thr Val Gln Pro Pro Ser Thr Thr Thr Ser Ala Ser Ser Ser
450                 455                 460

Thr Thr Ser Ala Pro Ala Thr Thr Thr Ala Ser Ala Gly Pro Lys
465                 470                 475                 480

Ala Gly Arg Trp Gln Gln Cys Gly Gly Ile Gly Phe Thr Gly Pro Thr
                485                 490                 495

Gln Cys Glu Glu Pro Tyr Thr Cys Thr Lys Leu Asn Asp Trp Tyr Ser
                500                 505                 510

Gln Cys Leu
        515

<210> SEQ ID NO 15
<211> LENGTH: 509
<212> TYPE: PRT
<213> ORGANISM: Podospora anderina

<400> SEQUENCE: 15

Gln Gln Val Cys Ser Leu Thr Pro Glu Ser His Pro Pro Leu Thr Trp
1               5                   10                  15

Gln Arg Cys Ser Ala Gly Gly Ser Cys Thr Asn Val Ala Gly Ser Val
                20                  25                  30

Thr Leu Asp Ser Asn Trp Arg Trp Thr His Thr Leu Gln Gly Ser Thr
                35                  40                  45

Asn Cys Tyr Ser Gly Asn Glu Trp Asp Thr Ser Ile Cys Thr Thr Gly

```
                50             55              60
Thr Lys Cys Ala Gln Asn Cys Cys Val Glu Gly Ala Glu Tyr Ala Ala
65                  70                  75                  80

Thr Tyr Gly Ile Thr Thr Ser Gly Asn Gln Leu Asn Leu Lys Phe Val
                85                  90                  95

Thr Glu Gly Lys Tyr Ser Thr Asn Val Gly Ser Arg Thr Tyr Leu Met
                100                 105                 110

Glu Asn Ala Thr Lys Tyr Gln Gly Phe Asn Leu Leu Gly Asn Glu Phe
                115                 120                 125

Thr Phe Asp Val Asp Val Ser Asn Ile Gly Cys Gly Leu Asn Gly Ala
        130                 135                 140

Leu Tyr Phe Val Ser Met Asp Leu Asp Gly Leu Ala Lys Tyr Ser
145                 150                 155                 160

Gly Asn Lys Ala Gly Ala Lys Tyr Gly Thr Gly Tyr Cys Asp Ala Gln
                165                 170                 175

Cys Pro Arg Asp Ile Lys Phe Ile Asn Gly Glu Ala Asn Ile Glu Gly
            180                 185                 190

Trp Asn Pro Ser Thr Asn Asp Val Asn Ala Gly Ala Gly Arg Tyr Gly
            195                 200                 205

Thr Cys Cys Ser Glu Met Asp Ile Trp Glu Ala Asn Asn Met Ala Thr
210                 215                 220

Ala Tyr Thr Pro His Ser Cys Thr Ile Leu Asp Gln Ser Arg Cys Glu
225                 230                 235                 240

Gly Glu Ser Cys Gly Gly Thr Tyr Ser Ser Asp Arg Tyr Gly Gly Val
                245                 250                 255

Cys Asp Pro Asp Gly Cys Asp Phe Asn Ser Tyr Arg Met Gly Asn Lys
            260                 265                 270

Glu Phe Tyr Gly Lys Gly Lys Thr Val Asp Thr Thr Lys Lys Met Thr
            275                 280                 285

Val Val Thr Gln Phe Leu Lys Asn Ala Ala Gly Glu Leu Ser Glu Ile
        290                 295                 300

Lys Arg Phe Tyr Val Gln Asn Gly Val Val Ile Pro Asn Ser Val Ser
305                 310                 315                 320

Ser Ile Pro Gly Val Pro Asn Gln Asn Ser Ile Thr Gln Asp Trp Cys
            325                 330                 335

Asp Ala Gln Lys Ile Ala Phe Gly Asp Pro Asp Asn Thr Ala Lys
            340                 345                 350

Gly Gly Leu Arg Gln Met Gly Leu Ala Leu Asp Lys Pro Met Val Leu
        355                 360                 365

Val Met Ser Ile Trp Asn Asp His Ala Ala His Met Leu Trp Leu Asp
370                 375                 380

Ser Thr Tyr Pro Val Asp Ala Ala Gly Arg Pro Gly Ala Glu Arg Gly
385                 390                 395                 400

Ala Cys Pro Thr Thr Ser Gly Val Pro Ser Glu Val Glu Ala Glu Ala
                405                 410                 415

Pro Asn Ser Asn Val Ala Phe Ser Asn Ile Lys Phe Gly Pro Ile Gly
            420                 425                 430

Ser Thr Phe Asn Ser Gly Ser Thr Asn Pro Asn Pro Ile Ser Ser Ser
            435                 440                 445

Thr Ala Thr Thr Pro Thr Ser Thr Arg Val Ser Ser Thr Ser Thr Ala
        450                 455                 460

Ala Gln Thr Pro Thr Ser Ala Pro Gly Gly Thr Val Pro Arg Trp Gly
465                 470                 475                 480
```

```
Gln Cys Gly Gly Gln Gly Tyr Thr Gly Pro Thr Gln Cys Val Ala Pro
                485             490             495
Tyr Thr Cys Val Val Ser Asn Gln Trp Tyr Ser Gln Cys
            500             505
```